(12) United States Patent
Takahashi et al.

(10) Patent No.: US 11,634,474 B2
(45) Date of Patent: *Apr. 25, 2023

(54) HUMAN SERUM ALBUMIN MUTANT

(71) Applicant: JCR Pharmaceuticals Co., Ltd., Hyogo (JP)

(72) Inventors: Kenichi Takahashi, Hyogo (JP); Aya Yoshioka, Hyogo (JP); Hideto Morimoto, Hyogo (JP); Masafumi Kinoshita, Hyogo (JP)

(73) Assignee: JCR PHARMACEUTICALS CO., LTD., Hyogo (JP)

( * ) Notice: Subject to any disclaimer, the term of this patent is extended or adjusted under 35 U.S.C. 154(b) by 56 days.

This patent is subject to a terminal disclaimer.

(21) Appl. No.: 17/323,733

(22) Filed: May 18, 2021

(65) Prior Publication Data

US 2021/0269507 A1 Sep. 2, 2021

Related U.S. Application Data

(60) Continuation of application No. 16/846,003, filed on Apr. 10, 2020, now Pat. No. 11,046,751, which is a division of application No. 15/758,199, filed as application No. PCT/JP2016/076438 on Sep. 8, 2016, now Pat. No. 10,654,912.

(30) Foreign Application Priority Data

Sep. 8, 2015 (JP) .................... 2015-177093

(51) Int. Cl.
| | |
|---|---|
| *C07K 14/765* | (2006.01) |
| *A61K 38/00* | (2006.01) |
| *C12N 5/16* | (2006.01) |
| *C07K 19/00* | (2006.01) |
| *C12N 15/09* | (2006.01) |
| *A61P 43/00* | (2006.01) |
| *A61P 3/00* | (2006.01) |
| *A61P 5/06* | (2006.01) |
| *C07K 14/61* | (2006.01) |

(52) U.S. Cl.
CPC ............ *C07K 14/765* (2013.01); *A61K 38/00* (2013.01); *A61P 3/00* (2018.01); *A61P 5/06* (2018.01); *A61P 43/00* (2018.01); *C07K 14/61* (2013.01); *C07K 19/00* (2013.01); *C12N 5/16* (2013.01); *C12N 15/09* (2013.01); *C07K 2319/00* (2013.01); *C07K 2319/31* (2013.01)

(58) Field of Classification Search
CPC .................................................. C07K 14/765
See application file for complete search history.

(56) References Cited

U.S. PATENT DOCUMENTS

| | | |
|---|---|---|
| 6,399,565 B1 | 6/2002 | Asada et al. |
| 7,550,432 B2 | 6/2009 | Ballance |
| 2003/0054554 A1 | 3/2003 | Becquart et al. |
| 2006/0122374 A1 | 6/2006 | Mertins et al. |
| 2008/0131399 A1 | 6/2008 | Ballance et al. |
| 2009/0099071 A1 | 4/2009 | Nakajou et al. |

FOREIGN PATENT DOCUMENTS

| | | |
|---|---|---|
| CN | 1733807 | 2/2006 |
| CN | 101429240 | 5/2009 |
| CN | 102336828 | 2/2012 |
| JP | H03178998 | 8/1991 |
| JP | H06-269292 | 9/1994 |
| JP | H07503368 | 4/1995 |
| JP | H07503844 | 4/1995 |
| JP | 2000502901 | 3/2000 |
| JP | 2003503838 | 1/2003 |
| JP | 2005514060 | 5/2005 |
| JP | 2007522806 | 8/2007 |
| JP | 2008043285 | 2/2008 |
| JP | 2008518615 | 6/2008 |
| JP | 2010500031 | 1/2010 |
| JP | 2011015690 | 1/2011 |
| JP | 2013501036 | 1/2013 |
| JP | 2013518038 | 5/2013 |
| WO | 9315199 | 8/1993 |

(Continued)

OTHER PUBLICATIONS

Kragh-Hansen, U. et al., "The glycan structure of albumin Redhill, a glycosylated variant of human serum albumin", Biochimica et Biophysica Acta. vol. 1550, p. 20-26 (2001).

Osborn, B. L. et al, "Albutropin: a growth hormone-albumin fusion with improved pharmacokinetics and pharmacodynamics in rats and monkeys", European Journal of Pharmacology, vol. 456, p. 149-158 (2002).

Brand et al.; "Albumin Redhill, a human albumin variant", Elsevier, Clinica Chimica Acta vol. 136, Issues 2-3, Jan. 31, 1984, pp. 197-202.

(Continued)

*Primary Examiner* — Suzanne M Noakes
(74) *Attorney, Agent, or Firm* — Hamre, Schumann, Mueller & Larson, P.C.

(57) ABSTRACT

Disclosed are a human serum albumin mutant that can be linked to a physiologically active protein to increase the stability of the protein in the blood, as well as a resulting protein produced by linking with the mutant. The protein produced by linking with the mutant consists of a human serum albumin mutant comprising the amino acid sequence set forth as SEQ ID NO:3 or an amino acid sequence that, in comparison with it, lacks not more than 10 amino acid residues and/or has not more than 10 amino acid residues replaced, with the proviso that the asparagine residue occurring at position 318 and the threonine at position 320 from the N-terminus of the amino acid sequence set forth as SEQ ID NO:3 are preserved and linked by peptide bonds via a single amino acid residue (X) except proline placed between those two amino acid residues, and a physiologically active protein linked to the mutant.

13 Claims, 14 Drawing Sheets

Specification includes a Sequence Listing.

(56) References Cited

FOREIGN PATENT DOCUMENTS

| | | |
|---|---|---|
| WO | 9315211 | 8/1993 |
| WO | 97024445 | 7/1997 |
| WO | 0179258 | 10/2001 |
| WO | 03060071 | 7/2003 |
| WO | 2004/011499 | 2/2004 |
| WO | 2005077042 | 8/2005 |
| WO | 2006048777 | 5/2006 |
| WO | 2008019368 | 2/2008 |
| WO | 2011015649 | 2/2011 |
| WO | 2011089255 | 7/2011 |

OTHER PUBLICATIONS

Brennan et al,; "Albumin Redhill (−1 Arg, 320 Ala-Thr): a glycoprotein variant of human serum albumin whose precursor has an aberrant signal peptidase cleavage site", Published 1990 in Proceedings of the National Academy of Sciences of USA, vol. 87, pp. 26-30.
Poznansky et al.; "Growth hormone-albumin conjugates. Reduced renal toxicity and altered plasma clearance", US National Library of Medicine National Institutes of Health, FEBS Letters, vol. 239, p. 18-22 (1988).
Shen et al., "The effect of gene copy number and co-expression of chaperone on production of albumin fusion proteins in Pichia pastoris," Appl Microbiol Biotechnol, 96, p. 763-772 (2012).
Wang et al., "Cloning and Expr essing of HSA—GHRH Fusion Protein," Letters in Bioechnology, 18(4), p. 574-577 (2007); English abstract is on p. 574.
Qi et al., "Efficient Expression and Secretion of a Long-acting Form of Human Growth Hormone in Pichia pastoris," China Biotechnology, 32(12), p. 37-46 (2012); English abstract is on p. 45-46.

[Fig. 1]
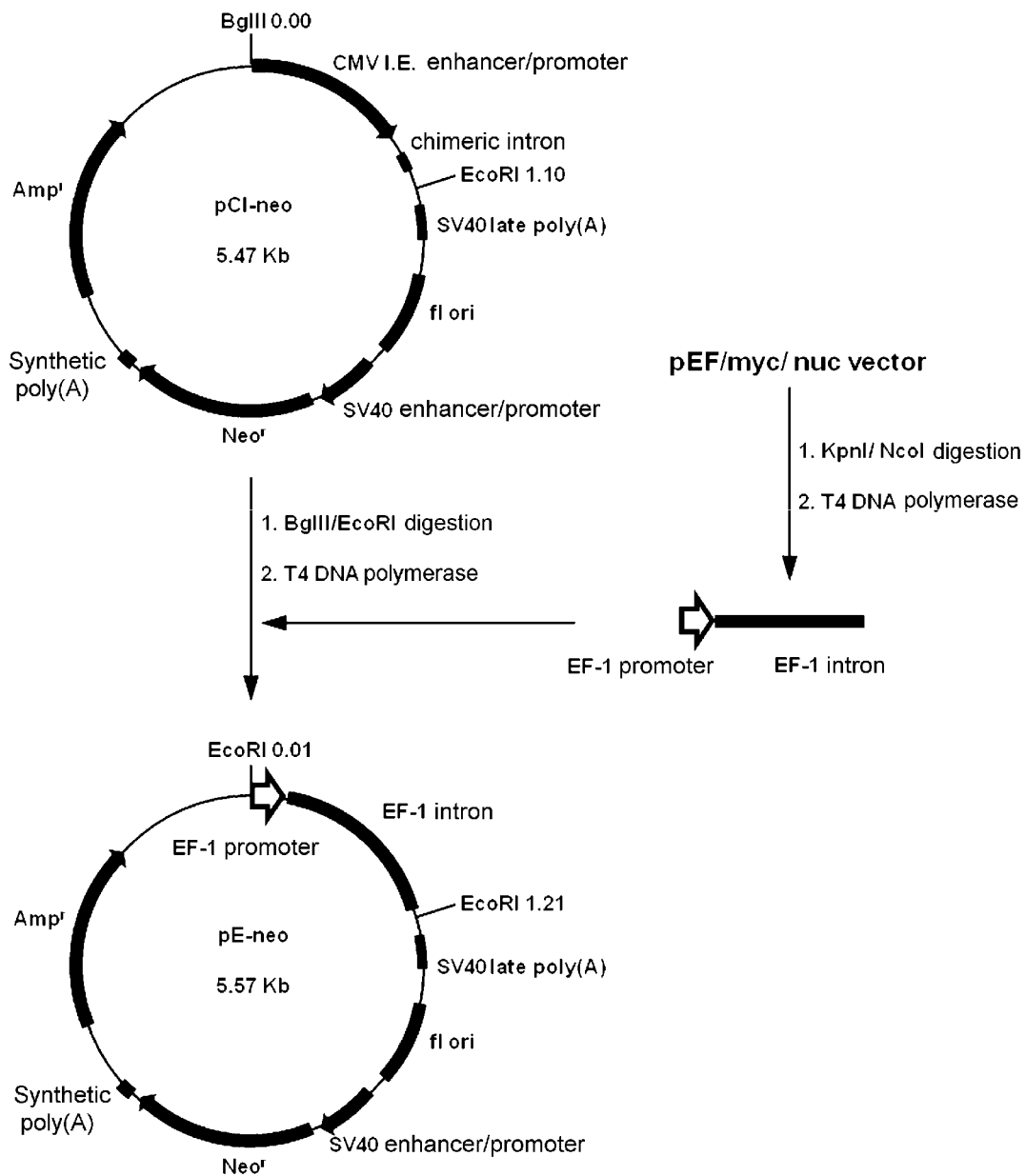

[Fig. 2]
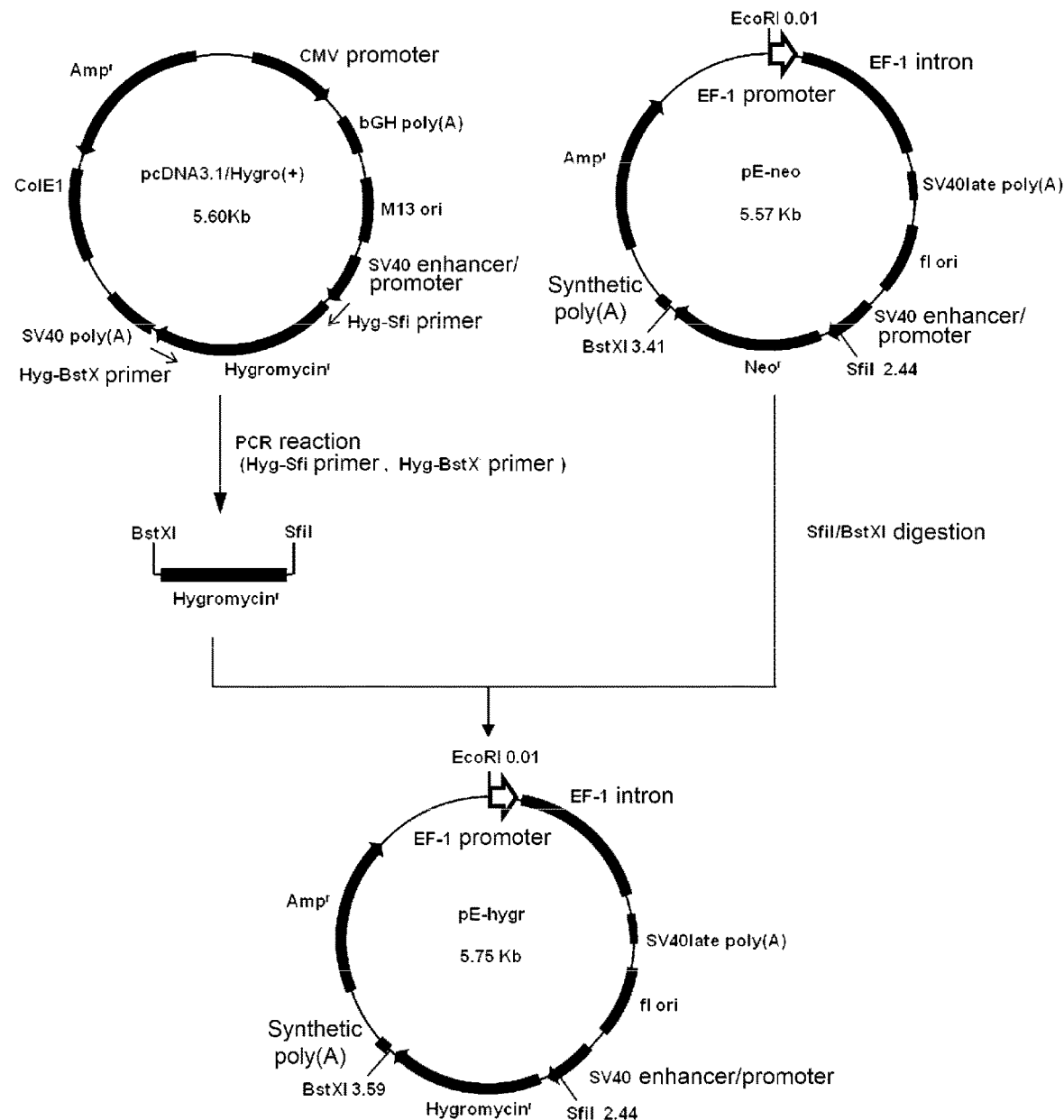

[Fig. 3-1]
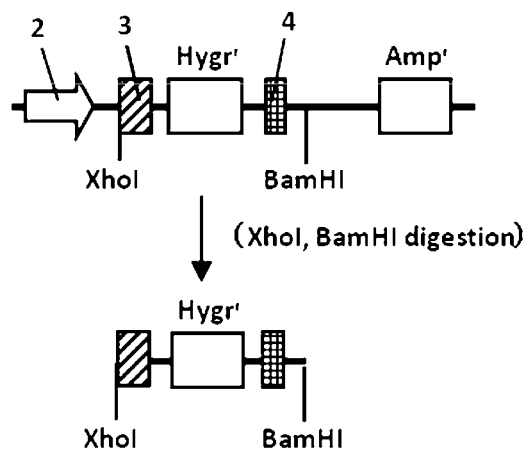

[Fig. 3-2]
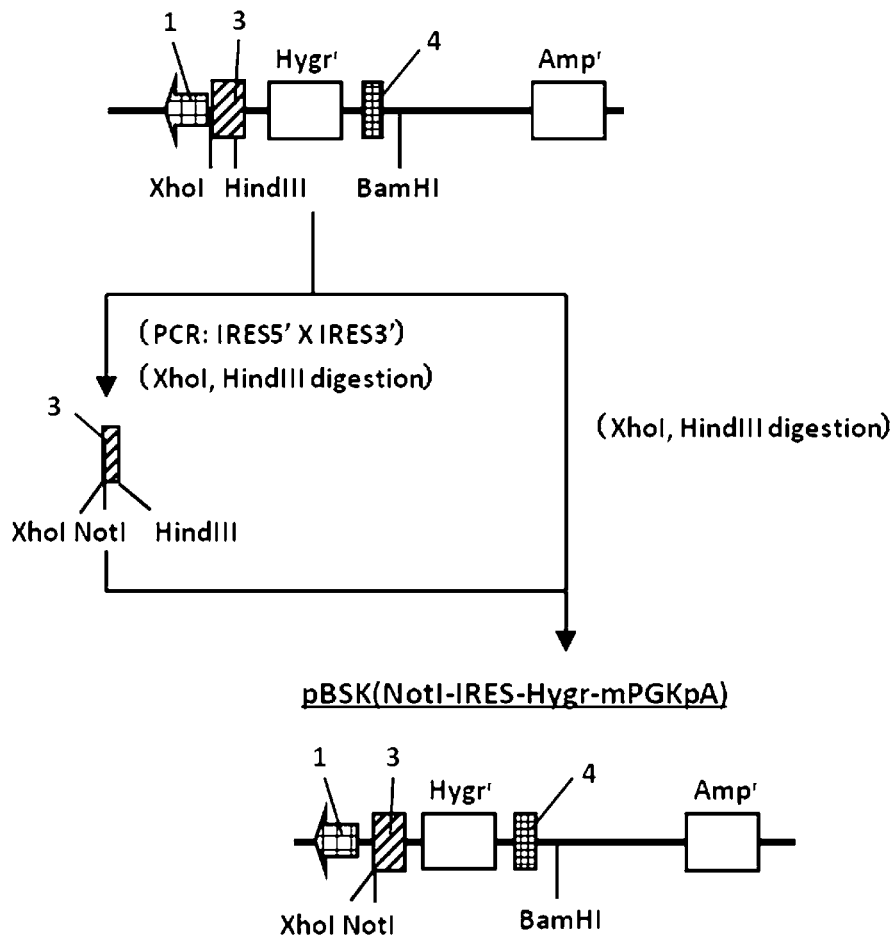

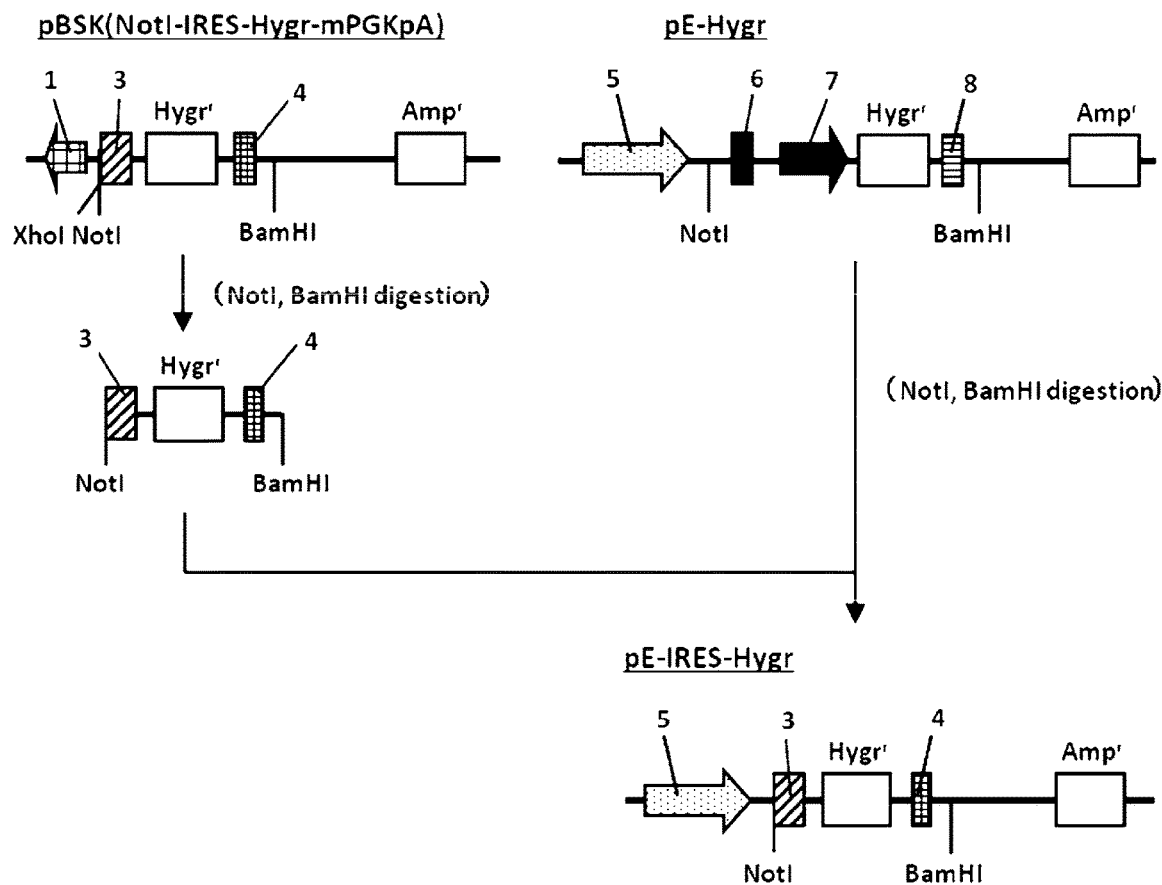
[Fig. 3-3]

[Fig. 3-4]
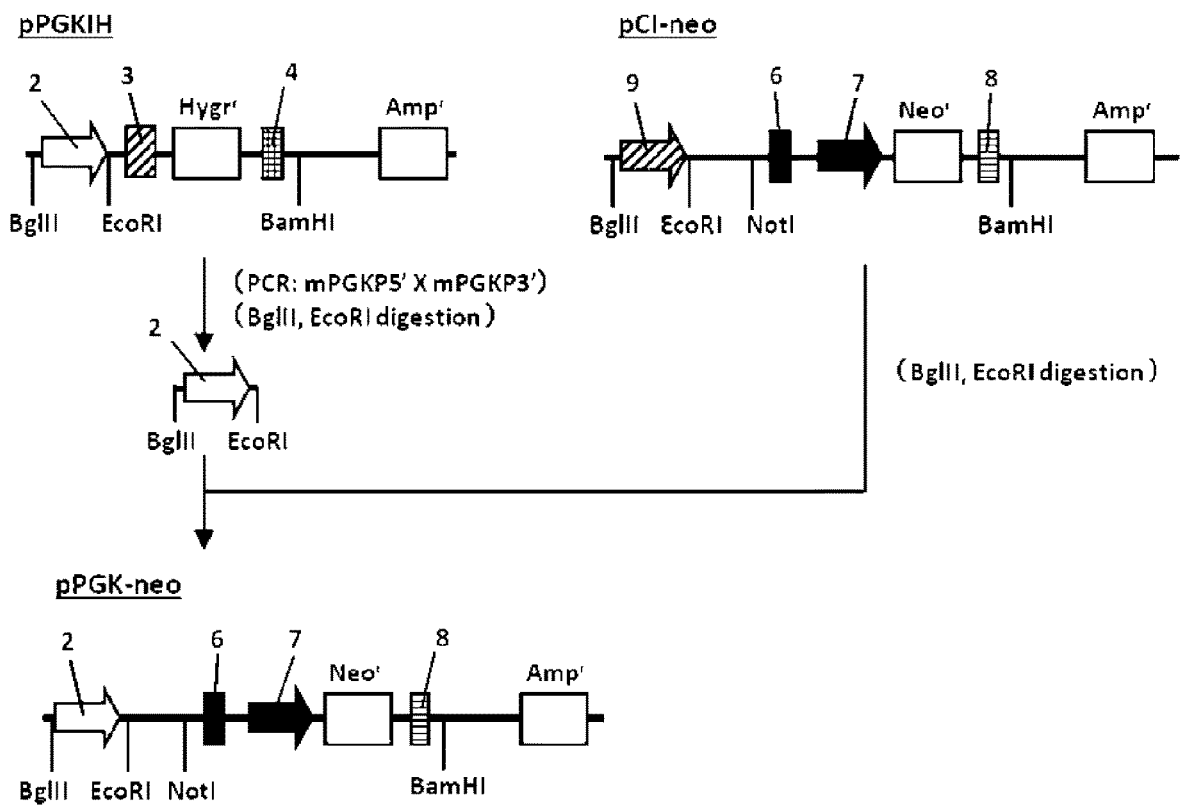

[Fig. 3-5]
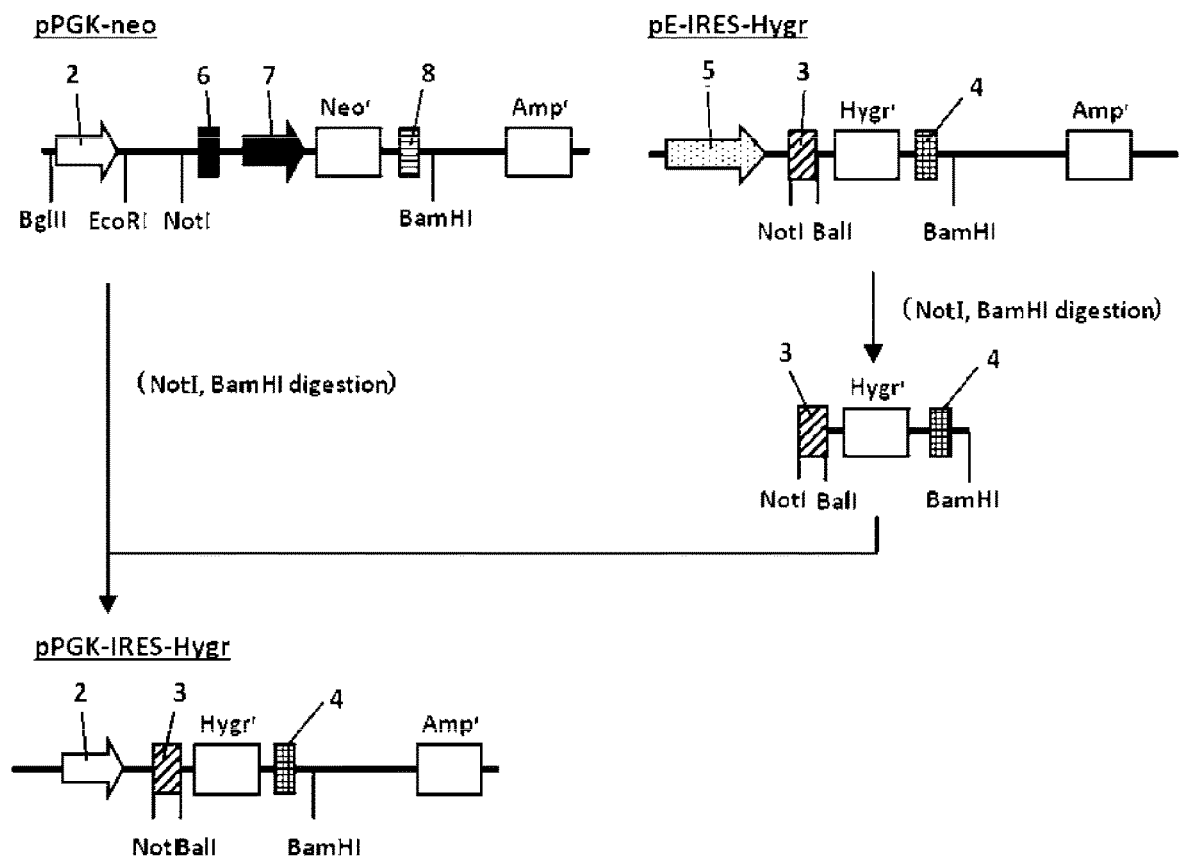

[Fig. 3-6]
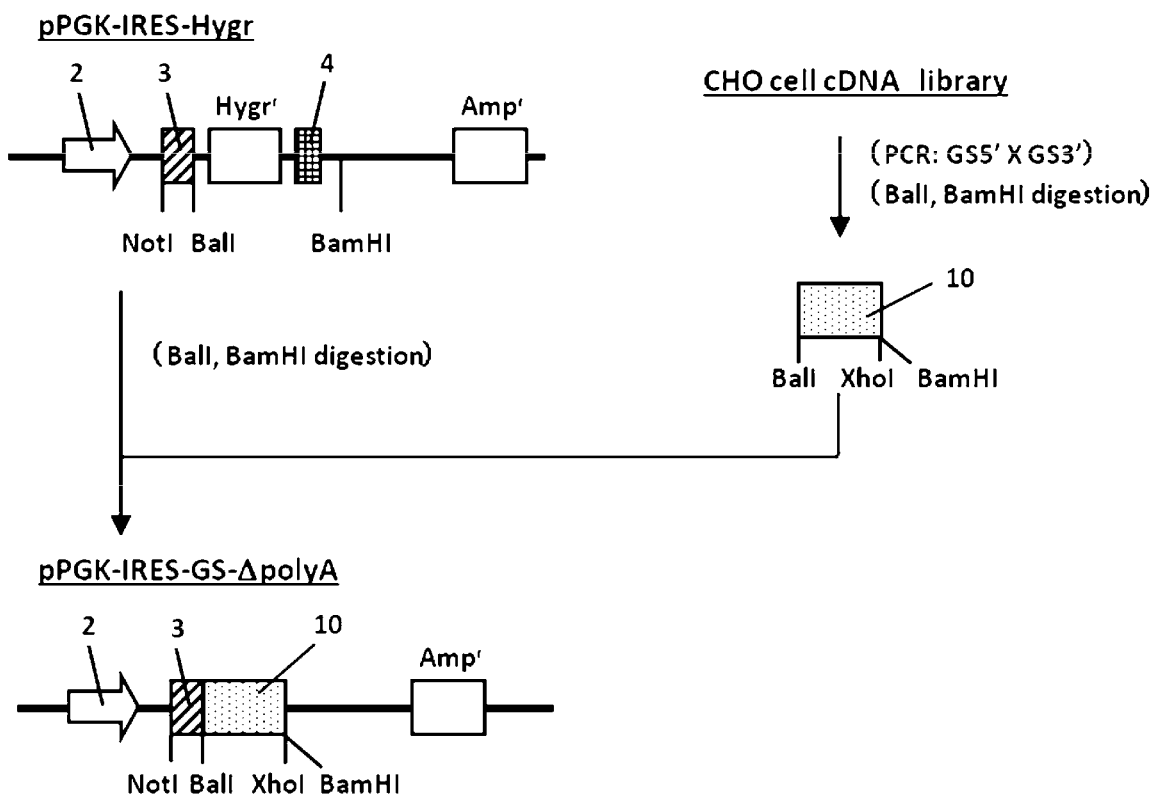

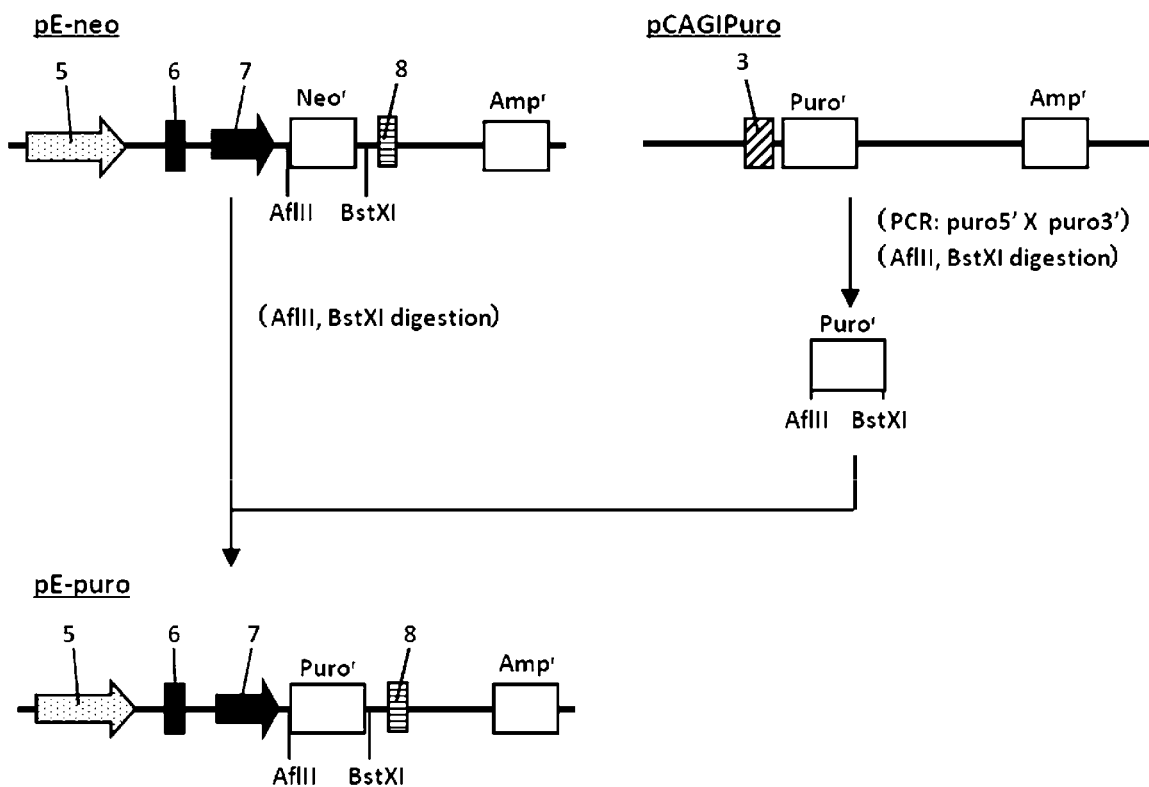
[Fig. 3-7]

[Fig. 3-8]
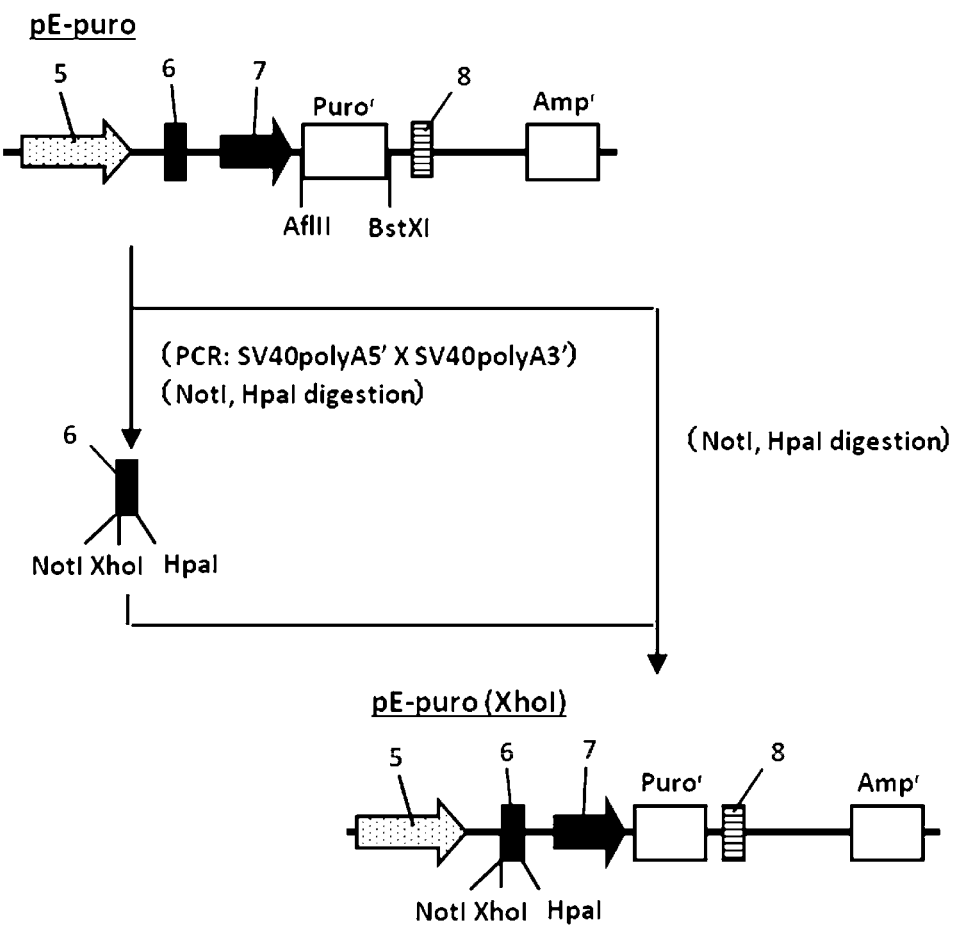

[Fig. 3-9]
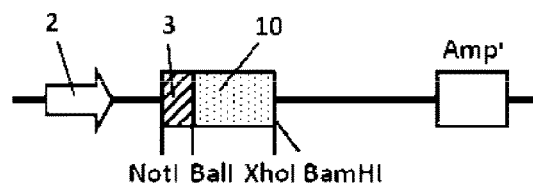
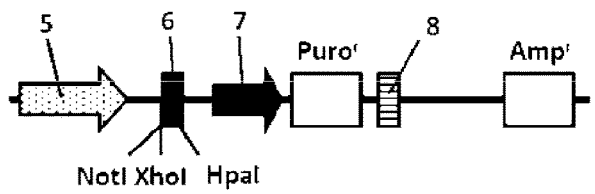
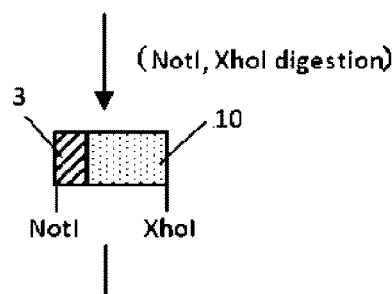
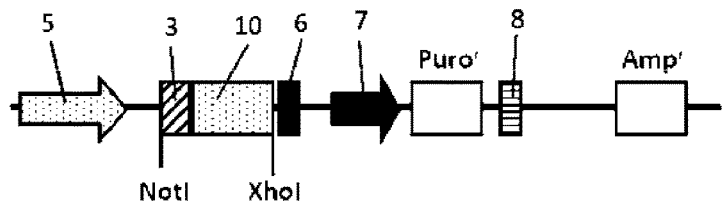

[Fig. 4]
pE-IRES-GS-puro
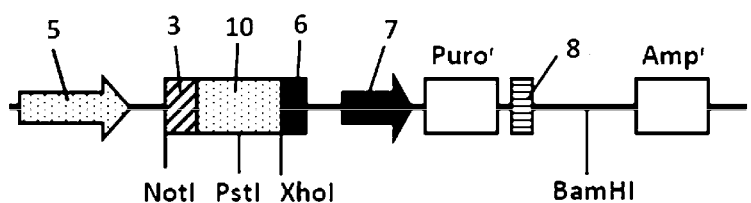
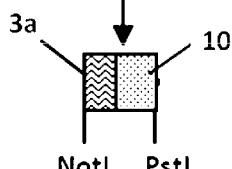
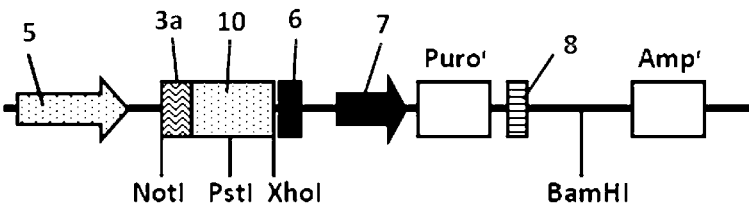
pE-mIRES-GS-puro

[Fig. 5]
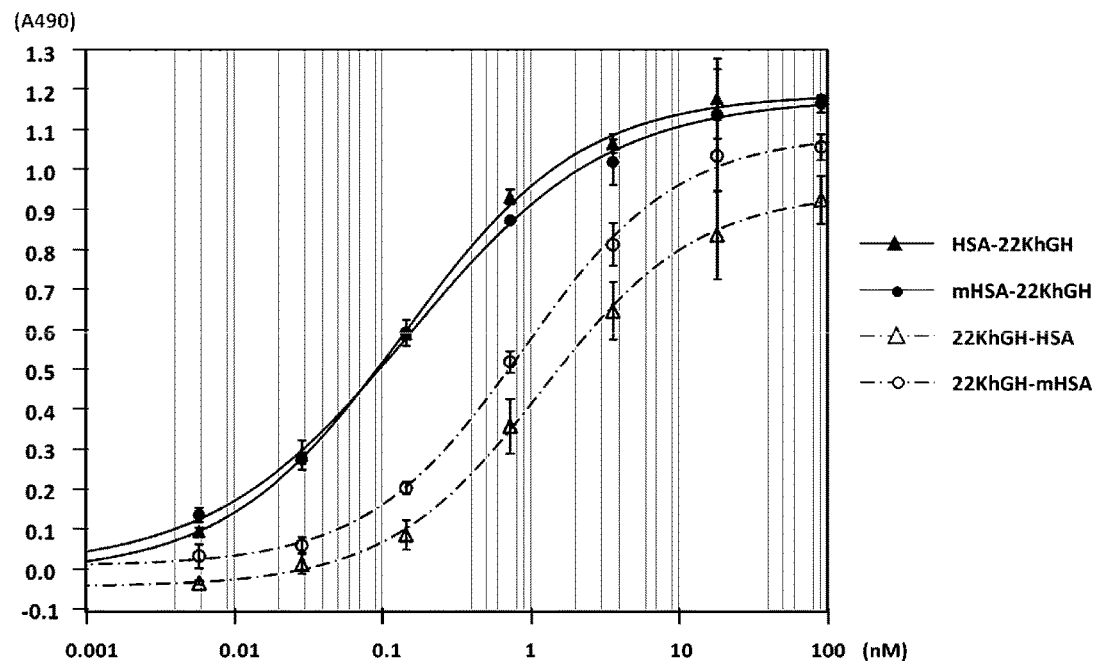
[Fig. 6]
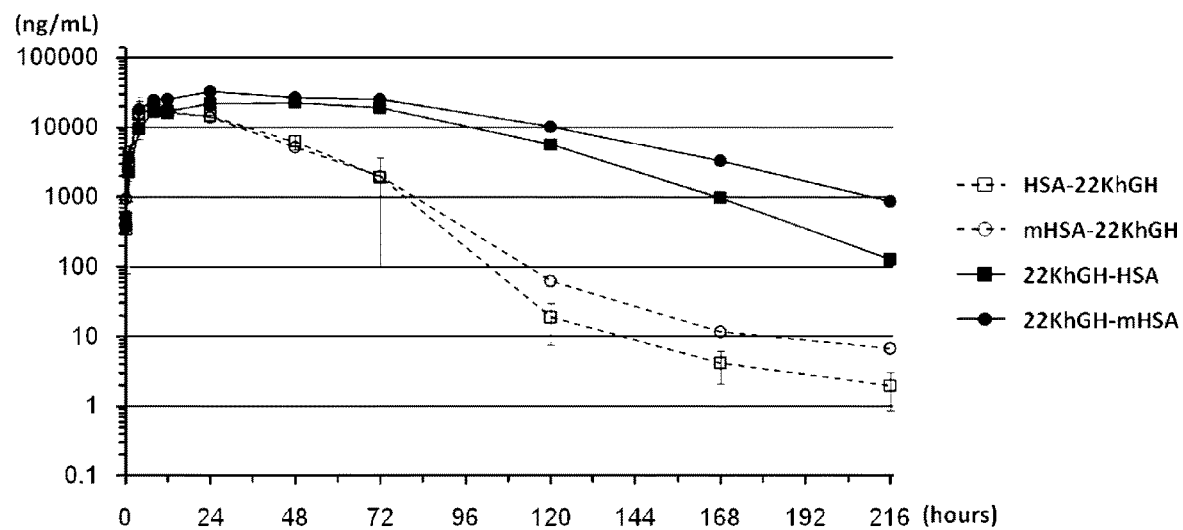

[Fig. 7]
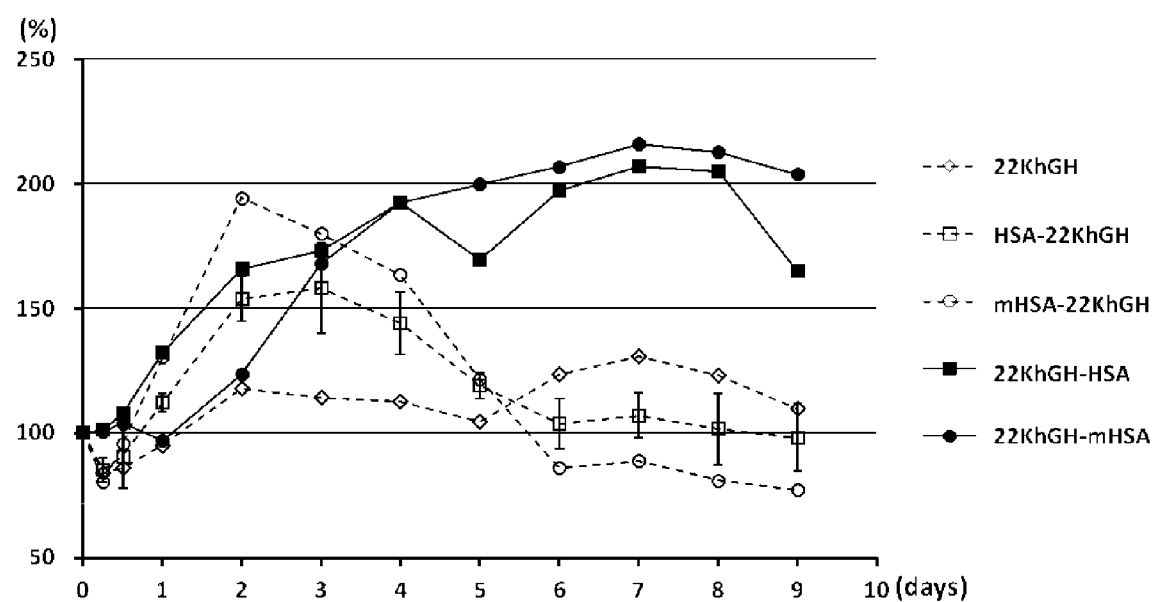

HUMAN SERUM ALBUMIN MUTANT

TECHNICAL FIELD

The present invention relates to a novel human serum albumin mutant that can be linked to a physiologically active protein to increase the stability of the protein in the blood, as well as to a human serum albumin mutant-linked protein (HSA mutant-linked protein) prepared by linking the human serum albumin mutant to a physiologically active protein, such as human serum albumin mutant-linked human growth hormone.

BACKGROUND ART

Human serum albumin (HSA) is a protein whose mature form consists of 585 amino acids. HSA is the most abundant component of plasma proteins, having a long half-life of 14-21 days in the plasma. HSA contributes to adjustment of osmotic pressure of the plasma, and functions to bind to, and carry, intrinsic compounds such as cations, fatty acids, hormones, bilirubin, and the like as well as extrinsic ones like medicines in the blood. In general, compounds bound to HSA become less likely to be absorbed by organs, and thus can circulate for a longer time in the blood.

Human serum albumin (HSA) is known to have plural natural variants. Human serum albumin Redhill is one of them (Non-patent documents 1 and 2). In comparison with the amino acid sequence of the common human serum albumin consisting of 585 amino acids as mentioned above, human serum albumin Redhill differs in that alanine as the 320th amino acid residue from the N-terminus is replaced with threonine, and that one arginine residue is added to the N-terminus, and it thus consists of 586 amino acids. This replacement of alanine with threonine give rise to a sequence Asn-Tyr-Thr within the amino acid sequence of albumin Redhill, and this Asn (asparagine) residue in that sequence receives N-glycosylation. Thus, the molecular weight of albumin Redhill is observed to be greater than the above common human serum albumin by approximately 2.5 kDa.

There is reported a method to increase the stability of a protein, such as an enzyme, in plasma by fusing HSA with the protein (Non-patent document 3, Patent documents 1 and 2). A fusion protein made of HSA and an enzyme or the like is provided in a medium or within cells as a recombinant protein, by culturing transformant cells produced by introducing an expression vector carrying a DNA in which a gene encoding HSA and a gene encoding a protein, e.g., an enzyme, are linked in frame.

Examples of proteins whose stability in plasma is increased by fusion with human serum albumin (HSA) include a fusion protein of HSA with G-CSF (Patent documents 1 and 3), a fusion protein of HSA with interferon α (Patent document 4), a fusion protein of HSA with GLP-1 (Patent document 5), a fusion protein of HSA with insulin (Patent document 6), a fusion protein of HSA with erythropoietin (Patent document 7), a fusion protein of HSA with growth hormone (Patent documents 4, 5 and 8-11), and the like.

Human growth hormone (hGH) is a protein secreted from the anterior pituitary under the control of hypothalamus. Human GH exhibits growth-promoting activities such as promotion of cartilage formation, promotion of protein anabolism, and the like, as well as improvement of body composition and lipid metabolism. Children with low hGH secretion exhibit growth hormone deficiency dwarfism, which is characterized by low height compared with normal children.

Pharmaceutical preparations (hGH preparation) containing hGH as the active principle, which is prepared as a recombinant protein utilizing E. coli cells with an introduced hGH gene and has molecular weight of approximately 22 kD, are clinically used widely as a therapeutic drug for growth hormone deficiency dwarfism, dwarfism in Turner syndrome, dwarfism in SGA (Small-for-Gestational Age), dwarfism by chronic renal failure, dwarfism in Prader-Willi syndrome, and dwarfism in achondroplasia, accompanied by no epiphyseal closure. After subcutaneous or intramuscular administration of an hGH preparation, it circulates in the blood, and its growth-promoting activity promotes growth of the patient. Preparations containing hGH are clinically used widely also as a therapeutic drug for adult growth hormone deficiency. Patients with adult growth hormone deficiency show various abnormalities such as abnormal lipid metabolism, and administration of hGH preparation will bring about improved QOL of the patients through, e.g., normalization of patients' lipid metabolism. Growject™, e.g., is available as an hGH preparation for growth hormone deficiency dwarfism and adult growth hormone deficiency.

Those attempts to improve stability of hGH in plasma were made in response to clinical needs. The half-life of hGH in plasma is regarded to be less than 20 minutes, and hGH administered to a patient thus quickly disappears from the blood. For hGH to exhibit its pharmacological activity in a patient, therefore, it must be administered to the patient either three times a week intramuscularly or everyday subcutaneously. Such frequent administration imposes a burden on patients. So, reduction of administration frequency, if achieved by increasing the stability of hGH in plasma and thereby elongating its half-life in plasma, would be desirable as leading to reduction of patients' burden.

PRIOR ART DOCUMENTS

Patent Documents

[Patent document 1] Patent application publication No. JP H07-503368
[Patent document 2] Patent application publication No. JP H03-178998
[Patent document 3] Patent application publication No. JP H07-503844
[Patent document 4] Patent application publication No. JP 2003-503838
[Patent document 5 Patent application publication No. JP 2005-514060
[Patent document 6] Patent application publication No. JP 2010-500031
[Patent document 7] Patent application publication No. JP 2011-015690
[Patent document 8] Patent application publication No. JP 2000-502901
[Patent document 9] Patent application publication No. JP 2008-518615
[Patent document 10] Patent application publication No. JP 2013-501036
[Patent document 11] Patent application publication No. JP 2013-518038

Non-Patent Documents

[Non-Patent Document 1] Brand S. et al., Clin Chim Acta. 136, 197-202 (1984)

[Non-Patent Document 2] Brennan S O. et al., Proc Natl Acad Sci USA. 87, 26-30 (1990)

[Non-Patent Document 3] Poznansky M J. et al., FEBS Letter. 239, 18-22 (1988)

SUMMARY OF INVENTION

Technical Problem

Against the above background, an objective of the present invention is to provide a novel human serum albumin mutant that can increase the stability of a desirable physiologically active protein (herein also called "protein (A)") in the blood when linked to the physiologically active protein. Another objective of the present invention is to provide a human serum albumin mutant-linked protein comprising a desirable protein (e.g., growth hormone) and the human serum albumin mutant linked thereto. Still another objective of the present invention is to provide a method to increase the stability of a desirable protein in the blood by linking the protein to the human serum albumin mutant.

Solution to Problem

As a result of repeated investigations in the study for the above-mentioned purposes, the inventors of the present invention found that a compound (human serum albumin mutant-linked hGH) that is obtained by linking human growth hormone (hGH) with a mutant (human serum albumin mutant) which consists of an amino acid sequence whose amino acid residue at position 320 from its N terminus is substituted by threonine instead of arginine occurring in the ordinary human serum albumin consisting of 585 amino acids, exhibits remarkably higher stability in the blood than the original human growth hormone when administered to a living body, and completed the present invention after further investigation. Thus, the present invention provides what follows.

1. A human serum albumin mutant comprising an amino acid sequence that, in comparison with the amino acid sequence set forth as SEQ ID NO:3, lacks not more than 10 amino acid residues and/or has not more than 10 amino acid residues replaced, with the proviso that the asparagine residue occurring at position 318 and the threonine at position 320 from the N-terminus of the amino acid sequence set forth as SEQ ID NO:3 are preserved and linked by peptide bonds via a single amino acid residue (X) except proline that is placed between those two amino acid residues.

2. The human serum albumin mutant according to 1 above, wherein the amino acid (X) is tyrosine.

3. The human serum albumin mutant according to 2 above consisting of the amino acid sequence set forth as SEQ ID NO:3.

4. A human serum albumin mutant that, in comparison with the amino acid sequence of the human serum albumin mutant according to one of 1-3 above, has not more than 10 amino acid added outside of the region corresponding to positions 318-320 from the N terminus of the amino acid sequence set for the as SEQ ID NO:3, and is not identical to the amino acid sequence set forth as SEQ ID NO:2

5. A human serum albumin mutant having not more than 10 amino acid residues added to the N or C terminus in comparison with the amino acid sequence of the human serum albumin mutant according to one of 1-3 above, and not identical to the amino acid sequence set forth as SEQ ID NO:2.

6. A human serum albumin mutant-linked protein (A) comprising a first polypeptide chain comprising the amino acid sequence of the human serum albumin mutant according to one of 1-5 above and a second polypeptide chain linked thereto comprising the amino acid sequence of another protein (A).

7. The human serum albumin mutant-linked protein (A) according to 6 above, wherein
(a) the C-terminus the second polypeptide chain is linked to the N-terminus of the first polypeptide chain or
(b) the N-terminus of the second polypeptide chain is linked to the C-terminus of the first polypeptide by one or more peptide bonds.

8. The human serum albumin mutant-linked protein according to 7 above, wherein the link via peptide bonds includes peptide bonds with a linker.

9. The human serum albumin mutant-linked protein (A) according to 8 above, wherein the linker consists of 1-50 amino acid residues.

10. The human serum albumin mutant-linked protein (A) according to 8 above, wherein the linker consists of 1-6 amino acid residues.

11. The human serum albumin mutant-linked protein (A) according to 8 above, wherein the linker is selected from the group consisting of Gly-Ser, Gly-Gly-Ser, and the amino acid sequences set forth as SEQ ID NO:4, SEQ ID NO:5 and SEQ ID NO:6.

12. The human serum albumin mutant-linked protein (A) according to 8 above, wherein the linker is represented by the amino acid sequence Gly-Ser.

13. The human serum albumin mutant-linked protein (A) according to one of 6-12 above, wherein the protein (A) exhibits a physiological activity when administered to a living body.

14. The human serum albumin mutant-linked protein (A) according to one of 6-13 above, wherein the protein (A) is selected from the group consisting of lysosomal enzymes including α-L-iduronidase, iduronate-2-sulfatase, glucocerebrosidase, β-galactosidase, GM2 activator protein, β-hexosaminidase A, β-hexosaminidase B, N-acetylglucosamin-1-phosphotransferase, α-mannosidase, β-mannosidase, galactosylceramidase, saposin C, arylsulfatase A, α-L-fucosidase, aspartylglucosaminidase, α-N-acetylgalactosaminidase, acid sphingomyelinase, α-galactosidase, β-glucuronidase, heparan sulfate N-sulfatase, α-N-acetylglucosaminidase, acetyl-CoA: α-glucosaminide N-acetyltransferase, N-acetylglucosamin-6-sulfate sulfatase, acid ceramidase, amylo-1,6-glucosidase, and CLN1 to 10, PD-1 ligands, bone morphogenetic protein (BMP), insulin, prolactin, motilin, adrenocorticotropic hormone (ACTH), melanocyte-stimulating hormone (MSH), thyrotropin-releasing hormone (TRH), thyroid stimulating hormone (TSH), luteinizing hormone (LH), follicle-stimulating hormone (FSH), parathyroid hormone (PTH), thrombopoietin, stem cell factor (SCF), leptin, vasopressin, oxytocin, calcitonin, glucagon, gastrin, secretin, pancreozymin, cholecystokinin, angiotensin, angiostatin, endostatin, human placental lactogen (HPL), human chorionic gonadotropin (HCG), enkephalin, endorphin, interferon α, interferon β, interferon γ, interleukin 2, thymopoietin, thymostimulin, thymus humoral factor (THF), serum thymic factor (FTS), thymosin, thymic factor X, tumor necrosis factor (TNF), granulocyte-colony stimulating factor (G-CSF), macrophage colony-stimulating factor (M-CSF), granulocyte macrophage colony-stimulating factor (GM-CSF), urokinase, tissue plasminogen activator (tPA), dynorphin, bombesin, neurotensin, caerulein, bradykinin, asparaginase, kallikrein, substance P, nerve growth factor (NGF), ciliary neurotrophic factor (CNTF), brain-derived neurotrophic factor (BDNF), glial cell derived neurotrophic factor (GDNF), neurotrophin 3, neurotrophin 4/5, neurotrophin 6, neuregulin 1, activin, basic fibroblast growth factor (bFGF), fibroblast growth factor 2 (FGF2), vascular endothelial growth factor (VEGF), bone morphogenetic protein (BMP), megakaryocyte growth and development factor (MGDF), blood coagulation factor VII, blood coagulation factor VIII, blood coagulation factor IX, superoxide dismutase (SOD), lysozyme chloride, polymyxin B, colistin, gramicidin, bacitracin, gastric inhibitory polypeptide (GIP), vasoactive intestinal peptide (VIP), platelet-derived growth factor (PDGF), growth hormone releasing factor (GRF), epidermal growth factor (EGF), erythropoietin, somatostatin, insulin-like growth factor 1 (IGF-1), 20K growth hormone, 22K growth hormone, and a salt or mutant of thereof.

15. The human serum albumin mutant-linked protein (A) according to one of 6-12 above, wherein the protein (A) is 22K growth hormone.

16. The human serum albumin mutant-linked protein (A) according to one of 6-12 above, wherein the protein (A) is 20K growth hormone.

17. The human serum albumin mutant-linked protein (A) according to 15 above consisting of the amino acid sequence set forth as SEQ ID NO:11.

18. The human serum albumin mutant-linked protein (A) according to 16 above consisting of the amino acid sequence set forth as SEQ ID NO:12.

19. A medicament comprising a human serum albumin mutant-linked protein (A) according to one of 6-18 above as the active principle.

20. The medicament comprising a human serum albumin mutant-linked protein (A) according to 19 above for the treatment of a disorder selected from the group consisting of growth hormone deficiency dwarfism, dwarfism in Turner syndrome, dwarfism by chronic renal failure, dwarfism in Prader-Willi syndrome, dwarfism in achondroplasia, and dwarfism in SGA, accompanied by no epiphyseal closure; and adult growth hormone deficiency, consumption caused by AIDS, and consumption caused by anorexia.

21. A DNA comprising a gene encoding the human serum albumin mutant according to one of 1-5 above.

22. A DNA comprising a gene encoding the human serum albumin mutant-linked protein (A) according to one of 6-18 above.

23. An expression vector comprising the DNA according to 21 or 22 above.

24. A mammalian cell transformed with the vector according to 23 above.

25. A human serum albumin mutant or human serum albumin mutant-linked protein (A) obtainable by culturing the mammalian cell according to 24 above in a serum-free medium.

Effects of Invention

The present invention enables increased stability in blood of a desirable physiologically active protein as a medicament to be administered to an animal (including human). Thus, it can enhance the pharmacological effects of the physiologically active protein and prolong the duration of pharmacological effect of the protein, too. Furthermore, it thereby makes it possible to lessen the dose or dosing frequency of the physiologically active protein, improve the QOL of the patients, and also contribute to prevention of infection and medical accident coming from conventional frequent dosing.

BRIEF DESCRIPTION OF DRAWINGS

FIG. 1 A flow diagram of the method for construction of pE-neo vector.

FIG. 2 A flow diagram of the method for construction of pE-hygr vector.

FIG. 3-1 A flow diagram of the method for construction of pE-IRES-GS-puro.

FIG. 3-2 A flow diagram of the method for construction of pE-IRES-GS-puro.

FIG. 3-3 A flow diagram of the method for construction of pE-IRES-GS-puro.

FIG. 3-4 A flow diagram of the method for construction of pE-IRES-GS-puro.

FIG. 3-5 A flow diagram of the method for construction of pE-IRES-GS-puro.

FIG. 3-6 A flow diagram of the method for construction of pE-IRES-GS-puro.

FIG. 3-7 A flow diagram of the method for construction of pE-IRES-GS-puro.

FIG. 3-8 A flow diagram of the method for construction of pE-IRES-GS-puro.

FIG. 3-9 A flow diagram of the method for construction of pE-IRES-GS-puro.

FIG. 4 A flow diagram of the method for construction of pE-mIRES-GS-puro.

FIG. 5 A figure showing the result of measurement of the activity of HSA-hGH fusion protein on cell growth activity using BaF3/hGHR cells. The vertical axis denotes absorbance at 490 nm, and the horizontal axis the concentration (nM) of each test sample. The vertical bars show standard deviation.

FIG. 6 A graph showing the result of pharmacodynamic analysis of HSA-hGH fusion protein using cynomolgus monkeys. The vertical axis denotes the concentration (ng/mL) of HSA-hGH fusion protein in cynomolgus monkeys' plasma, and the horizontal axis elapsed time (hr) after the administration of HSA-hGH fusion protein. The vertical bars in the graph show standard deviation.

FIG. 7 A graph showing the result of analysis of pharmacological effect of HSA-hGH fusion protein using cynomolgus monkeys. The vertical axis denotes the concentration (%) of IGF-1 in plasma of cynomolgus monkeys after administration of HSA-hGH fusion protein as compared to its concentration before the administration, and the horizontal axis denotes elapsed time (day) after the administration of HSA-hGH fusion protein. The vertical bars in the graph show standard deviation.

DESCRIPTION OF EMBODIMENTS

In the present invention, the term "human serum albumin" or "HSA" simply referred to does not only mean the ordinary wild-type human serum albumin consisting of 585 amino acid residues set forth as SEQ ID NO:1 but also includes without differentiation, such HSA mutants as correspond to those produced by substitution, deletion, and/or addition of one or more amino acid residues in, from, or to, the amino acid sequence set forth as SEQ ID NO:1 (in the specification, the term "addition" means one or more residues being added to a terminus of or within the sequence), so long as they still have such common functions of ordinary wild-type human serum albumin as binding to and carrying intrinsic compounds as well as extrinsic compounds, e.g., drugs, in the blood. When substituting some amino acid residues by different amino acid residues, the number of amino acid residues to be substituted is preferably 1-10, more preferably 1-5, and still more preferably 1-3. When deleting some amino acid residues, the number of amino acid residues to be deleted is preferably 1-10, more preferably 1-5, and still more preferably 1-3. A mutant, for example, consisting of 584 amino acid residues produced by deletion of one amino acid residue from the N or C terminus of the amino acid sequence set forth as SEQ ID NO:1 also is included in the meaning of human serum albumin. Further, a combination of such substitution and deletion of amino acids may also be made. Furthermore, one or more amino acid residues may be added to the ordinary wild-type HSA or its mutant, within those amino acid sequences or to their N or C terminus (the term "addition" means one or more residues being added to the terminus of or within a sequence). The number of amino acid residues herein added is preferably 1-10, more preferably 1-5, and still more preferably 1-3.

As a HSA mutant which contains a combination of at least two of the above three different types of mutation, i.e., substitution, deletion, and addition, preferred is one produced by deletion of 0-10 amino acid residues, substitution of 0-10 amino acid residues with other ones, and further addition of 0-10 amino acid residues. More preferably, the number of amino acid residues deleted, substituted and/or added from, in, or to, the amino acid sequence set forth as SEQ ID NO:1 is preferably not more than 5, and more preferably not more than 3, respectively.

In the present invention, the term "human serum albumin Redhill" (HSA-Redhill) means a variant of human serum albumin consisting of 586 amino acid residues set forth as SEQ ID NO:2. Compared to the wild-type human serum albumin consisting of 585 amino acid residues set forth as SEQ ID NO:1, human serum albumin Redhill has a sequence in which the amino acid at position 320 from the N terminus is not alanine but threonine, and one arginine residue is added to the N terminus. As a result of the substitution of alanine by threonine, albumin Redhill contains a partial amino acid sequence, Asn-Tyr-Thr, within its whole amino acid sequence, and the Asn (asparagine) residue in this partial sequence receives N-linked glycosylation. Thus, albumin Redhill is observed as having a molecular weight greater by 2.5 kD than the ordinary wild-type albumin (SEQ ID NO:1).

In the present invention, the term "human serum albumin mutant" (HSA mutant) means one of the above-mentioned mutants compared to the wild-type HSA (SEQ ID NO:1) except the variant (HSA Redhill) set forth as SEQ ID NO:2. Preferred HSA mutants in the present invention include one set forth as SEQ ID NO:3 as well as those having an amino acid sequence produced by substitution, deletion or addition of one or more amino acid residues as compared to the amino acid sequence set forth as SEQ ID NO:3, and in which the asparagine residue at position 318 and the threonine residue at position 320 from the N terminus of the amino acid sequence set forth as SEQ ID NO:3 are preserved being linked by peptide bonds via a single amino acid residue (X) except proline between those two, so long as they still have the function of the ordinary wild-type human serum albumin, i.e., binding to and carrying intrinsic compounds as well as extrinsic compounds, e.g., drugs, in the blood. When substituting some amino acid residues in the amino acid sequence by other ones, the number of amino acid residues to be substituted is preferably 1-10, more preferably 1-5, and still more preferably 1-3. When deleting some amino acid residues, the number of amino acid residues to be deleted is preferably 1-10, more preferably 1-5, and still more preferably 1-3. For example, a mutant may consist of 584 amino acid residues in which the amino acid residue at the N or C terminus of the amino acid sequence set forth as SEQ ID NO:3 is deleted. A combination of such substitution and deletion of amino acid residues is also allowed. Further, one or more amino acid residues may be added to those mutant within, or at the N or C terminus of, their amino acid sequences. Thus, in comparison to the amino acid sequence set forth as SEQ ID NO:3, the mutants may be those produced by a combination of at least two of the three types of mutation, i.e., substitution, deletion and addition, where deletion of 0-10 amino acid sequences, substitution of 0-10 amino acid residues by other ones, and addition of 0-10 amino acid residues have been made. Notwithstanding, the amino acids at positions 318-320 from the N terminus of the amino acid sequence set forth SEQ ID NO:3 must be asparagine-X-threonine ("X" is an amino acid residue except proline), and is preferably asparagine-tyrosine-threonine.

The positions and types (deletion, substitution, addition) of mutation in various HSA mutants of the present invention as compared to the ordinary wild-type HSA can be readily identified by alignment of the amino acid sequences of both HSAs.

The human serum albumin mutant prepared in the example of the present invention set forth below (a typical example of HSA mutant of the present invention) differs from the amino acid sequence of the ordinary wild-type human serum albumin consisting of 585 amino acids (SEQ ID NO:1) only in that the amino acid residue at position 320 from its N terminus is not alanine but threonine (SEQ ID NO:3). This difference gives rise to a partial sequence, Asn-Tyr-Thr, within the amino acid sequence of the HSA mutant [HSA(A320T)], and the Asn (asparagine residue) in the partial sequence can undergo N-linked glycosylation.

The HSA mutant of the present invention can be produced as a recombinant protein, by preparing an expression vector in which a DNA encoding the HSA mutant of the present invention is incorporated, and culturing host cells transformed with the expression vector.

In the present invention, a counterpart physiologically active protein (referred to also as "protein (A)") in the specification) to be linked to the human serum albumin mutant is any protein except serum albumin (whether it is a mutant or not) having a physiological activity. The term "physiological activity" is an ability of acting on a living body to cause some specific physiological change. Examples include those proteins involved in different physiological regulations (stimulation, suppression), such as various enzymes (e.g., lysosomal enzymes), peptide hormones (protein hormones), neurotransmitters, growth factors, signal transduction factors, etc.

In the present invention, the term "human serum albumin mutant-linked protein (A)" or "HSA mutant-linked protein (A)" means a protein (A) to which the HSA mutant of the present invention is linked, a compound obtained by linking the polypeptides having the amino acid sequence of one of the two, respectively. The phrase "to "link" those polypeptides" not only means that the N terminus of the one is directly bonded to the C terminus of the other by a peptide bond, but also includes bonding of them indirectly via a linker.

Herein, the term "linker" is a structural portion that is placed between the above two polypeptides and links them by covalent bonds, and is not one derived from the termini either of the HSA mutant of the present invention or of its counterpart protein (A). A linker may be a single amino acid residue or a peptide chain portion consisting of two or more amino acid residues forming peptide bonds with both of the polypeptides (peptide linker). Any of such linkers consisting of one or more amino acids are referred to comprehensively as a "peptide linker" in the present specification. In the present invention, a linker also may be a structural portion that is a divalent group not belonging to a peptide linker but linking the HSA mutant and a protein (A) between them by covalent bonds. They are referred to as a "non-peptide linker" in the specification. Further, in the present specification, the expression stating that a HSA mutant and a protein (A) are linked "via peptide bonds" includes a case where the both are linked directly by a peptide bond and a case where the both are linked via a peptide linker. Furthermore, in the case where the HSA mutant and a protein (A) is bonded together directly or via a peptide linker, the compound "HSA mutant-linked protein (A)" is also referred to as "HSA mutant-fused protein (A)".

Where the HSA mutant of the present invention and a protein (A) are linked via a peptide linker, the linker consists of preferably 1-50, more preferably 1-17, still preferably 1-10, still more preferably 1-6 amino acid residues, and, for example, 2-17, 2-10, 10-40, 20-34, 23-31, or 25-29 amino acids, and further, one single amino acid residue, or 2, 3, 5, 6 or 20 amino acid residues. So long as the HSA mutant portion linked by the peptide linker retains the HSA's function and the protein (A) portion can exhibit its physiological activity of the protein (A) in a physiological environment, there is no limitation as to an amino acid or amino acid sequence forming the peptide linker, while it is preferably composed of glycine and serine. Preferable examples of a peptide linker include those consisting of Gly-Ser, Gly-Gly-Ser, Gly-Gly-Gly-Gly-Ser (SEQ ID NO:4), Gly-Gly-Gly-Gly-Gly-Ser (SEQ ID NO:5), Ser-Gly-Gly-Gly-Gly-Gly (SEQ ID NO:6), and linkers comprising some these amino acid sequences. A sequence comprising 2-10 or 2-5 consecutively linked copies of any one of those amino acid sequences may be employed as a peptide linker, and a sequence comprising 1-10 or 2-5 consecutively linked copies of any combination of two or more of these amino acid sequencers may also be employed as a peptide linker. Examples of preferred peptide linkers comprising a combination of two or more of those amino acids include amino acid sequence comprising 20 amino acids in total consisting of an amino acid sequence Gly-Ser followed by three consecutively linked copies of an amino acid sequence Gly-Gly-Gly-Gly-Gly-Ser (SEQ ID NO:5).

As a method for linking two different polypeptides, there is known a common method, for example, in which an expression vector is prepared having an incorporated DNA produced by linking, downstream of the gene encoding one of the polypeptides, the gene encoding the other polypeptide in-frame, and host cells transformed with this expression vector are cultured to let them express the recombinant fusion protein. Such a method can be used for the present invention.

In the case where HSA mutant-fused protein (A) is produced as a recombinant protein by transformant cells, a fusion protein is obtained in which a polypeptide comprising the amino acid sequence of protein (A) is linked to the N or C terminus of a polypeptide comprising the amino acid sequence of an HSA mutant.

In the case where a polypeptide comprising an amino acid sequence of protein (A) is linked to the N terminus of a polypeptide comprising the amino acid sequence of an HSA mutant, an expression vector is employed having an incorporated DNA in which the gene encoding the amino acid sequence of the HSA mutant is linked in-frame downstream of the gene encoding the amino acid sequence of protein (A). Where the two polypeptides are linked indirectly via a peptide linker, the DNA encoding the linker is inserted in-frame between the genes encoding the respective two proteins.

In the case where a polypeptide comprising the amino acid sequence of protein (A) is linked to the C terminus of a polypeptide comprising the amino acid sequence an HSA mutant, an expression vector is employed having an incorporated DNA in which the gene encoding the amino acid sequence of the HSA mutant is linked in-frame upstream of the gene encoding the amino acid sequence of protein (A). Where the two polypeptides are linked indirectly via a peptide linker, the DNA encoding the linker is inserted in-frame between the genes encoding the respective two proteins.

To let host cells produce the HSA mutant or a HSA mutant-fused protein (A), an expression vector having an incorporated DNA encoding either of them is introduced into the host cells. So long as they can produce the HSA mutant or a HSA mutant-fused protein (A) of the present invention through introduction of such an expression vector, there is no notable limitation as to host cells that may be employed for this purpose, and thus they may be either eukaryotic cells such as mammalian cells, yeast, plant cells, and insect cells or prokaryotic cells such as E. coli, Bacillus subtilis, among which particularly preferred are mammalian cells. For a protein (A) to be expressed in a glycosylated form, host cells are selected from the groups consisting of eukaryotic cells such as mammalian cells, yeast, plant cells, and insect cells. The Asn residue in the partial sequence Asn-Tyr-Thr that arises by replacement of the amino acid residue at position 320 of the ordinary wild-type HSA with threonine, or the Asn residue in a partial sequencer Asn-X-Thr ("X" is an amino acid sequence other than proline), undergoes N-linked glycosylation by employing eukaryotic cells for expression of HSA mutant-fused protein (A).

Though there is no notable limitation as to the species of mammalian cells to be employed as host cells, preferred are cells derived from human, mouse, and Chinese hamster, among which CHO cells, which are derived from Chinese hamster ovary cells, or NS/O cells, which are derived from mouse myeloma are particularly preferred. So long as it will lead to expression of the gene in mammalian cells into which it is introduced, there is no notable limitation as to an expression vector employed in which a DNA fragment encoding the HSA mutant or a HSA mutant-fused protein (A) of the present invention is incorporated for expression. The gene introduced into an expression vector is placed downstream of a DNA sequence that regulates the frequency of transcription of the gene in mammalian cells (gene expression regulatory site). Examples of a gene expression regulatory site which can be employed in the present invention include a Cytomegalovirus-derived promoter, SV40 early promoter, human elongation factor-1α (EF-1α) promoter, and human ubiquitin C promoter.

While mammalian cells having such an introduced expression vector come to produce the protein incorporated in the expression vector, the amount of its expression will vary cell by cell and will not be uniform. For efficient production of the HSA mutant, or an HSA mutant-fused protein (A), of the present invention, therefore, a step is required in which the cells exhibiting high expression level are selected from the mammalian cells having the introduced expression vector. For carrying out such a selection step, a gene acting as a selection marker is introduced in the expression vector.

The most common of such selection markers are enzymes that decompose drugs such as puromycin and neomycin (drug resistance marker). In general, mammalian cells will be killed by one of those drugs that is present beyond certain concentrations. Since cells having an introduced expression vector in which a drug resistance gene is incorporated can decompose the drug with the expressed drug resistance gene to detoxify it or attenuate its toxicity, they can survive even in the presence of such drugs. By introducing into mammalian cells of an expression vector having an incorporated drug resistance gene as a selection marker, and then culturing the cells in a medium with a gradually increasing concentration of the drug corresponding to the drug resistance marker, such cells can be obtained that are able to grow even in the presence of higher concentrations of the drug. In cells selected in this manner, generally, expression levels of the gene encoding that protein of interest incorporated in the expression vector are also elevated along with those of the drug resistance marker, and as a result those cells are selected which express the protein at high levels.

Further, glutamine synthetase (GS) can also be used as a selection marker. Glutamine synthetase is an enzyme which synthesizes glutamine from glutamic acid and ammonia. Generally, if mammalian cells are cultured in a medium which contains an inhibitor of glutamine synthetase, e.g., methionine sulfoximine (MSX), yet no glutamine, the cells will be annihilated. However, if mammalian cells have an introduced expression vector in which glutamine synthetase is incorporated as a selection marker, the cells become able to grow even in the presence of higher concentrations of MSX because of their increased levels of glutamine synthetase expression. Here, if culture is continued with gradually increasing concentration of MSX, such cells are obtained that can grow even in the presence of still higher concentrations of MSX. Generally, in cells selected by this way, expression levels of the gene encoding that protein of interest incorporated in the expression vector are also elevated along with those of the drug resistance marker, and as a result those cells are selected which express the protein at high levels.

Dihydrofolate reductase (DHFR) can also be used as a selection marker. In the case where DHFR is employed as a selection marker, mammalian cells having the introduced expression vector is cultured in a selection medium containing a DHFR inhibitor such as methotrexate or aminopterin. Culture continued with gradually increasing concentration of a DHFR inhibitor give rise to such cells that can grow even in the presence of higher concentrations of the DHFR inhibitor. Generally, in cells selected in this manner, expression levels of the gene encoding that protein of interest incorporated in the expression vector are also elevated along with those of DHFR, and as a result those cells are selected which express the protein at high levels.

Expression vector are known in which glutamine synthetase (GS) is placed as a selection marker downstream of the gene encoding a protein of interest via an internal ribosome entry site (IRES) (WO 2012/063799, WO 2013/161958). The expression vectors described in these documents may be used particularly preferably in producing the HSA mutant or HSA mutant-fused protein (A) of the present invention.

For example, an expression vector for expression of a protein of interest which comprises a first gene expression regulatory site, a gene encoding the protein downstream thereof, an internal ribosome entry site further downstream thereof, and a gene encoding glutamine synthetase still further downstream thereof, and further comprises dihydrofolate reductase gene or a drug resistance gene either downstream of the first gene regulatory site or downstream of a different, second gene expression regulatory site, can be preferably used in producing the HSA mutant or a HSA mutant-fused protein (A) of the present invention. In this vector, a cytomegalovirus-derived promoter, SV40 early promoter, and human elongation factor-1α promoter (hEF-1α promoter), and human ubiquitin C promoter are preferably used as the first gene expression regulatory site or the second gene expression regulatory site, among which hEF-1α promoter is particularly preferred.

Further, as an internal ribosome entry site, preferably used is one of those derived from the 5' untranslated region of the genome of a virus selected from the group consisting of a virus of Picornaviridae, Picornaviridae Aphthovirus, hepatitis A virus, hepatitis C virus, coronavirus, bovine enterovirus, Theiler's murine encephalomyelitis virus, Coxsackie B virus, or of a gene selected from the group consisting of human immunoglobulin heavy chain binding protein gene, *Drosophila antennapedia* gene, and *Drosophila ultrabithorax* gene, among which particularly preferable is the internal ribosome entry site derived from the 5' untranslated region of mouse encephalomyocarditis virus. In the case where the 5' untranslated region of the genome of mouse encephalomyocarditis virus is used, not only its wild-type but also those in which some of the plural start codons included in the wile-type internal ribosome entry sites are destroyed can preferably be employed. The drug resistance gene employed in the expression vector of the present invention is preferably puromycin or neomycin resistance gene, and more preferably puromycin resistance gene.

Furthermore, for example, an expression vector for expression of a protein of interest which comprises human elongation factor-1α promoter, a gene encoding the protein downstream thereof, and an internal ribosome entry site derived from the 5' untranslated region of the genome of mouse encephalomyocarditis virus further downstream thereof, and further comprises another gene expression regulatory site and dihydrofolate reductase gene downstream thereof, wherein the internal ribosome entry site is one in which some of the plural start codons included in the wile-type internal ribosome entry sites are destroyed, can preferably be employed in producing the HSA mutant or an HSA mutant-fused protein (A) of the present invention. An example of such a vector is one described in WO 2013/161958.

Still further, for example, an expression vector for expression of a protein of interest which comprises human elongation factor-1α promoter, a gene encoding the protein downstream thereof, an internal ribosome entry site derived from the 5' untranslated region of the genome of mouse encephalomyocarditis virus further downstream thereof, and a gene encoding glutamine synthetase still further downstream thereof, and further comprises another gene expression regulatory site and a drug resistance gene downstream thereof, wherein the internal ribosome entry site is one in which some of the plural start codons included in the wile-type internal ribosome entry sites are destroyed, can preferably be employed in producing the HSA mutant or an HSA mutant-fused protein (A). Examples of such a vector are pE-mIRES-GS-puro described in WO 2012/063799 and pE-mIRES-GS-mNeo described in WO 2013/161958.

There are three start codons (ATG) at the 3' end of the internal ribosome entry site derived from the 5' untranslated region of the wild-type genome of mouse encephalomyocarditis virus. The partial sequences containing those three start codons is shown as SEQ ID NO:7 (5'-ATGataatATGgc-cacaaccATG-3': the start codon ATG is shown in upper case letters). An example in which one of the start codons in this sequence is destroyed is one set forth as SEQ ID NO:8 (5'-atgataagcttgccacaaccatg-3'), and pE-mIRES-GS-puro and pE-mIRES-GS-mNeo above mentioned are expression vectors having IRES comprising the sequence set forth as SEQ ID NO:8.

In the present invention, mammalian cells having an introduced expression vector in which a DNA fragment encoding the HSA mutant or an HSA mutant-fused protein (A) of the present invention are subjected to selective culture in a selection medium to select cells showing high levels of their expression.

In the case where DHFR is used as a selection marker in selective culture, the concentration of a DHFR inhibitor in the selection medium is increased stepwise. The maximum concentration of it, where the DHFR inhibitor is methotrexate, is preferably 0.25-5 µM, more preferably 0.5-1.5 µM, and still more preferably about 1.0 µM.

In the case where GS is employed as the selection marker, the concentration of a GS inhibitor in the selection medium is increased stepwise. The maximum concentration of it, where the GS inhibitor is MSX, is preferably 100-1000 µM, more preferably 200-500 µM, and still more preferably about 300 µM. As a selection medium, a medium containing no glutamine is generally employed here.

In the case where an enzyme that decomposes puromycin is employed as a selection marker, the maximum concentration of puromycin in the selection medium is preferably 3-30 µg/mL, more preferably 5-20 µg/mL, and still more preferably about 10 µg/mL.

In the case where an enzyme that decomposes neomycin is employed as a selection marker, the maximum concentration of G418 in the selection medium is preferably 0.1-2 mg/mL, more preferably 0.5-1.5 mg/mL, and still more preferably about 1 mg/mL.

As a medium for culturing mammalian cells, either for selection culture or for production of the recombinant protein mentioned below (recombinant protein production medium), any medium may be used without notable limitation so long as it allows cultivation of mammalian cells to let them grow in it, and among them a serum-free medium is preferably employed. Because HSA has a property to adsorb components contained in the blood, if HSA is produced using a serum-containing medium, the HSA thus obtained would contain adsorbed blood-derived impurities, which would have to be removed in the following steps.

The HSA mutant or a HSA mutant-fused protein (A) of the present invention is obtained, in particular, by culturing cells that express either of them, in a serum-free medium. As employment of a serum free medium enables reduction of the amount of impurities adsorbed by HSA, it allows simplification of subsequent purification steps.

The cells selected by selection culture showing high levels of expression of the recombinant protein (recombinant protein producing cells) are employed in the production of the recombinant protein. Production of the recombinant protein is performed by culturing the recombinant protein producing cells in a medium for recombinant protein production. This culture is called production culture.

In the present invention, as a serum-free medium employed for recombinant protein production, a medium is preferably used that contains, e.g., 3-700 mg/L of amino acids, 0.001-50 mg/L of vitamins, 0.3-10 g/L of monosaccharides, 0.1-10000 mg/L inorganic salts, 0.001-0.1 mg/L of trace elements, 0.1-50 mg/L of nucleosides, 0.001-10 mg/L of fatty acids, 0.01-1 mg/L of biotin, 0.1-20 µg/L of hydrocortisone, 0.1-20 mg/L of insulin, 0.1-10 mg/L of vitamin B12, 0.01-1 mg/L of putrescine, 10-500 mg/L of sodium pyruvate, and water soluble iron compounds. Thymidine, hypoxanthine, a conventional pH indicator and antibiotics may also be added to the medium.

As a serum-free medium for recombinant protein production, DMEM/F12 medium (mixture medium of DMEM and F12), well known to a skilled artisan, may be used as a base medium. Furthermore, as a serum-free medium, DMEM (HG)HAM modified (R5) medium may also be used, which contains sodium bicarbonate, L-glutamine, D-glucose, insulin, sodium selenite, diaminobutane, hydrocortisone, iron(II) sulfate, asparagine, aspartic acid, serine, and polyvinylalcohol. Further, commercially available serum-free mediums, such as CD OptiCHO™ medium, CHO-S-SFM II medium, or CD CHO medium (Thermo Fisher Scientific, formerly Life Technologies), IS cho-V™ medium (Irvine Scientific), EX-CELL™ 302 medium, or EX-CELL™ 325-PF medium (SAFC Biosciences), may be used, too, as a base medium.

To obtain an HSA mutant-fused protein (A), a method also may be employed in which both of the protein moieties are separately prepared, and their polypeptides then are linked via a non-peptide linker or a peptide linker. Examples of non-peptide linker that may be used include polyethylene glycol (PEG), polypropylene glycol, co-polymers of ethylene glycol and propylene glycol, polyethers, polyvinylalcohol, polysaccharides, dextran, polyvinylether, biodegradable polymers, lipid polymers, chitins, and hyaluronic acid, or derivatives thereof, or combinations thereof. A peptide linker is a peptide chain or its derivative composed of peptide bonded 1-50 amino acids, whose N and C termini are respectively peptide bonded either to the HSA mutant of the present invention or a protein of interest to link the HSA mutant of the present invention and the protein of interest.

A protein (A) linked with the HSA mutant of the present invention using PEG as a non-peptide linker is, where specifically identified, referred to as an HSA mutant PEG-linked protein (A). An HSA mutant PEG-linked protein (A) can be produced either by bonding the HSA mutant and PEG (PEGylated HSA mutant), and then bonding a protein (A) thereto or by bonding a protein (A) and PEG (PEGylated physiologically active protein (A)) at first, and then bonding the HSA mutant thereto. To bond PEG to the HSA mutant or a protein (A), such a PEG is used that is modified with functional groups such as carbonate, carbonyldiimidazole, an active ester of carbonic acid, azlactone, cyclic imide thione, isocyanate, isothiocyanate, imidate, or aldehyde. The HSA mutant of the present invention and a protein (A) are covalently bonded mainly through the reaction of one of those functional groups introduced into PEG with the amino group on the HSA mutant of the present invention and protein (A). Though there is no notable limitation as to the molecular weight of PEG employed here, its mean molecular weight (MW) is as follows: preferably MW=500-60000, and more preferably 500-20000. For example, PEG having mean molecular weight of about 300, about 500, about 1000, about 2000, about 4000, about 10000, or about 20000, and the like, can be preferably used as a non-peptide linker.

For example, a PEGylated HSA mutant can be obtained by mixing the HSA mutant of the present invention with polyethylene glycol having aldehyde groups as functional groups (ALD-PEG-ALD) at their molar ratio HSA/(ALD- PEG-ALD) of 11, 12.5, 15, 110, 120, or the like, and adding a reducing agent such as NaCNBH₃ to the mixture and allowing them to react. Then, by reacting the PEGylated HSA mutant with the protein (A) in the presence of a reducing agent like NaCNBH₃, a HSA mutant PEG-linked protein is obtained. Contrarily, a HSA mutant PEG-linked protein (A) of the present invention can also be obtained by bonding the protein (A) with ALD-PEG-ALD at first to prepare a PEGylated protein (A), and then bonding thereto the HSA mutant of the present invention.

A protein (A) to be linked to the HSA mutant of the present invention is preferably one of such proteins that exhibit some physiological activities when administered to a living body, and they may be chosen as desired. Examples of such proteins include, but is not limited to, α-L-iduronidase, iduronate-2-sulfatase, glucocerebrosidase, β-galactosidase, GM2 activator protein, β-hexosaminidase A, β-hexosaminidase B, N-acetylglucosamin-1-phosphotransferase, α-mannosidase, β-mannosidase, galactosylceramidase, saposin C, arylsulfatase A, α-L-fucosidase, aspartylglucosaminidase, α-N-acetylgalactosaminidase, acid sphingomyelinase, α-galactosidase, β-glucuronidase, heparan sulfate N-sulfatase, α-N-acetylglucosaminidase, acetyl-CoA: α-glucosaminide N-acetyltransferase, N-acetylglucosamin-6-sulfate sulfatase, acid ceramidase, amylo-1,6-glucosidase, lysosomal enzymes including CLN1-10, PD-1 ligands, bone morphogenetic protein (BMP), insulin, prolactin, motilin, adrenocorticotropic hormone (ACTH), melanocyte-stimulating hormone (MSH), thyrotropin-releasing hormone (TRH), thyroid stimulating hormone (TSH), luteinizing hormone (LH), follicle-stimulating hormone (FSH), parathyroid hormone (PTH), thrombopoietin, stem cell factor (SCF), leptin, vasopressin, oxytocin, calcitonin, glucagon, gastrin, secretin, pancreozymin, cholecystokinin, angiotensin, angiostatin, endostatin, human placental lactogen (HPL), human chorionic gonadotropin (HCG), enkephalin, endorphin, interferon α, interferon β, interferon γ, interleukin 2, thymopoietin, thymostimulin, thymus humoral factor (THF), serum thymic factor (FTS), thymosin, thymic factor X, tumor necrosis factor (TNF), granulocyte-colony stimulating factor (G-CSF), macrophage colony-stimulating factor (M-CSF), granulocyte macrophage colony-stimulating factor (GM-CSF), urokinase, tissue plasminogen activator (tPA), dynorphin, bombesin, neurotensin, caerulein, bradykinin, asparaginase, kallikrein, substance P, nerve growth factor (NGF), ciliary neurotrophic factor (CNTF), brain-derived neurotrophic factor (BDNF), glial cell derived neurotrophic factor (GDNF), neurotrophin 3, neurotrophin 4/5, neurotrophin 6, neuregulin 1, activin, basic fibroblast growth factor (bFGF), fibroblast growth factor 2 (FGF2), vascular endothelial growth factor (VEGF), bone morphogenetic protein (BMP), megakaryocyte growth and development factor (MGDF), blood coagulation factor VII, blood coagulation factor VIII, blood coagulation factor IX, superoxide dismutase (SOD), tissue plasminogen activator (TPA), lysozyme chloride, polymyxin B, colistin, gramicidin, bacitracin, gastric inhibitory polypeptide (GIP), vasoactive intestinal peptide (VIP), platelet-derived growth factor (PDGF), growth hormone releasing factor (GRF), epidermal growth factor (EGF), erythropoietin, somatostatin, insulin-like growth factor 1 (IGF-1), 20K growth hormone, 22K growth hormone, and a salt or a mutant of them.

In the present invention, though there is no notable limitation as to the biological species from which a protein (A) to be linked to the HSA mutant originates, preferred are those originating from mammals, more preferably proteins originating from primates including human, African green monkey, rodents including mouse, rat, Chinese hamster, rabbit, dog, and more preferably proteins originating from human.

In the present invention, it is not necessary that a protein (A) is a wild-type protein. Namely, it may be a such mutant, with one or more amino acids substituted, deleted, and/or added as compared to the wild-type amino acid sequence, yet retaining the physiological activities of the original protein (A), or even acting as an antagonist to the wild-type protein (A) (thus exerting an influence on the activity of intrinsic protein (A)). The number of amino acids substituted, deleted, and/or added may be preferably 1-10, more preferably 1-5, and still more preferably 1-3, for each type of mutation. Such substitution, deletion, and/or addition may take place in combination.

The HSA mutant-linked protein (A) of the present invention has increased stability and thus a longer half-life in the blood than the original protein (A) with no linked HSA mutant. Though the half-life of it would vary depending on the route of administration and dose employed, it becomes very stable in the blood, as demonstrated by its half-life in the blood ($t_{1/2}\beta$) that is longer than about 5 hours after subcutaneous administration to cynomolgus monkeys. For example, the half-life in the blood ($t_{1/2}\beta$) of the HSA mutant-linked human growth hormone of the present invention is 5-40 hours after its single subcutaneous administration to male cynomolgus monkeys at a dose of 0.5-10 mg/kg.

The HSA mutant-linked protein (A) of the present invention can be used as a medicament utilizing the activity exhibited by the protein (A) moiety when administered to a living body. The term "living body" means a living body of mammals including human, and most preferably a human.

The HSA mutant-linked protein (A) of the present invention has increased stability in the blood. Therefore, even a protein (A) which is so unstable in the blood and rapidly decomposed after administration that could not exhibit a sufficient effect so far, can now be stabilized in the blood and allowed to exhibit its physiological activity, by linking it to the HSA mutant of the present invention, which gives rise to a possibility of its development as a medicament.

Even a protein (A) that could so far have been used as a medicament can be further improved in its stability in the blood by linking it to the HSA mutant of the present invention and thus can remain in the blood for a longer period of time, with its physiological activity maintained. This enables reduction of dosing frequency or the dose of the protein (A) itself. For example, the dosing frequency of a medicament which requires daily administration could be reduced to, e.g., once in 3-30 days by linking it to the HSA mutant of the present invention. Furthermore, the dose of the medicament could be reduced to 1/3-1/100, for example.

A medicament comprising the HSA mutant-linked protein (A) as the active principle can be administered intravenously, intramuscularly, intraperitoneally, or subcutaneously in the form of injection. The route of administration of the medicament may be chosen as desired, in accordance with its preparation form, disorders to be treated, and the like. Preparations for those injection routes may be supplied as lyophilized preparations or aqueous liquid ones. Such aqueous liquid preparations may be supplied in the form of vials containing it, or in a pre-filled type, where it has already been filled in syringes. Lyophilized preparations are reconstituted by dissolving them in an aqueous medium before use, and then administered.

Human growth hormone is one of those proteins (A) to be linked to the HSA mutant of the present invention. Human growth hormone includes two main types which differ from each other in their molecular weight, i.e., 22K human growth hormone and 20K human growth hormone. The 22K growth hormone is a protein consisting of 191 amino acids and having the amino acid sequence set forth as SEQ ID NO:9. Though the term "human growth hormone (or hGH)" generally means this 22K growth hormone, this term "human growth hormone (or hGH)" simply referred to in the present specification includes both the 22K human growth hormone and the 20K human growth hormone.

The term "22K human growth hormone (or "22K hGH)" simply referred to in the present specification includes, in addition to the wild-type 22K hGH having the amino acid sequence set forth as SEQ ID NO:9, such 22K hGH mutants having one or more amino acids substituted, deleted, and/or added as compared to the wild-type and yet having growth-promoting activity. The number of amino acids that may be substituted, deleted, and/or added is preferably 1-8, more preferably 1-4, and still more preferably 1-2, for each mutation type.

The wild-type 20K growth hormone is equivalent to the resultant of deletion of 15 amino acids at positions 32-46 from the N terminus of the 191 amino acids that forms the wild-type 22K growth hormone (SEQ ID NO:9), namely, a protein with growth-promoting activity consisting of an amino acid sequence (SEQ ID NO:10) that is composed of 176 amino acids. It should be noted that in the present specification, the term "20K human growth hormone (or 20K hGH)" simply referred to in the present specification includes, in addition to the wild-type 20K hGH set forth as SEQ ID NO:10, such 20K hGH mutants that correspond to those having one or more amino acids substituted, deleted, and/or added as compared to that sequence and yet having growth-promoting activity. The number of amino acids that may be substituted, deleted, and/or added is preferably 1-8, more preferably 1-4, and still more preferably 1-2, for each mutation type.

Pharmaceutical preparations (hGH preparations) containing hGH having the molecular weight of about 22KD as the active principle, which are produced as a recombinant protein using *E. coli* cells having introduced hGH gene, are widely used clinically as therapeutic preparations for growth hormone deficiency dwarfism, dwarfism in Turner syndrome, dwarfism in SGA accompanied by no epiphyseal closure, dwarfism by chronic renal failure, dwarfism in Prader-Willi syndrome, and dwarfism in achondroplasia. Those hGH preparations are subcutaneously or intramuscularly administered, and their ingredient, hGH, circulating in the blood, exhibits its effect to promote patient's growth by its growth-promoting activity. At the same time, the hGH preparations are also widely used clinically as therapeutic preparations for adult growth hormone deficiency. While abnormal lipid metabolism is observed in patients with adult growth hormone deficiency, administration of hGH normalizes patient's lipid metabolism and improves their QOL. Human GH is also applied clinically as a therapeutic drug for consumption caused by AIDS. Growject (trademark) is an example of hGH preparation for the treatment of growth hormone deficiency dwarfism, adult growth hormone deficiency, and the like.

In the present invention, the product in which human growth hormone is employed as the protein (A) linked to human serum albumin mutant (mHSA) is referred to as "human serum albumin mutant-linked human growth hormone", "mHSA-linked hGH", or the like, and where the linkage is made by a peptide bond, specifically also as "human serum albumin mutant-fused human growth hormone", "mHSA-fused hGH", or the like.

More specifically, to link a polypeptide comprising the amino acid sequence of the HSA mutant with a polypeptide comprising the amino acid sequence of hGH, a general method may be employed in the present invention, in which, for example, an expression vector prepared having an incorporated DNA fragment in which the gene encoding one of the polypeptides is linked downstream thereof in-frame to the gene encoding the other polypeptide, and host cells transformed with this expression vector are cultured to let the recombinant protein to express itself.

By preparing an mHSA-linked hGH using a method to let transformed cells express it as a recombinant protein, a polypeptide comprising the amino acid sequence of hGH is linked to the N or C terminus of the polypeptide comprising the amino acid sequence of the HSA mutant of the present invention, either directly or indirectly via a linker.

In the case where a polypeptide comprising the amino acid of hGH is linked to the N terminus of a polypeptide comprising the amino acid sequence of the HSA mutant of the present invention, an expression vector is employed having an incorporated DNA fragment in which the gene encoding a polypeptide comprising the amino acid sequence of the HSA mutant of the present invention is linked in-frame to, and downstream of, the gene encoding a polypeptide comprising the amino acid sequence of hGH. In the case where the two polypeptides are indirectly linked via a peptide linker, a DNA sequence encoding the linker is placed in-frame between the genes encoding the two polypeptides.

In the case where a polypeptide comprising the amino acid sequence of hGH is linked to the C terminus of a polypeptide comprising the amino acid sequence of the HSA mutant of the present invention, an expression vector is employed having an incorporated DNA fragment in which the gene encoding a polypeptide comprising the amino acid sequence of the HSA mutant of the present invention is linked in-frame to, and upstream of, the gene encoding a polypeptide comprising the amino acid sequence of hGH. In the case where the two polypeptides are indirectly linked via a peptide linker, a DNA sequence encoding the linker is placed in-frame between the genes encoding the two polypeptides.

Furthermore, to link a polypeptide comprising the amino acid sequence of the HSA mutant of the present invention to a polypeptide comprising the amino acid sequence of hGH, there is a method, for example, in which the two polypeptides are separately prepared and then linked via a non-peptide linker or a peptide linker. As a non-peptide linker, the following may be used: polyethylene glycol, polypropylene glycol, copolymers of ethylene glycol and propylene glycol, polyoxyethylated polyols, polyvinylalcohol, polysaccharides, dextran, polyvinylether, biodegradable polymers, lipid polymers, chitins, and hyaluronic acid, or derivatives thereof, or combinations thereof. On the other hand, a peptide linker is a peptide chain consisting of peptide bonded 1-50 amino acids or its derivative, whose N and C termini respectively form peptide bonds with the HSA mutant or a protein of interest to link the HSA mutant and the protein of interest.

Where the linker is specifically identified, a protein (A) linked with the HSA mutant using PEG as a non-peptide linker is referred to as an HSA mutant PEG-linked protein (A). Thus, it is referred to as HSA mutant PEG-linked hGH if hGH is chosen as a protein (A). HSA mutant PEG-linked hGH can be produced either by bonding the HSA mutant and PEG at first (PEGylated HSA mutant), and then bonding this with hGH, or by bonding hGH and PEG in advance (PEGylated hGH), and then bonding this with the HSA mutant. To bond PEG to the HSA mutant of the present invention, PEG modified with functional groups such as carbonate, carbonyldiimidazole, active carbonate, azlactone, cyclic imidethione, isocyanate, isothiocyanate, imidate, or aldehyde, is employed. Such functional groups attached to PEG react mainly with an amino group on the molecules of the HSA mutant and hGH, forming covalent bonds with the HSA mutant and hGH. Though there is no notable limitation as to the molecular weight of the PEG employed, its mean molecular weight (MW) is as follows: preferably MVV=500-60000, more preferably MW=500-20000. For example, PEG whose mean molecular weight is about 300, about 500, about 1000, about 2000, about 4000, about 10000, about 20000, or the like can preferably be used as a non-peptide linker.

PEGylated HSA mutant, for example, can be obtained by mixing the HSA mutant of the present invention with a polyethylene glycol having aldehyde groups as functional groups (ALD-PEG-ALD) at a molar ratio HSA/(ALD-PEG-ALD) of 11, 12.5, 15, 110, 120, and the like, and adding a reducing agent such as $NaCNBH_3$ or the like to the mixture, and letting them react. The above PEGylated HSA mutant then is allowed to react with hGH in the presence of a reducing agent such as $NaCNBH_3$ or the like to give HSA mutant PEG-linked hGH. Conversely, the HSA mutant PEG-linked hGH of the present invention can also be obtained by bonding hGH and ALD-PEG-ALD at first to form PEGylated hGH, and bonding this with the HSA mutant.

In the present invention, a preferable example of mHSA-linked (fused) hGH is the mHSA mutant-linked hGH having the amino acid sequence set forth as SEQ ID NO:11, in which the C terminus of 22K human growth hormone having the amino acid sequence set forth as SEQ ID NO:9 is linked to the N terminus of HSA(A320T) having the amino acid sequence set forth as SEQ ID NO:3, by forming a peptide bond without a linker. In the present invention, that which consists of HSA(A320T) and 22K hGH linked in this order is referred to as "22K human growth hormone-mHSA" or "22KhGH-mHSA". Likewise, that in which the N terminus of 22K human growth hormone is linked to the C terminus of HSA(A320T) by forming a peptide bond without a linker, is referred to as "mHSA-22K human growth hormone" or "mHSA-22KhGH".

Further, the mHSA mutant-linked hGH having the sequence set forth as SEQ ID NO:12, in which the C terminus of 22K human growth hormone set forth as SEQ ID NO:10 is linked to the N terminus of the human serum albumin(A320T) having the amino acid sequence set forth as SEQ ID NO:3, by forming a peptide bond without a linker, is referred to as "20K human growth hormone-mHSA" or "20KhGH-mHSA". Likewise, that in which the N terminus of 20K human growth hormone is linked to the C terminus of human serum albumin(A320T) by forming a peptide bond without a linker, is referred to as "mHSA-20K human growth hormone" or "mHSA-20KhGH".

The HSA mutant-linked human growth hormone of the preset invention is characterized in that it is remarkably stabilized in the blood, exhibiting a half-life generally not shorter than 10 hours in the blood $(t_{1/2}\beta)$ after subcutaneous injection to cynomolgus monkeys. While it would vary depending on doses, the half-life $(t_{1/2}\beta)$ of mHSA-22KhGH and 22KhGH-mHSA in the blood after a single subcutaneous administration to male cynomolgus monkeys at a dose of 4 mg/kg is 20-35 hours.

The HSA mutant-linked human growth hormone can be used as a medicament. It is also possible to use it as a medicament by allowing cooperation of the functions of human growth hormone and the HSA mutant in the living body.

The HSA mutant-linked human growth hormone of the present invention is very stable in the blood. Thus, the present invention stabilizes human growth hormone in the blood and enables it to remain for a long time, with its activity maintained, thereby leading to reduction of frequency of administration or dose of human growth hormone used as a medicament. For example, the frequency of administration of a medicament which must be administered daily could be reduced to once in 3-30 days by linking it to the HSA mutant of the present invention. Furthermore, the dose of such a medicament could be reduced to 1/3-1/100 in molar ratio.

The HSA mutant-linked human growth hormone of the present invention can be used as a medicament for the treatment of such disorders as growth hormone deficiency dwarfism, dwarfism in Turner syndrome, dwarfism by chronic renal failure, dwarfism in Prader-Willi syndrome, dwarfism in achondroplasia, dwarfism in SGA, all accompanied by no epiphyseal closure; and adult growth hormone deficiency, consumption caused by AIDS, and consumption caused by anorexia, and in addition, can also be used as a therapeutic drug for the treatment of disorders with such symptoms that could be ameliorated by long-term application of physiological activities of growth hormone, such as growth-promotion activity including acceleration of chondrogenesis, acceleration of protein anabolism, and the like, as well as improvement of body composition and lipids metabolism.

In the case where mHSA-22KhGH is administered to a patient with growth hormone deficiency dwarfism accompanied by no epiphyseal closure, a preferable dose is 0.01-0.7 mg/kg body weight at a time. In the case where hHSA-22KhGH is administered to a patient with dwarfism in Turner syndrome accompanied by no epiphyseal closure, a preferable dose is 0.15-1.4 mg/kg body weight at a time. In the case where mHSA-22KhGH is administered to a patient with dwarfism by chronic renal failure accompanied by no epiphyseal closure, a preferable dose is 0.01-1.4 mg/kg body weight at a time. In the case where mHSA-22KhGH is administered to a patient with Prader-Willi syndrome accompanied by no epiphyseal closure, a preferable dose is 0.012-0.98 mg/kg body weight at a time. In the case where mHSA-22KhGH is administered to a patient with dwarfism in achondroplasia accompanied by no epiphyseal closure, a preferable dose is 0.015-1.4 mg/kg body weight at a time. In the case where mHSA-22KhGH is administered to a patient with dwarfism in SGA accompanied by no epiphyseal closure, a preferable dose is 0.012-1.9 mg/kg body weight at a time. In the case where mHSA-22KhGH is administered to a patient with growth hormone deficiency, a preferable dose is 0.001-0.34 mg/kg body weight at a time. In the case where mHSA-22KhGH is administered to a patient with consumption caused by AIDS, a preferable dose is 0.005-0.4 mg/Kg body weight at a time. These doses, however, should be properly modified in accordance with the result of examination of the patient. Furthermore, a preferable interval of mHSA-22KhGH dosing for these disorders is once in 7-30 days, and it should be modified to once in 7-14 days, once in 10-20 days, once in 14-21 days according to the result of examination of the patient. The way of its administration is preferably subcutaneous injection, intramuscular injection, or intravenous injection, and more preferably subcutaneous injection or intramuscular injection.

A medicament containing a HSA mutant-linked protein as the active principle can be administered intravenously, intramuscularly, intraperitoneally, subcutaneously, or intracerabroventricularly, in the form of injectable preparation. Such an injectable preparation may be supplied in the form of a lyophilized preparation or an aqueous liquid preparation. In the case where an aqueous liquid preparation, it may be supplied either in the form of a vial filled with it or in the prefilled type preparation where it is already filled in a syringe. In the case of lyophilized preparation, it is reconstituted by dissolving it with an aqueous medium before use.

EXAMPLES

Though the present invention is described in further detail with reference to examples, it is not intended that the present invention be limited to the examples.

[Example 1] Construction of pE-mIRES-GS-puro

A vector, pEF/myc/nuc (Invitrogen), was digested with restriction enzymes (KpnI and NcoI) to cut out a DNA fragment containing EF-1α promoter and its first intron, and this DNA fragment was blunt-ended with T4 DNA polymerase. Separately, pCI-neo (Invitrogen) was digested with restriction enzymes (BglII and EcoRI) to cut and remove a region including CMV enhancer/promoter and its intron, and then blunt-ended with T4 DNA polymerase. Into this product was inserted the above region (blunt-ended) including EP-1α promoter and its first intron to prepare pE-neo vector (FIG. 1).

The vector, pE-neo, was digested with restriction enzymes (SfiI and BstXI) to cut and remove a region of about 1 kbp containing the neomycin resistance gene (FIG. 2). Using pcDNA3.1/Hygro(+) (Invitrogen), as a template, and primer Hyg-Sfi5' (SEQ ID NO:13) and primer Hyg-BstX3' (SEQ ID NO:14), PCR was conducted to multiply the hygromycin gene (FIG. 2). The hygromycin thus multiplied was digested with restriction enzymes (SfiI and BstXI) and inserted into the pE-neo vector to construct pE-hygr vector (FIG. 2).

An expression vector, pPGKIH (Miyahara M. et. al., J. Biol. Chem. 275,613-618 (2000)) was digested with restriction enzymes (XhoI and BamHI) to cut out a DNA fragment consisting of a nucleotide sequence comprising an internal ribosome entry site (IRES) derived from mouse encephalomyocarditis virus (EMCV), a hygromycin resistance gene (Hygr gene), and the polyadenylation region (mPGKpA) of mouse phosphoglycerate kinase (mPGK), i.e., IRES-Hygr-mPGKpA (SEQ ID NO:15: the region consisting of nucleotides 1-6 from its 5' end is an "XhoI site", the region consisting of nucleotides 120-715 and 716-718 (atg) which follow is the "nucleotide sequence comprising the internal ribosome entry site derived from the 5' untranslated region of mouse encephalomyocarditis virus genome, the region consisting of nucleotides 716-1741 including 716-718 (atg) is the "nucleotide sequence encoding the hygromycin resistance gene", the region consisting of nucleotides 1747-2210 is the "nucleotide sequence comprising the polyadenylation region of mouse phosphoglycerate kinase (mPGK)", and the region consisting of the 6 nucleotides (nucleotides 2211-2216) at the 3' end is a "BamHI site") (besides, the amino acid sequence corresponding to the Hygr gene is shown by SEQ ID NO:16). This DNA fragment was inserted between XhoI and BamHI sites of pBluescript SK(−) (Stratagene), and the resulting product was designated pBSK(IRES-Hygr-mPGKpA) (FIG. 3-1).

Using pBSK(IRES-Hygr-mPGKpA), as a template, and primer IRES5' (SEQ ID NO:17) and primer IRES3' (SEQ ID NO:18), PCR was conducted to multiply a DNA fragment comprising part of the IRES of EMCV. This DNA fragment was digested with restriction enzymes (XhoI and HindIII) and introduced between XhoI and HindIII sites of pBSK (IRES-Hygr-mPGKpA), and the resulting product was designated pBSK(NotI-IRES-Hygr-mPGKpA) (FIG. 3-2). Following digestion with restriction enzymes (NotI and BamHI), pBSK(NotI-IRES-Hygr-mPGKpA) was inserted between NotI and BamHI sites of pE-hygr vector, and the resulting product was designated plasmid pE-IRES-Hygr (FIG. 3-3).

Using the expression vector pPGKIH, as a template, and primer mPGKP5' (SEQ ID NO:19) and primer (mPGKP3') (SEQ ID NO:20), PCR was carried out to multiply a DNA fragment consisting of a nucleotide sequence comprising the mPGK promoter region (SEQ ID NO:21: nucleotides 4-9 from the 5' end is a "BglII site", the region consisting of nucleotides 10-516 which follows is the "nucleotide sequence comprising the promoter region of mouse phosphoglycerate kinase gene (mPGK)", and the region consisting of nucleotides 524-529 which follows is an "EcoRI site"). This DNA fragment was digested with restriction enzymes (BglII and EcoRI), and inserted between BglII and EcoRI sites of pCI-neo (Promega), and the resulting product was designated pPGK-neo (FIG. 3-4). Following digestion of pE-IRES-Hygr with restriction enzymes (NotI and BamHI) to cut out a DNA fragment (IRES-Hygr), which then was inserted between NotI and BamH sites of pPGK-neo, and the resulting product was designated pPGK-IRES-Hygr (FIG. 3-5).

From CHO-K1 cells, cDNA was prepared, and using this cDNA, as a template, and primer GS5' (SEQ ID NO:22) and primer GS3' (SEQ ID NO:23), PCR was carried out to multiply a DNA fragment comprising GS gene. This DNA fragment was digested with restriction enzymes (Ball and BamHI), and inserted between Ball and BamHI sites of pPGK-IRES-Hygr, and the resulting product was designated pPGK-IRES-GS-ΔpolyA (FIG. 3-6).

Using pCAGIPuro (Miyahara m. et. al., J. Biol. Chem. 275,613-618 (2000)), as a template, and primer puro5' (SEQ ID NO:24 and primer puro3' (SEQ ID NO:25), a DNA fragment consisting of a nucleotide sequence comprising a puromycin resistance gene (puro gene) was multiplied by PCR (SEQ ID NO:26: the region consisting of nucleotides 2-7 from the 5' is "AflII site", the region consisting of nucleotides 8-607 which follows is the "nucleotide sequence encoding the puromycin resistance gene (puro gene)", and the region consisting of nucleotides 608-619 which follows is a "BstXI site") (besides, the amino acid sequence corresponding to the puro gene is shown by SEQ ID NO:27). This DNA fragment was digested with restriction enzymes (AflII and BstXI) and then inserted between AflII and BstXI sites, and the resulting product was designated pE-puro (FIG. 3-7).

Using pE-puro, as a template, and primer SV40polyA5' (SEQ ID NO:28) and primer SV40polyA3' (SEQ ID NO:29), a DNA fragment including the SV40 late polyadenylation region was multiplied by PCR. This DNA fragment was digested with restriction enzymes (NotI and HpaI) and then inserted between NotI and HpaI sites of the expression vector pE-puro, and the resulting product was designated pE-puro(XhoI) (FIG. 3-8). By digesting pPGK-IRES-GS-ΔpolyA with restriction enzymes (NotI and XhoI), a DNA fragment including IRES-GS region was cut out, which then was inserted between NotI and XhoI sites of the expression vector pE-puro(XhoI), and the resulting product was designated pE-IRES-GS-puro (FIG. 3-9).

Using the expression vector pE-IRES-GS-puro, as a template, and primer mIRES-GS5' (SEQ ID NO:30) and primer mIRES-GS3' (SEQ ID NO:31), the region from IRES of the EMCV to GS was multiplied by PCR in which the 2nd start codon (atg) from the 5' end of the IRES of EMCV was destroyed by introduction of mutation. Using the expression vector pE-IRES-GS-puro, as a template, and the above DNA fragment and the primer IRES5' mentioned above, a DNA fragment including the above region from IRES to GS was multiplied by PCR. This DNA fragment was digested with restriction enzymes (NotI and PstI), and a DNA fragment thus cut out was inserted between NotI and PstI sites of the expression vector pE-IRES-GS-puro, and the resulting product was designated pE-mIRES-GS-puro, an expression vector for mammalian cells (FIG. 4).

[Example 2] Construction of a Vector for Expression of HSA-22KhG

SEQ ID NO:32 shows the amino acid sequence of the fusion protein HSA-22KhGH, which is the product resulting by fusing the C terminus of the wild-type HSA (SEQ ID NO:1) to the N terminus of 22KhGH. In this amino acid sequence, the amino acid residues 1-585 corresponds to the amino acid sequence of wild-type mature HSA (SEQ ID NO:1), and the amino acid residues 586-776 corresponds to the amino acid sequence of 22KhGH. The DNA having the nucleotide sequence set forth as SEQ ID NO:33, including the gene encoding HSA-22KhGH (HSA-22KhGH gene) was chemically synthesized. In this sequence, nucleotides 11-82, nucleotides 83-1837, and nucleotides 1838-2410 encode the HSA leader peptide, mature HSA, and mature hGH, respectively. This DNA was digested with restriction enzymes (MluI and NotI), and inserted between MluI and NotI sites of pE-mIRES-GS-puro prepared in Example 1 to construct vector pE-mIRES-GS-puro(HSA-22KhGH) for expression of HSA-22KhGH.

[Example 3] Construction of a Vector for Expression of mHSA-22KhGH

The fusion protein having the amino acid sequence set forth as SEQ ID NO:34, which was the product obtained by fusing the C terminus of HSA(A320T) (SEQ ID NO:3) with the N terminus of 22KhGH, was designated mHSA-22KhGH. In the amino acid sequence set forth as SEQ ID NO:34, amino acid residues 1-585 corresponds to the amino acid sequencer of mHSA, and the amino acid residues 586-776 corresponds to the amino acid sequence of 22KhGH. Using pE-mIRES-GS-puro(HSA-22KhGH) prepared in Example 2, as a template, and primer YA082 (SEQ ID NO:35) and primer YA083 (SEQ ID NO:36), a DNA fragment comprising the gene encoding mHSA-22KhGH by PCR. By self-annealing of this DNA fragment, pE-mIRES-GS-puro(mHSA-22KhGH) was constructed as the vector for expression of mHSA-22KhGH.

[Example 4] Construction of a Vector for Expression of 22KhGH-HSA

The fusion protein having the amino acid sequence set forth as SEQ ID NO:37, which was the product obtained by fusing the C terminus of 22KhGH with the N terminus of wild-type HSA (SEQ ID NO:1), was designated 22KhGH-HSA. In the amino acid sequence set forth as SEQ ID NO:37, amino acid residues 1-191 corresponds to the amino acid sequence of 22KhGH, and amino acid residues 192-776 corresponds to the amino acid sequence of HSA. A DNA having the nucleotide sequence set forth as SEQ ID NO:38 containing the gene encoding 22KhGH-HSA (22KhGH-HSA gene) was chemically synthesized. In this sequence, nucleotides 11-88 encodes the hGH leader peptide, nucleotides 89-661 mature hGH, nucleotides 662-2416 mature HSA, respectively. This DNA was digested with restriction enzymes (MluI and NotI) and inserted between MluI and NotI sites of pE-mIRES-GS-puro prepared in Example 1 to construct pE-mIRES-GS-puro(22KhGH-HSA) as the vector for expression of 22KhGH-HSA.

[Example 5] Construction of a Vector for Expression of 22KhGH-mHSA

The fusion protein having the amino acid sequence set forth as SEQ ID NO:39, which was the product obtained by fusing the C terminus of 22KhGH with the N terminus of HSA(A320T) (SEQ ID NO:3), was designated 22KhGH-mHSA. Using pE-mIRES-GS-puro(22KhGH-HSA) prepared in Example 4, as a template, and primer YA082 (SEQ ID NO:35) and primer YA083 (SEQ ID NO:36), a DNA fragment comprising the gene encoding 22KhGH-mHSA was multiplied by PCR. By self-annealing of this DNA fragment, pE-mIRES-GS-puro(22KhGH-mHSA), the vector for expression of 22KhGH-mHSA, was constructed.

[Example 6] Preparation of Fusion Protein Expressing Cells

Cells for expression of each fusion protein, HSA-22KhGH, mHSA-22KhGH, 22KhGH-HSA, and 22KhGH-mHSA were prepared in the following manner. Into CHO-K1 cells, the cells derived from Chinese hamster ovary cells, were separately introduced the expression vectors prepared in Examples 2-5, i.e., pE-mIRES-GS-puro(HSA-22KhGH), which was the expression vector for HSA-22KhGH, pE-mIRES-GS-puro(mHSA-22KhGH), which was the expression vector for mHSA-22KhGH, pE-mIRES-GS-puro (22KhGH-HSA), which was the expression vector for 22KhGH-HSA, and pE-mIRES-GS-puro(22KhGH-mHSA), which was the expression vector for 22KhGH-mHSA, using Gene Pulser Xcell electroporation system (Bio Rad). The cells having one of the expression vectors introduced were subjected to selection culture in a CD OptiCHO™ medium (Thermo Fisher Scientific) using methionine sulfoximine (SIGMA) and puromycin (SIGMA) to establish cells for expression of HSA-22KhGH, cells for expression of mHSA-22KhGH, cells for expression of 22KhGH-HSA, and cells for expression of 22KhGH-mHSA, respectively. In the selection culture, the concentration of methionine sulfoximine and puromycin was increased stepwise, up to the final concentration of 300 μM for methionine sulfoximine, and 10 μg/mL for puromycin, to selectively promote the cells having stronger drug resistance.

The cells for expression of HSA-22KhGH, cells for expression of mHSA-22KhGH, cells for expression of 22KhGH-HSA, and cells for expression of 22KhGH-mHSA are generally referred to as HSA-hGH fusion protein expressing cells, and the fusion proteins between HSA and hGH obtained by culturing those cells are generally referred to as HSA-hGH fusion proteins.

[Example 7] Culture of Fusion Protein-Expressing Cells

HSA-22KhGH expressing cells, mHSA-22KhGH expressing cells, 22KhGH-HSA expressing cells, and 22KhGH-mHSA expressing cells were cultured in the following manner. To CD OptiCHO™ medium (Thermo Fisher Scientific) were added methionine sulfoximine and puromycin at the final concentration of 300 μM and 10 μg/mL, respectively, to prepare a cell culture medium. The respective cells for expression prepared in Example 6 were added to 5 mL each of the cell culture medium at a density of $2\times10^5$ cells/mL, and cultured at 37° C. in the presence of 5% $CO_2$. The cells were transferred to a fresh culture medium to the density of $2\times10^5$ cells/mL once in 5 days, and subcultured.

[Example 8] Purification of HSA-hGH Fusion Proteins

Purification of HSA-22KhGH, mHSA-22KhGH, 22KhGH-HSA, and 22KhGH-mHSA were carried out in the following manner. The respective cells for expression subcultured in Example 7 were suspended in their cell culture medium at a density of $2\times10^5$ cells/mL to make the total volume of 240 mL. The cell suspension was added, 30 mL each, to eight 15-cm petri dishes and cultured for 5 days at 37° C. Following this culture, each of the medium was collected through a membrane filter (pore size 0.22, Millipore) to obtain the culture supernatant. To each of the supernatant, 1 M HEPES (pH 8.0) then was added to adjust the pH to 7.0-7.2.

A polypropylene column (Poly-Prep™ Bio-Rad) was filled with a resin to which 5 mL of anti-human growth hormone antibody had been bound (Capture Select™ anti hGH resin, Thermo Fisher Scientific), and the resin was equilibrated with 5 column volumes of 10 mM HEPES buffer containing 500 mM NaCl (pH 7.5). The above culture supernatant, following pH adjustment, was loaded onto the column at a flow rate of about 2.5 mL/min to allow the HSA-hGH fusion protein to be adsorbed by the resin. The column then was washed with 5 column volumes of 10 mM HEPES buffer containing 500 mM NaCl (pH 7.5) supped at the same flow rate. The HSA-hGH fusion protein was eluted from the resin with 5 column volumes of 0.1 M glycine buffer (pH 3.0) containing 100 mM NaCl. Fractions containing HSA-hGH fusion protein was collected and 7% (v/v) of 1 M HEPES buffer (pH 8.0) was immediately added. The concentration of HSA-hGH fusion protein in the eluate was determined by Pierce™ BCA Protein Assay Kit (Thermo Fisher Scientific) using BSA as a standard compound.

[Example 9] Preparation of BaF3/hGHR Cells

BaF3/hGHR cells having acquired GH-dependent growth ability was produced by introducing of human GH receptor (hGHR) gene into mouse BaF3 cells as follows. PCR was carried out using a hGHR ECD artificially synthesized gene having the nucleotide sequence set for as SEQ ID 40 (a 5' side fragment of the hGHR gene encoding the extra cellular domain of hGHR), as a template, and primer YA034 (SEQ ID NO:41) and primer YA035 (SEQ ID NO:42). The PCR product was subjected to agarose electrophoresis and purified using QIAEX II (QIAGEN). This DNA fragment was employed as megaprimer. Using cDNA derived from human lung as a template, primer K708 (SEQ ID NO:43), and primer K709 (SEQ ID NO:44), PCR was carried out to multiply a DNA fragment including the full length hGHR gene. The PCR product thus obtained was subjected to agarose electrophoresis, and purified using QIAEX II. Using the purified DNA fragment including the full-length hGHR gene as a template, the above megaprimer, and primer K709 (SEQ ID NO:44), PCR was carried out to amplify the DNA fragment having the nucleotide sequence set forth as SEQ ID NO:45, which included a gene encoding the full-length hGHR that had a hGHR ECD artificially synthesized nucleotide sequence on the 5' end side. This DNA fragment was digested with restriction enzymes (MluI and NotI) and then inserted between MluI and NotI sites of retrovirus vector pMX-II (Ono Y., Oncogene. 19. 3050-8 (2000)) to provide a retrovirus vector for hGHR expression (hGHR/pMX-II).

In 10 mL of DMEM medium containing 10% FBS, $6\times10^6$ of "293 cells" (Dainippon Pharmaceutical) were suspended. This suspension was added to 10-cm petri dishes and cultured for 24 hours at 37° C. in the presence of 5% $CO_2$. The "293 cells" employed here was human embryonic kidney cells transformed with the E1 gene of adenovirus.

To 500 μL of Opti-MEMI™ medium (Thermo Fisher Scientific) was added 15 μL of X-tremeGENE 9 DNA Transfection Reagent (Roche) and mixed, and to this mixture, 5 μg of the retrovirus packaging vector pCL-Eco (IMGENEX) and 5 μg of hGHR/pMX-II were further added and mixed. This mixture solution was left undisturbed for 15 minutes at room temperature, and then added to the above mentioned 10-cm dishes in which the "293 cells" had been cultured for 24 hours. The cells then were cultured for 24 hours at 37° C. in the presence of 5% $CO_2$, and the medium then was centrifuged at 3000 rpm for 5 minutes to collect the supernatant. The supernatant thus collected was used as the hGHR expressing retrovirus solution.

WEHI-3 cells (Riken) were cultured in RPMI640 medium containing 10% FBS, and the medium were centrifuged at 3000 rpm for 5 minutes to collect the supernatant. To 2 mL of the hGHR expressing retrovirus solution were added 500 μL of the culture supernatant of WEHI-3 cells and 2.5 mL of RPMI1640 medium containing 10% FBS, and mixed. This mixture solution was added to $2\times10^6$ BaF3 cells (Riken) of an IL-3 dependent cell line, and the cells were suspended. This cell suspension was transferred to a 75-cm$^2$ culture flask and cultured in the presence of 5% $CO_2$ at 37° C. for 8 hours, and following addition of 500 μL of the supernatant of WEHI-3 cell culture and 2.5 mL of RPMI1640 medium containing 10% FBS, cultured for further 16 hours. After this culture, the cells were collected by centrifugation, and washed three times with PBS. To the collected cells was added 5 mL of RPM1640 medium containing 22KhGHR at 100 ng/mL to suspend the cells, and the suspended cells were transferred to a culture flask and cultured in the presence of 5% $CO_2$ at 37° C. to obtain BaF3 cells that had acquired GH-dependent growth ability as a result of the expression of the hGHR gene. The cells were designated BaF3/hGHR cells.

[Example 10] Determination of Cell Growth Activity Using BaF3/hGHR Cells

Cell growth activity of HSA-hGH fusion protein was evaluated using the BaF3/hGHR cells prepared by the method described in Example 9.

BaF3/hGHR cells at the log growth phase were washed three times with PBS, and diluted to $1\times10^6$ cells/mL with 15 mL of RPMI1640 medium containing 1% horse serum, and cultured in the presence of 5% $CO_2$ at 37° C. for 16 hours. After this culture, the cells were diluted to $3\times10^5$ cells/mL with the same medium, and 100 μL of it was seeded in each well of a 96-well culture plate. The HSA-hGH fusion proteins (HSA-22KhGH, mHSA-22KhGH, 22KhGH-HSA, and 22KhGH-mHSA) purified in Example 8 were diluted to each of 7 different concentrations (90.3 nM, 18.1 nM, 3.6 nM, 0.72 nM, 0.14 nM, 0.029 nM, and 0.0058 nM) with PBS containing 0.1% BSA to prepare diluted solutions.

The diluted solutions prepared above was added, 20 µL each, to the wells of the 96-well culture plate that had been seeded with BaF3/hGHR cells, mixed on a plate shaker, and cultured in the presence of 5% $CO_2$ at 37° C. for 22 hours. After this culture, CellTiter96™ Aqueous One Solution Cell Proliferation Assay test solution, which was a reagent in colorimetric analysis for counting the number of living cells, was added to the well, 24 µL each, and mixed, and culture was continued for further 3 hours. Absorbance then was measured for each well at 490 nm using a plate reader. The values measured were plotted, with absorbance at 490 nm on the vertical axis, and molar concentration (nM) on the horizontal axis. As absorbance at 490 nm indicated a relative value corresponding to the number of living cells, the curve produced by plotting the measured values represented the correlation between the concentration of the test sample and the growth level of the cells. The concentration of the test sample at which the level of the cell growth was 50% of the maximum cell growth on the curve was determined as $EC_{50}$. Measurement was carried out three times for each test sample.

[Example 11] Pharmacodynamic and Pharmacological Analyses Using Cynomo ES Monkeys Each of the HSA-hGH fusion proteins purified in Example 8 (HSA-22KhGH, mHSA-22KhGH, 22KhGH-HSA, and 22KhGH-mHSA) was subcutaneously administered once, at a dose of 4.0 mg/kg, to male cynomolgus monkeys. HSA-22KhGH was administered to 3 cynomolgus monkeys, and mHSA-22KhGH, 22KhGH-HSA, or 22KhGH-mHSA was administered to one cynomolgus monkey.

Peripheral blood samples were taken from the animals for pharmacodynamic analysis 15 minutes, and 1, 4, 8, 12, 24, 48, 72, 120, 168, and 216 hours after the administration. The blood was taken in blood collection tubes containing potassium EDTA, cooled with ice, and centrifuged (17000×g, 5 minutes, 4° C.) to separate the plasma. The concentration of HSA-hGH fusion protein contained in the plasma thus prepared was measured by a method detailed in Example 12 below, and by plotting the concentration of HSA-hGH on the vertical axis, and the time elapsed after administration on the horizontal axis, Cmax, $AUC_{0-216\,h}$, $AUC_{0-inf}$, and $t_{1/2}\beta$ were determined to perform pharmacodynamic analysis.

Further, the pharmacological effect of HSA-hGH fusion protein was analyzed as follows using promotion of IGF-1 secretion as an index. Peripheral blood was taken before administration, as well as 6 and 12 hours and 1, 2, 3, 4, 5, 6, 7, 8, and 9 days after administration, and plasma was prepared from the peripheral blood in the above-described manner. The concentration of IGF-1 in the plasma was determined by the method described in Example 13, and pharmacological analysis was performed by plotting the concentration of IGF-1 on the vertical axis, and the time elapsed after administration on the horizontal axis. Furthermore, as a control, an additional cynomolgus monkey was provided, and 22KhGH (Growject™) was administered to it subcutaneously at a dose of 0.3 mg/kg for 7 consecutive days, and the concentration of IGF-1 in plasma was measured simultaneously.

[Example 10] Determination of HSA-hGH Fusion Protein in Plasma

Mouse anti-HSA monoclonal antibody and mouse anti-hGH antibody were obtained by culturing hybridoma cells produced by fusing mouse spleen cells immunized by HSA or hGH with myeloma cells by a conventional method well known to those skilled in the art. Mouse anti-hGH monoclonal antibody was dialyzed against 0.1 M $NaHCO_3$ solution (pH9), and the concentration of the antibody in the solution was measured using NanoDrop™ (Thermo Scientific). EZ-Link™ NHS-LC-Biotin (Thermo Fisher Scientific) dissolved at 5 mg/mL in DMSO then was added to the antibody solution at a ratio of 60 µg of NHS-LC-Biotin per 1 mg of the antibody, and after letting a reaction take place for 2 hours at room temperature, the reaction solution was dialyzed against PBS to obtain biotinylated mouse anti-hGH monoclonal antibody. The mouse anti-HSA monoclonal antibody was used as the primary antibody, and biotinylated mouse-anti hGH monoclonal antibody as the secondary antibody, respectively, in the determination method described below.

The concentration of the HSA-hGH fusion protein in plasma was determined by electrochemiluminescence (ECL) immunoassay. ECL immunoassay is a method in which a sample is determined by applying electrochemical stimulation to a secondary antibody labeled with a ruthenium complex, SULFO-TAG, on a plate while detecting the luminescence with a CCD camera at the wavelength of 620 nm caused by oxidation-reduction of SULFO-TAG.

Measurement was carried out largely in the following manner according to the product manual of Sector Imager 6000. The mouse anti-HSA monoclonal antibody was added to High Bind Plate (Meso Scale Diagnostics), and left undisturbed for one hour to immobilize the anti-HSA antibody (primary antibody) to the plate. Superblock Blocking buffer in PBS (Thermo Fisher Scientific) then was added to the plate, and shaken for one hour to block the plate. The plate was washed with PBST (PBS containing 0.05% Tween20), and following addition of a sample, shaken for one hour. The plate was washed with PBST, and after addition of the biotinylated mouse anti-hGH monoclonal antibody (secondary antibody), shaken for one hour. The plate was washed with PBST, and after addition of SULFO-Tag-Streptavidin (Meso Scale Diagnostics), shaken for one hour. After washing the plate with PBST, Read buffer T (Meso Scale Diagnostics) was added, and luminescence at 620 nm was measured using Sector Imager 6000 (Meso Scale Diagnostics). Known concentrations of HSA-hGH were determined in the same manner on the same plate to obtain a standard curve, and the concentration of HSA-hGH in the plasma was determined by interpolating the values measured for the sample.

[Example 13] Determination of IGF-1 in Plasma

Determination of IGF-1 in the plasma was carried out by ELISA using Human IGF-I Quantikine ELISA kit (R&D systems).

[Example 14] Results and Discussion (1) Determination of Cell Growth Activity Using BaF3/hGHR Cells FIG. 5 illustrates the result of the determination of cell growth activity using BaF3/hGHR cells, a figure produced by plotting absorbance at 490 nm on the vertical axis and molar concentration (nM) for each sample on the horizontal axis. The $EC_{50}$ values for each sample determined from this figure are shown in Table 1.

TABLE 1

EC$_{50}$ values for each sample
(values of cell growth activity using BaF3/hGHR cells)

|  | HSA-22KhGH | mHSA-22KhGH | 22KhGH-HSA | 22KhGH-mHSA |
|---|---|---|---|---|
| EC$_{50}$ (nM) | $1.38 \times 10^{-1}$ | $1.53 \times 10^{-1}$ | $8.78 \times 10^{-1}$ | 1.20 |

As seen from Table 1, the EC$_{50}$ values of HSA-22KhGH and mHSA-22KhGH, i.e., 22KhGH linked to the C terminus of human serum albumin, were $1.38 \times 10^{-1}$ nM and $1.53 \times 10^{-1}$ nM, respectively, indicating that the both had approximately equivalent cell growth activities. Further, as to 22KhGH-HSA and 22KhGH-mHSA, i.e., 22KhGH linked to the N terminus of human serum albumin, their EC$_{50}$ values were $8.78 \times 10^{-1}$ nM and 1.20 nM, indicating that these two had also largely equivalent cell growth activities to each other.

On the other hand, comparison of the EC$_{50}$ values between HSA-22KhGH and 22KhGH-HSA showed that the EC$_{50}$ values of 22KhGH-HSA was about 6.4 times the EC$_{50}$ values of HSA-22KhGH, and comparison of the EC$_{50}$ values between mHSA-22KhGH and 22KhGH-mHSA showed that the EC$_{50}$ values of 22KhGH-mHSA was about 7.8 times the EC$_{50}$ values of mHSA-22KhGH.

The results indicate that when preparing a fusion protein is by linking 22KhGH with human serum albumin, to link 22KhGH to the C terminus of human serum albumin will provides a fusion protein exhibiting a greater cell growth activity of 22KhGH than to link it to the N terminus of human serum albumin, at least in vitro. Thus, the above results suggest that when producing a therapeutic agent for the treatment of growth hormone deficiency dwarfism by linking 22KhGH with human serum albumin, it is preferred to link 22KhGH to the C terminus of human serum albumin.

(2) Pharmacodynamic Analysis Using Cynomolgus Monkeys

FIG. 6 illustrates the result of pharmacodynamic analysis of the HSA-hGH fusion proteins produced by plotting the concentration of the HSA-hGH fusion proteins (HSA-22KhGH, mHSA-22KhGH, 22KhGH-HSA and 22KhGH-mHSA) in the blood of cynomolgus monkeys on the vertical axis, and the time elapsed after administration of the HSA-hGH fusion proteins on the horizontal axis. Cmax, AUC$_{0-216\ h}$, AUC$_{0-inf}$ and t$_{1/2}\beta$ derived from this figure is shown in Table 2.

TABLE 2

Pharmacodynamis for each sample

|  | Cmax (μg/mL) | AUC$_{0-216\ h}$ (μg · hr/mL) | AUC$_{0-inf}$ (μg · hr/mL) | t$_{1/2}\beta$(hr) |
|---|---|---|---|---|
| HSA-22 KhGH | 20.1 ± 3.4 | 751 ± 54 | 752 ± 55 | 30.0 ± 1.5 |
| mHSA-22 KhGH | 20.3 | 736 | 737 | 29.9 |
| 22 KhGH-HSA | 23.1 | 2210 | 2220 | 17.6 |
| 22 KhGH-mHSA | 33.2 | 3220 | 3260 | 26.8 |

As seen in Table 2, as for AUC, the AUC$_{0-inf}$ for HSA-22KhGH and mHSA-22KhGH, which were produced by liking 22KhGH to the C terminus of human serum albumin, were 752±55 μg hr/mL, and 737 μg hr/mL, respectively. In contrast, the AUC$_{0-inf}$ for 22KhGH-HSA and 22KhGH-mHSA, which were produced by linking 22KhGH to the N terminus of human serum albumin, were 2220 μg·hrs/mL and 3260 μg·hrs/mL, respectively. The result demonstrates the product produced by linking 22KhGH to the N terminus of human serum albumin is much more stable in the blood than the product produced by linking 22KhGH to the C terminus of human serum albumin. Further, HSA-22KhGH and mHSA-22KhGH, both produced by linking 22KhHG to the C terminus of human serum albumin were shown to have equivalent AUC$_{0-inf}$ values, whereas in comparison with 22KhGH-HSA and 22KhGH-mHSA, which were produced by linking 22KhGH to the N terminus of human serum albumin, the AUC$_{0-inf}$ value for 22KhGH-mHSA was shown to be as high as about 1.47 times that for 22KhGH-HSA, indicating that 22KhGH-mHSA is particularly stable in the blood.

The above results unexpectedly show that the stability of the resulting fusion protein in the blood varies greatly upon whether the N terminus of human growth hormone being linked to the C terminus of human serum albumin, or conversely the N terminus of human serum albumin being linked to the C terminus of human growth hormone, and far more greater stability can be achieved in the latter case. In addition, the results indicate that stability of human growth hormone in the blood is most particularly increased when the N terminus of HSA(A320T) is linked to the C terminus of human growth hormone, namely that HSA(A320T) has the capacity to remarkably increase the stability in the blood of a protein that is linked to its N terminus. Thus, taken together, the above results indicate that as a means to stabilize a variety of proteins to be administered to human and other mammals as a medicament, such as growth hormone or the like, it is effective to link such proteins with HSA(A320T), and in particular, to link their C terminus to the N terminus of HSA(A320T), via a peptide bond for example.

(3) Pharmacodynamic Analysis Using Cynomolgus Monkeys

FIG. 7 illustrates the result of pharmacodynamic analysis of the HSA-fused 22KhGH, in which the vertical axis represents the concentration of IGF-1, and the horizontal axis the time elapsed after administration of HSA-22KhGH fusion protein. IGF-1 is a polypeptide whose secretion is induced by growth hormone and having activities such as promotion of bone growth. Some of hGH's activities are known to be exhibited via IGF-1

As seen in FIG. 7, in the animals that were administered HSA-22KhGH or mHSA-22KhGH, i.e., the products in which 22KhGH was linked to the C terminus of human serum albumin, the concentration of IGF-1 in the plasma showed the maximum value, 1.5 times as high as the value prior to administration, on the third day after administration in the case of HSA-22KhGH-administered animals, and in the case of HSA-m22KhGH-administered animals, the maximum value, about 2 times as high as the value prior to administration, on the second day after administration. Afterwards, however, the concentration of IGF-1 in plasma declined, and from the fifth day on after administration, it became comparable to the control 22KhGH, in both cases. Besides, as seen in FIG. 7, the concentration of IFG-1 in plasma showed no notable increase after the administration of 22KhGH. This seems to be that because of the short half-life of 22KhGH in the blood, about 20 minutes, the concentration of IGF-1 had already returned to its value recorded before administration when the blood was sampled. Further, the concentration of IGF-1 in the plasma of 22hGH-administered animals increased on the second day and showed higher values up to the ninth day than the value recorded before administration. This seems to be an accumulated effect of 22KhGH, only which was administered 7 consecutive days.

On the other hand, as to the concentration of IGF-1 in the plasma of animals that were administered HSA-22KhGH or mHSA-22KhGH, i.e., the products in which 22KhGH was linked to human serum albumin on the N terminus, it showed the maximum value, about 2.0 times as high as the value prior to administration, on the seventh day after administration in the case of 22KhGH-HSA-administered animals, and also in the case of 22KhGH-mHSA-administered animals, the maximum value, about 2.0 times as high as the value prior to administration, on the seventh day after administration. Further, in both cases, the concentration of IGF-1 in the plasma was kept higher than that of the control 22KhGH, even on the ninth day after administration. Furthermore, comparison between HSA-22KhGH and mHSA-22KhGH shows that while the concentration of IGF-1 tended to be higher with HSA-22KhGH up to the third day after administration, the concentration of IFG-1 was consistently higher with mHSA-22KhGH from the fifth day on after administration. This indicates that mHSA-22KhGH can maintain the IGF-1 concentration in the blood at high values for a longer period than HSA-22KhGH.

These results show that the pharmacological effect of growth hormone can be greatly extended by linking it to the N terminus of HSA(A320T), which therefore indicates that 22KhGH-mHSA, the product obtained by linking the C terminus of growth hormone to the N terminus of HSA (A320T), can be preferably used as a long-lasting growth hormone whose pharmacological activity is kept longer than conventional growth hormone preparations (Gorwjec™, etc.). Moreover, the above results indicate that the activity of a physiologically active protein to be administered to an animal as a medicament or the like, can be greatly maintained in the plasma by linking it to the N terminus of HSA(A320T), and that linking a physiologically active protein to HSA(A320T) is an effective means to provide a long-lasting type medicament whose pharmacological activity lasts for a long period of time, and in particular, that it is effective to link the C terminus of a physiologically active protein to the N terminus of HSA(A320T) via a peptide bond.

Since the concentration of IGF-1 in plasma was maintained at very high levels even on the ninth day after administration as shown in the 22KhGH-mHSA-administered animals, it is reasonably expected that 22KhGH-mHSA would sufficiently exhibit its activity if administered at an interval of once in 7-14 days to such patient with growth hormone deficiency dwarfism, adult growth hormone deficiency, or the like. Table 3 shows examples of dosage of 22KhGH-mHSA when administered to patients with growth hormone deficiency dwarfism, adult growth hormone deficiency, or the like. The dose and dosing intervals shown in Table 3 should be adjusted as desired in accordance with clinical symptoms and results of examinations such as IGF-1 concentration. 22KhGH-mHSA is administered to a patient preferably in the form of intramuscular injection or subcutaneous injection.

[Table 3]

TABLE 3

Indications and dose of 22KhGH-mHSA

| Indications | Dose at a time (mg/ kg body weight) | Dosing intervals |
|---|---|---|
| Growth hormone deficiency dwarfism accompanied by no epiphyseal closure | 0.01-0.7 | 7-14 days |
| Dwarfism in Turner syndrome accompanied by no epiphyseal closure | 0.015-1.4 | 7-14 days |
| Dwarfism by chronic renal failure accompanied by no epiphyseal closure | 0.01-1.4 | 7-14 days |
| Dwarfism in Prader-Willi syndrome accompanied by no epiphyseal closure | 0.012-0.98 | 7-14 days |
| Dwarfism in achondroplasia accompanied by no epiphyseal closure | 0.015-1.4 | 7-14 days |
| Dwarfism in SGA accompanied by no epiphyseal closure | 0.012-1.9 | 7-14 days |
| Adult growth hormone deficiency | 0.001-0.34 | 7-14 days |
| Consumption caused by AIDS | 0.005-0.4 | 7-14 days |

[Preparation Example 1] Aqueous Injection

Sodium hydrogen phosphate, heptahydrate 1.33 mg
Sodium dihydrogen phosphate 1.57 mg
Polyoxyethylene(160)polyoxypropylene(30)glycol 3 mg
Benzylalcohol 13.5 mg
D-mannitol 52.5 mg
22KhGH-mHSA 1 mg The above ingredients are dissolved at their respective proportions in water for injection, and after pH adjustment to 6.0-6.4, made to volume of 1.5 mL to provide an aqueous injection.

[Preparation Example 2] Aqueous Injection

L-histidine 1 mg
Phenol 4.5 mg
Polyoxyethylene(160)polyoxypropylene(30)glycol 4.5 mg
D-mannitol 60 mg
22KhGH-mHSA 1 mg The above ingredients are dissolved at their respective proportions in water for injection, and after pH adjustment to 6.0-6.4, made to volume of 1.5 mL to provide an aqueous injection.

[Preparation Example 3] Lyophilized Preparation

Sodium hydrogen phosphate, heptahydrate 2.475 mg
Sodium dihydrogen phosphate 0.394 mg
Sodium chloride 1.125 mg
Aminoacetic acid 11.25 mg
D-mannitol 22.5 mg
22KhGH-mHSA 1 mg A lyophilized preparation of the above composition is dissolved in 1 mL of water for injection containing 9.7 mg of benzylalcohol.

INDUSTRIAL APPLICABILITY

As the present invention increase the stability in the blood of a protein of interest to be administered to an animal as a medicament, it enables provision of a new medicament that allows reduction of the dose of such a protein when administered.

REFERENCE SIGNS LIST

1 LacZ promoter
2 mPGK promoter
3 Partial sequence of internal ribosome entry site of wild-type mouse encephalomyocarditis virus including the nucleotide sequence set forth as SEQ ID NO:7
3a Partial sequence of internal ribosome entry site mutant-type mouse encephalomyocarditis virus including the nucleotide sequence set forth as SEQ ID NO:8
4 Polyadenylation region of mPGK (mPGKpA)
5 Nucleotide sequence containing EP-1p and its first intron
6 SV40 late polyadenylation region
7 Region containing SV40 early promoter
8 Synthetic polyadenylation region
9 Region containing cytomegalovirus promoter
10 Glutamine synthetase gene

SEQUENCE LISTING FREE TEXT

SEQ ID NO:3: Human serum albumin mutant (A320T)
SEQ ID NO:4: Example linker
SEQ ID NO:5: Example linker
SEQ ID NO:6: Example linker
SEQ ID NO:8: Partial sequence of IRES from mutant-type murine encephalomyocarditis virus, synthetic
SEQ ID NO:11: 22KhGH-mHSA, mature
SEQ ID NO:12: 20KhGH-mHSA, mature
SEQ ID NO:13: Primer Hyg-Sfi5', synthetic
SEQ ID NO:14: Primer Hyg-BstX3', synthetic
SEQ ID NO:15: IRES-Hygr-mPGKpA, synthetic
SEQ ID NO:16: Amino acid sequence corresponding to hygromycin resistance gene
SEQ ID NO:17: Primer IRES5', synthetic
SEQ ID NO:18: Primer IRES3', synthetic
SEQ ID NO:19: Primer mPGKP5', synthetic
SEQ ID NO:20: Primer mPGKP3', synthetic
SEQ ID NO:21: mPGKp, synthetic
SEQ ID NO:22: Primer GS5', synthetic
SEQ ID NO:23: Primer GS3', synthetic
SEQ ID NO:24: Primer puro5', synthetic
SEQ ID NO:25: Primer puro3', synthetic
SEQ ID NO:26: Sequence containing puromycin resistance gene
SEQ ID NO:27: Amino acid sequence corresponding to puromycin resistance gene
SEQ ID NO:28: Primer SV40polyA5', synthetic
SEQ ID NO:29: Primer SV40polyA3', synthetic
SEQ ID NO:30: Primer mIRES-GS5', synthetic
SEQ ID NO:31: Primer mIRES-GS3', synthetic
SEQ ID NO:32: HSA-22KhGH, mature
SEQ ID NO:33: Sequence containing HSA-22KhGH gene, synthetic
SEQ ID NO:34: mHSA-22KhGH, mature
SEQ ID NO:35: Primer YA082, synthetic
SEQ ID NO:36: Primer YA083, synthetic
SEQ ID NO: 37:22KhGH-HSA, mature
SEQ ID NO:38: Sequence containing 22KhGH-HSA gene, synthetic
SEQ ID NO:39: 22KhGH-mHSA
SEQ ID NO:40: Sequence of synthetic gene encoding hGHR ECD
SEQ ID NO:41: Primer YA034, synthetic
SEQ ID NO:42: Primer YA035, synthetic
SEQ ID NO:43: Primer K708, synthetic
SEQ ID NO:44: Primer K709, synthetic
SEQ ID NO:45: Sequence of synthetic gene encoding hGHR, synthetic

SEQUENCE LISTING

GP187-PCT_ST25.txt

The invention claimed is:

1. A human serum albumin mutant-linked protein (A), the human serum albumin mutant linked protein (A) comprising a first polypeptide chain and a second polypeptide chain,
wherein the first polypeptide chain comprises an amino acid sequence of the human serum albumin mutant, the human serum albumin mutant;
(i) comprising an amino acid sequence, in comparison with the amino acid sequence set forth as SEQ ID NO:3, has not more than 10 amino acid residues deleted and/or has not more than 10 amino acid residues replaced, with the proviso that the asparagine residue occurring at position 318 and the threonine at position 320 numbered from the N-terminus of the amino acid sequence set forth as SEQ ID NO:3 are preserved and linked by peptide bonds via a single amino acid residue (X) except proline that is placed between those two amino acid residues, or
(ii) consisting of the amino acid sequence set forth as SEQ ID NO:3, and
the second polypeptide chain linked thereto comprises an amino acid sequence of the protein (A), the protein (A) being different from a human serum albumin that is a mutant or not,
wherein a C-terminus of the second polypeptide chain is linked to a N-terminus of the first polypeptide chain by one or more peptide bonds.

2. The human serum albumin mutant-linked protein (A) according to claim 1, wherein a link between the first polypeptide chain and the second polypeptide chain comprises peptide bonds with a linker.

3. The human serum albumin mutant-linked protein (A) according to claim 2, wherein the linker consists of 1-50 amino acid residues.

4. The human serum albumin mutant-linked protein (A) according to claim 2, wherein the linker consists of 1-6 amino acid residues.

5. The human serum albumin mutant-linked protein (A) according to claim 2, wherein the linker is at least one selected from the group consisting of Gly-Ser, Gly-Gly-Ser, and the amino acid sequences set forth as SEQ ID NO:4, SEQ ID NO:5 and SEQ ID NO:6.

6. The human serum albumin mutant-linked protein (A) according to claim 2, wherein the linker comprises an amino acid sequence Gly-Ser.

7. The human serum albumin mutant-linked protein (A) according to claim 1, wherein the protein (A) is a protein that exhibits a physiological activity when administered to a living body.

8. The human serum albumin mutant-linked protein (A) according to claim 1, wherein the protein (A) is selected from the group consisting of α-L-iduronidase, iduronate-2-sulfatase, glucocerebrosidase, β-galactosidase, GM2 activator protein, β-hexosaminidase A, β-hexosaminidase B, N-acetylglucosamin-1-phosphotransferase, α-mannosidase, β-mannosidase, galactosylceramidase, saposin C, arylsulfatase A, α-L-fucosidase, aspartylglucosaminidase, α-N-acetylgalactosaminidase, acid sphingomyelinase, α-galactosidase, β-glucuronidase, heparan sulfate N-sulfatase, α-Nacetylglucosaminidase, acetyl-CoA:α-glucosaminide N-acetyltransferase, N-acetylglucosamin-6-sulfate sulfatase, acid ceramidase, amylo-1,6-glucosidase, and CLN1 to 10, PD-1 ligands, bone morphogenetic protein (BMP), insulin, prolactin, motilin, adrenocorticotropic hormone (ACTH), melanocyte-stimulating hormone (MSH), thyrotropin-releasing hormone (TRH), thyroid stimulating hormone (TSH), luteinizing hormone (LH), follicle-stimulating hormone (FSH), parathyroid hormone (PTH), thrombopoietin, stem cell factor (SCF), leptin, vasopressin, oxytocin, calcitonin, glucagon, gastrin, secretin, pancreozymin, cholecystokinin, angiotensin, angiostatin, endostatin, human placental lactogen (HPL), human chorionic gonadotropin (HCG), enkephalin, endorphin, interferon α, interferon β, interferon γ, interleukin 2, thymopoietin, thymostimulin, thymus humoral factor (THF), serum thymic factor (FTS), thymosin, thymic factor X, tumor necrosis factor (TNF), granulocyte-colony stimulating factor (G-CSF), macrophage colony-stimulating factor (M-CSF), granulocyte macrophage colony-stimulating factor (GM-CSF), urokinase, tissue plasminogen activator (tPA), dynorphin, bombesin, neurotensin, caerulein, bradykinin, asparaginase, kallikrein, substance P, nerve growth factor (NGF), ciliary neurotrophic factor (CNTF), brain-derived neurotrophic factor (BDNF), glial cell derived neurotrophic factor (GDNF), neurotrophin 3, neurotrophin 4/5, neurotrophin 6, neuregulin 1, activin, basic fibroblast growth factor (bFGF), fibroblast growth factor 2 (FGF2), vascular endothelial growth factor (VEGF), bone morphogenetic protein (BMP), megakaryocyte growth and development factor (MGDF), blood coagulation factor VII, blood coagulation factor VIII, blood coagulation factor IX, superoxide dismutase (SOD), lysozyme chloride, polymyxin B, colistin, gramicidin, bacitracin, gastric inhibitory polypeptide (GIP), vasoactive intestinal peptide (VIP), platelet-derived growth factor (PDGF), growth hormone releasing factor (GRF), epidermal growth factor (EGF), erythropoietin, somatostatin, insulin-like growth factor 1 (IGF-1), 20K growth hormone, 22K growth hormone, and a salt or mutant of thereof.

9. The human serum albumin mutant-linked protein (A) according to claim 1, wherein the protein (A) is 22K growth hormone.

10. The human serum albumin mutant-linked protein (A) according to claim 1, wherein the protein (A) is 20K growth hormone.

11. The human serum albumin mutant-linked protein (A) according to claim 10, wherein the human serum albumin mutant-linked protein (A) consists of the amino acid sequence set forth as SEQ ID NO:12.

12. An expression vector comprising a gene encoding the human serum albumin mutant-linked protein (A) according to claim 1.

13. A mammalian cell transformed with the vector according to claim 12.

* * * * *

```
                        SEQUENCE LISTING

<160> NUMBER OF SEQ ID NOS: 45

<210> SEQ ID NO 1
<211> LENGTH: 585
<212> TYPE: PRT
<213> ORGANISM: Homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

-continued

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu

```
                     530                 535                 540
Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 2
<211> LENGTH: 586
<212> TYPE: PRT
<213> ORGANISM: Homo sapiens

<400> SEQUENCE: 2

Arg Asp Ala His Lys Ser Glu Val Ala His Arg Phe Lys Asp Leu Gly
1               5                   10                  15

Glu Glu Asn Phe Lys Ala Leu Val Leu Ile Ala Phe Ala Gln Tyr Leu
                20                  25                  30

Gln Gln Cys Pro Phe Glu Asp His Val Lys Leu Val Asn Glu Val Thr
            35                  40                  45

Glu Phe Ala Lys Thr Cys Val Ala Asp Glu Ser Ala Glu Asn Cys Asp
50                  55                  60

Lys Ser Leu His Thr Leu Phe Gly Asp Lys Leu Cys Thr Val Ala Thr
65                  70                  75                  80

Leu Arg Glu Thr Tyr Gly Glu Met Ala Asp Cys Cys Ala Lys Gln Glu
                85                  90                  95

Pro Glu Arg Asn Glu Cys Phe Leu Gln His Lys Asp Asp Asn Pro Asn
            100                 105                 110

Leu Pro Arg Leu Val Arg Pro Glu Val Asp Val Met Cys Thr Ala Phe
        115                 120                 125

His Asp Asn Glu Glu Thr Phe Leu Lys Lys Tyr Leu Tyr Glu Ile Ala
130                 135                 140

Arg Arg His Pro Tyr Phe Tyr Ala Pro Glu Leu Leu Phe Phe Ala Lys
145                 150                 155                 160

Arg Tyr Lys Ala Ala Phe Thr Glu Cys Cys Gln Ala Ala Asp Lys Ala
                165                 170                 175

Ala Cys Leu Leu Pro Lys Leu Asp Glu Leu Arg Asp Glu Gly Lys Ala
            180                 185                 190

Ser Ser Ala Lys Gln Arg Leu Lys Cys Ala Ser Leu Gln Lys Phe Gly
        195                 200                 205

Glu Arg Ala Phe Lys Ala Trp Ala Val Ala Arg Leu Ser Gln Arg Phe
210                 215                 220

Pro Lys Ala Glu Phe Ala Glu Val Ser Lys Leu Val Thr Asp Leu Thr
225                 230                 235                 240

Lys Val His Thr Glu Cys Cys His Gly Asp Leu Leu Glu Cys Ala Asp
                245                 250                 255

Asp Arg Ala Asp Leu Ala Lys Tyr Ile Cys Glu Asn Gln Asp Ser Ile
            260                 265                 270

Ser Ser Lys Leu Lys Glu Cys Cys Glu Lys Pro Leu Leu Glu Lys Ser
        275                 280                 285

His Cys Ile Ala Glu Val Glu Asn Asp Glu Met Pro Ala Asp Leu Pro
290                 295                 300

Ser Leu Ala Ala Asp Phe Val Glu Ser Lys Asp Val Cys Lys Asn Tyr
305                 310                 315                 320
```

```
Thr Glu Ala Lys Asp Val Phe Leu Gly Met Phe Leu Tyr Glu Tyr Ala
            325                 330                 335

Arg Arg His Pro Asp Tyr Ser Val Val Leu Leu Leu Arg Leu Ala Lys
        340                 345                 350

Thr Tyr Glu Thr Thr Leu Glu Lys Cys Cys Ala Ala Ala Asp Pro His
            355                 360                 365

Glu Cys Tyr Ala Lys Val Phe Asp Glu Phe Lys Pro Leu Val Glu Glu
        370                 375                 380

Pro Gln Asn Leu Ile Lys Gln Asn Cys Glu Leu Phe Glu Gln Leu Gly
385                 390                 395                 400

Glu Tyr Lys Phe Gln Asn Ala Leu Leu Val Arg Tyr Thr Lys Lys Val
            405                 410                 415

Pro Gln Val Ser Thr Pro Thr Leu Val Glu Val Ser Arg Asn Leu Gly
        420                 425                 430

Lys Val Gly Ser Lys Cys Cys Lys His Pro Glu Ala Lys Arg Met Pro
            435                 440                 445

Cys Ala Glu Asp Tyr Leu Ser Val Val Leu Asn Gln Leu Cys Val Leu
        450                 455                 460

His Glu Lys Thr Pro Val Ser Asp Arg Val Thr Lys Cys Cys Thr Glu
465                 470                 475                 480

Ser Leu Val Asn Arg Arg Pro Cys Phe Ser Ala Leu Glu Val Asp Glu
            485                 490                 495

Thr Tyr Val Pro Lys Glu Phe Asn Ala Glu Thr Phe Thr Phe His Ala
        500                 505                 510

Asp Ile Cys Thr Leu Ser Glu Lys Glu Arg Gln Ile Lys Lys Gln Thr
            515                 520                 525

Ala Leu Val Glu Leu Val Lys His Lys Pro Lys Ala Thr Lys Glu Gln
        530                 535                 540

Leu Lys Ala Val Met Asp Asp Phe Ala Ala Phe Val Glu Lys Cys Cys
545                 550                 555                 560

Lys Ala Asp Asp Lys Glu Thr Cys Phe Ala Glu Glu Gly Lys Lys Leu
            565                 570                 575

Val Ala Ala Ser Gln Ala Ala Leu Gly Leu
        580                 585

<210> SEQ ID NO 3
<211> LENGTH: 585
<212> TYPE: PRT
<213> ORGANISM: Artificial Sequence
<220> FEATURE:
<223> OTHER INFORMATION: Human serum albumin mutant (A320T)

<400> SEQUENCE: 3

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

-continued

```
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Thr
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
```

```
                515                 520                 525
Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 4
<211> LENGTH: 5
<212> TYPE: PRT
<213> ORGANISM: Artificial Sequence
<220> FEATURE:
<223> OTHER INFORMATION: Example of linker

<400> SEQUENCE: 4

Gly Gly Gly Gly Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Example of linker

<400> SEQUENCE: 5

Gly Gly Gly Gly Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Example of linker

<400> SEQUENCE: 6

Ser Gly Gly Gly Gly
1               5

<210> SEQ ID NO 7
<211> LENGTH: 23
<212> TYPE: DNA
<213> ORGANISM: Murine encephalomyocardinitis virus

<400> SEQUENCE: 7
atgataatat ggccacaacc atg                                          23

<210> SEQ ID NO 8
<211> LENGTH: 23
<212> TYPE: DNA
<213> ORGANISM: Artificial Sequence
<220> FEATURE:
<223> OTHER INFORMATION: Partial sequence of IRES from mutant type
      murine encephalomyocardinitis virus

<400> SEQUENCE: 8
atgataagct tgccacaacc atg                                          23

<210> SEQ ID NO 9
<211> LENGTH: 191
```

<212> TYPE: PRT
<213> ORGANISM: Homo sapiens

<400> SEQUENCE: 9

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 10
<211> LENGTH: 176
<212> TYPE: PRT
<213> ORGANISM: Homo sapiens

<400> SEQUENCE: 10

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Asn
            20                  25                  30

Pro Gln Thr Ser Leu Cys Phe Ser Glu Ser Ile Pro Thr Pro Ser Asn
        35                  40                  45

Arg Glu Glu Thr Gln Gln Lys Ser Asn Leu Glu Leu Leu Arg Ile Ser
    50                  55                  60

Leu Leu Leu Ile Gln Ser Trp Leu Glu Pro Val Gln Phe Leu Arg Ser
65                  70                  75                  80

Val Phe Ala Asn Ser Leu Val Tyr Gly Ala Ser Asp Ser Asn Val Tyr
                85                  90                  95

Asp Leu Leu Lys Asp Leu Glu Glu Gly Ile Gln Thr Leu Met Gly Arg
            100                 105                 110

Leu Glu Asp Gly Ser Pro Arg Thr Gly Gln Ile Phe Lys Gln Thr Tyr
        115                 120                 125

Ser Lys Phe Asp Thr Asn Ser His Asn Asp Asp Ala Leu Leu Lys Asn
    130                 135                 140

Tyr Gly Leu Leu Tyr Cys Phe Arg Lys Asp Met Asp Lys Val Glu Thr
145                 150                 155                 160

```
Phe Leu Arg Ile Val Gln Cys Arg Ser Val Glu Gly Ser Cys Gly Phe
                165                 170                 175
```

<210> SEQ ID NO 11
<211> LENGTH: 776
<212> TYPE: PRT
<213> ORGANISM: Artificial Sequence
<220> FEATURE:
<223> OTHER INFORMATION: 22KhGH-mHSA

<400> SEQUENCE: 11

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Asp
            180                 185                 190

Ala His Lys Ser Glu Val Ala His Arg Phe Lys Asp Leu Gly Glu Glu
        195                 200                 205

Asn Phe Lys Ala Leu Val Leu Ile Ala Phe Ala Gln Tyr Leu Gln Gln
    210                 215                 220

Cys Pro Phe Glu Asp His Val Lys Leu Val Asn Glu Val Thr Glu Phe
225                 230                 235                 240

Ala Lys Thr Cys Val Ala Asp Glu Ser Ala Glu Asn Cys Asp Lys Ser
                245                 250                 255

Leu His Thr Leu Phe Gly Asp Lys Leu Cys Thr Val Ala Thr Leu Arg
            260                 265                 270

Glu Thr Tyr Gly Glu Met Ala Asp Cys Cys Ala Lys Gln Glu Pro Glu
        275                 280                 285

Arg Asn Glu Cys Phe Leu Gln His Lys Asp Asp Asn Pro Asn Leu Pro
    290                 295                 300

Arg Leu Val Arg Pro Glu Val Asp Val Met Cys Thr Ala Phe His Asp
305                 310                 315                 320

Asn Glu Glu Thr Phe Leu Lys Lys Tyr Leu Tyr Glu Ile Ala Arg Arg
                325                 330                 335

His Pro Tyr Phe Tyr Ala Pro Glu Leu Leu Phe Ala Lys Arg Tyr
            340                 345                 350
```

```
Lys Ala Ala Phe Thr Glu Cys Cys Gln Ala Ala Asp Lys Ala Ala Cys
            355                 360                 365

Leu Leu Pro Lys Leu Asp Glu Leu Arg Asp Glu Gly Lys Ala Ser Ser
        370                 375                 380

Ala Lys Gln Arg Leu Lys Cys Ala Ser Leu Gln Lys Phe Gly Glu Arg
385                 390                 395                 400

Ala Phe Lys Ala Trp Ala Val Ala Arg Leu Ser Gln Arg Phe Pro Lys
                405                 410                 415

Ala Glu Phe Ala Glu Val Ser Lys Leu Val Thr Asp Leu Thr Lys Val
            420                 425                 430

His Thr Glu Cys Cys His Gly Asp Leu Leu Glu Cys Ala Asp Asp Arg
        435                 440                 445

Ala Asp Leu Ala Lys Tyr Ile Cys Glu Asn Gln Asp Ser Ile Ser Ser
450                 455                 460

Lys Leu Lys Glu Cys Cys Glu Lys Pro Leu Leu Glu Lys Ser His Cys
465                 470                 475                 480

Ile Ala Glu Val Glu Asn Asp Glu Met Pro Ala Asp Leu Pro Ser Leu
                485                 490                 495

Ala Ala Asp Phe Val Glu Ser Lys Asp Val Cys Lys Asn Tyr Thr Glu
            500                 505                 510

Ala Lys Asp Val Phe Leu Gly Met Phe Leu Tyr Glu Tyr Ala Arg Arg
        515                 520                 525

His Pro Asp Tyr Ser Val Val Leu Leu Leu Arg Leu Ala Lys Thr Tyr
    530                 535                 540

Glu Thr Thr Leu Glu Lys Cys Cys Ala Ala Ala Asp Pro His Glu Cys
545                 550                 555                 560

Tyr Ala Lys Val Phe Asp Glu Phe Lys Pro Leu Val Glu Glu Pro Gln
                565                 570                 575

Asn Leu Ile Lys Gln Asn Cys Glu Leu Phe Glu Gln Leu Gly Glu Tyr
            580                 585                 590

Lys Phe Gln Asn Ala Leu Leu Val Arg Tyr Thr Lys Lys Val Pro Gln
        595                 600                 605

Val Ser Thr Pro Thr Leu Val Glu Val Ser Arg Asn Leu Gly Lys Val
    610                 615                 620

Gly Ser Lys Cys Cys Lys His Pro Glu Ala Lys Arg Met Pro Cys Ala
625                 630                 635                 640

Glu Asp Tyr Leu Ser Val Val Leu Asn Gln Leu Cys Val Leu His Glu
                645                 650                 655

Lys Thr Pro Val Ser Asp Arg Val Thr Lys Cys Cys Thr Glu Ser Leu
            660                 665                 670

Val Asn Arg Arg Pro Cys Phe Ser Ala Leu Glu Val Asp Glu Thr Tyr
        675                 680                 685

Val Pro Lys Glu Phe Asn Ala Glu Thr Phe Thr Phe His Ala Asp Ile
    690                 695                 700

Cys Thr Leu Ser Glu Lys Glu Arg Gln Ile Lys Lys Gln Thr Ala Leu
705                 710                 715                 720

Val Glu Leu Val Lys His Lys Pro Lys Ala Thr Lys Glu Gln Leu Lys
                725                 730                 735

Ala Val Met Asp Asp Phe Ala Ala Phe Val Glu Lys Cys Cys Lys Ala
            740                 745                 750

Asp Asp Lys Glu Thr Cys Phe Ala Glu Glu Gly Lys Lys Leu Val Ala
        755                 760                 765

Ala Ser Gln Ala Ala Leu Gly Leu
```

770            775

<210> SEQ ID NO 12
<211> LENGTH: 761
<212> TYPE: PRT
<213> ORGANISM: Artificial Sequence
<220> FEATURE:
<223> OTHER INFORMATION: 20KhGH-mHSA

<400> SEQUENCE: 12

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Asn
            20                  25                  30

Pro Gln Thr Ser Leu Cys Phe Ser Glu Ser Ile Pro Thr Pro Ser Asn
        35                  40                  45

Arg Glu Glu Thr Gln Gln Lys Ser Asn Leu Glu Leu Leu Arg Ile Ser
    50                  55                  60

Leu Leu Leu Ile Gln Ser Trp Leu Glu Pro Val Gln Phe Leu Arg Ser
65                  70                  75                  80

Val Phe Ala Asn Ser Leu Val Tyr Gly Ala Ser Asp Ser Asn Val Tyr
                85                  90                  95

Asp Leu Leu Lys Asp Leu Glu Glu Gly Ile Gln Thr Leu Met Gly Arg
            100                 105                 110

Leu Glu Asp Gly Ser Pro Arg Thr Gly Gln Ile Phe Lys Gln Thr Tyr
        115                 120                 125

Ser Lys Phe Asp Thr Asn Ser His Asn Asp Ala Leu Leu Lys Asn
    130                 135                 140

Tyr Gly Leu Leu Tyr Cys Phe Arg Lys Asp Met Asp Lys Val Glu Thr
145                 150                 155                 160

Phe Leu Arg Ile Val Gln Cys Arg Ser Val Glu Gly Ser Cys Gly Phe
                165                 170                 175

Asp Ala His Lys Ser Glu Val Ala His Arg Phe Lys Asp Leu Gly Glu
            180                 185                 190

Glu Asn Phe Lys Ala Leu Val Leu Ile Ala Phe Ala Gln Tyr Leu Gln
        195                 200                 205

Gln Cys Pro Phe Glu Asp His Val Lys Leu Val Asn Glu Val Thr Glu
    210                 215                 220

Phe Ala Lys Thr Cys Val Ala Asp Glu Ser Ala Glu Asn Cys Asp Lys
225                 230                 235                 240

Ser Leu His Thr Leu Phe Gly Asp Lys Leu Cys Thr Val Ala Thr Leu
                245                 250                 255

Arg Glu Thr Tyr Gly Glu Met Ala Asp Cys Cys Ala Lys Gln Glu Pro
            260                 265                 270

Glu Arg Asn Glu Cys Phe Leu Gln His Lys Asp Asp Asn Pro Asn Leu
        275                 280                 285

Pro Arg Leu Val Arg Pro Glu Val Asp Val Met Cys Thr Ala Phe His
    290                 295                 300

Asp Asn Glu Glu Thr Phe Leu Lys Lys Tyr Leu Tyr Glu Ile Ala Arg
305                 310                 315                 320

Arg His Pro Tyr Phe Tyr Ala Pro Glu Leu Leu Phe Phe Ala Lys Arg
                325                 330                 335

Tyr Lys Ala Ala Phe Thr Glu Cys Cys Gln Ala Ala Asp Lys Ala Ala
            340                 345                 350

Cys Leu Leu Pro Lys Leu Asp Glu Leu Arg Asp Glu Gly Lys Ala Ser

```
            355                 360                 365
Ser Ala Lys Gln Arg Leu Lys Cys Ala Ser Leu Gln Lys Phe Gly Glu
    370                 375                 380

Arg Ala Phe Lys Ala Trp Ala Val Ala Arg Leu Ser Gln Arg Phe Pro
385                 390                 395                 400

Lys Ala Glu Phe Ala Glu Val Ser Lys Leu Val Thr Asp Leu Thr Lys
                405                 410                 415

Val His Thr Glu Cys Cys His Gly Asp Leu Leu Glu Cys Ala Asp Asp
                420                 425                 430

Arg Ala Asp Leu Ala Lys Tyr Ile Cys Glu Asn Gln Asp Ser Ile Ser
            435                 440                 445

Ser Lys Leu Lys Glu Cys Cys Glu Lys Pro Leu Leu Glu Lys Ser His
    450                 455                 460

Cys Ile Ala Glu Val Glu Asn Asp Glu Met Pro Ala Asp Leu Pro Ser
465                 470                 475                 480

Leu Ala Ala Asp Phe Val Glu Ser Lys Asp Val Cys Lys Asn Tyr Thr
                485                 490                 495

Glu Ala Lys Asp Val Phe Leu Gly Met Phe Leu Tyr Glu Tyr Ala Arg
                500                 505                 510

Arg His Pro Asp Tyr Ser Val Val Leu Leu Leu Arg Leu Ala Lys Thr
            515                 520                 525

Tyr Glu Thr Thr Leu Glu Lys Cys Cys Ala Ala Ala Asp Pro His Glu
    530                 535                 540

Cys Tyr Ala Lys Val Phe Asp Glu Phe Lys Pro Leu Val Glu Glu Pro
545                 550                 555                 560

Gln Asn Leu Ile Lys Gln Asn Cys Glu Leu Phe Glu Gln Leu Gly Glu
                565                 570                 575

Tyr Lys Phe Gln Asn Ala Leu Leu Val Arg Tyr Thr Lys Lys Val Pro
                580                 585                 590

Gln Val Ser Thr Pro Thr Leu Val Glu Val Ser Arg Asn Leu Gly Lys
            595                 600                 605

Val Gly Ser Lys Cys Cys Lys His Pro Glu Ala Lys Arg Met Pro Cys
    610                 615                 620

Ala Glu Asp Tyr Leu Ser Val Val Leu Asn Gln Leu Cys Val Leu His
625                 630                 635                 640

Glu Lys Thr Pro Val Ser Asp Arg Val Thr Lys Cys Cys Thr Glu Ser
                645                 650                 655

Leu Val Asn Arg Arg Pro Cys Phe Ser Ala Leu Glu Val Asp Glu Thr
                660                 665                 670

Tyr Val Pro Lys Glu Phe Asn Ala Glu Thr Phe Thr Phe His Ala Asp
            675                 680                 685

Ile Cys Thr Leu Ser Glu Lys Glu Arg Gln Ile Lys Lys Gln Thr Ala
    690                 695                 700

Leu Val Glu Leu Val Lys His Lys Pro Lys Ala Thr Lys Glu Gln Leu
705                 710                 715                 720

Lys Ala Val Met Asp Asp Phe Ala Ala Phe Val Glu Lys Cys Cys Lys
                725                 730                 735

Ala Asp Asp Lys Glu Thr Cys Phe Ala Glu Glu Gly Lys Lys Leu Val
                740                 745                 750

Ala Ala Ser Gln Ala Ala Leu Gly Leu
    755                 760

<210> SEQ ID NO 13
```

```
<211> LENGTH: 20
<212> TYPE: DNA
<213> ORGANISM: Artificial Sequence
<220> FEATURE:
<223> OTHER INFORMATION: Primer Hyg-Sfi5', synthetic

<400> SEQUENCE: 13
gaggccgcct cggcctctga                                                     20

<210> SEQ ID NO 14
<211> LENGTH: 29
<212> TYPE: DNA
<213> ORGANISM: Artificial Sequence
<220> FEATURE:
<223> OTHER INFORMATION: Primer Hyg-BstX3', synthetic

<400> SEQUENCE: 14
aaccatcgtg atgggtgcta ttcctttgc                                           29

<210> SEQ ID NO 15
<211> LENGTH: 2216
<212> TYPE: DNA
<213> ORGANISM: Artificial Sequence
<220> FEATURE:
<223> OTHER INFORMATION: IRES-Hygr-mPGKpA, synthetic

<400> SEQUENCE: 15
ctcgaggaat tcactccttc aggtgcaggc ttgcctatca gaaggtggtg gctggtgtgg         60
ccaactggct cacaaatacc actgagatcg acggtatcga taagcttgat atcgaattcc        120 gcccccccc cctctccctc cccccccct aacgttactg gccgaagccg cttggaataa         180
ggccggtgtg cgtttgtcta tatgttattt tccaccatat tgccgtcttt tggcaatgtg       240
agggcccgga aacctggccc tgtcttcttg acgagcattc ctaggggtct ttcccctctc       300
gccaaaggaa tgcaaggtct gttgaatgtc gtgaaggaag cagttcctct ggaagcttct       360
tgaagacaaa caacgtctgt agcgaccctt gcaggcagc ggaaccccc acctggcgac        420 aggtgcctct gcggccaaaa gccacgtgta agatacac ctgcaaaggc ggcacaaccc        480
cagtgccacg ttgtgagttg gatagttgtg gaaagagtca atggctctc ctcaagcgta        540 ttcaacaagg ggctgaagga tgcccagaag gtaccccatt gtatgggatc tgatctgggg      600
cctcggtgca catgctttac atgtgtttag tcgaggttaa aaaaacgtct aggccccccg       660
aaccacgggg acgtggtttt cctttgaaaa acacgatgat aatatggcca caaccatgaa       720
aaagcctgaa ctcaccgcga cgtctgtcga agtttctg atcgaaaagt tcgacagcgt        780
ctccgacctg atgcagctct cggagggcga agaatctcgt gctttcagct tcgatgtagg       840
agggcgtgga tatgtcctgc gggtaaatag ctgcgccgat ggtttctaca agatcgtta        900 tgttcatcgg cactttgcat cggccgcgct cccgattccg gaagtgcttg acattgggga       960
attcagcgag agcctgacct attgcatctc ccgccgtgca cagggtgtca cgttgcaaga      1020
cctgcctgaa accgaactgc ccgctgttct gcagccggtc gcggaggcca tggatgcgat      1080
cgctgcggcc gatcttagcc agacgagcgg gttcggccca ttcggaccgc aaggaatcgg      1140
tcaatacact acgtggcgtg atttcatatg cgcgattgct gatccccatg tgtatcactg      1200
gcaaactgtg atggacgaca ccgtcagtgc gtccgtcgcg caggctctcg atgagctgat      1260
gctttgggcc gaggactgcc ccgaagtccg gcacctcgtg cacgcggatt tcggctccaa      1320
caatgtcctg acggacaatg gccgcataac agcggtcatt gactggagcg aggcgatgtt      1380
cggggattcc caatacgagg tcgccaacat cttcttctgg aggccgtggt tggcttgtat      1440
```

-continued

```
ggagcagcag acgcgctact tcgagcggag gcatccggag cttgcaggat cgccgcggct    1500
ccgggcgtat atgctccgca ttggtcttga ccaactctat cagagcttgg ttgacggcaa    1560
tttcgatgat gcagcttggg cgcagggtcg atgcgacgca atcgtccgat ccggagccgg    1620
gactgtcggg cgtacacaaa tcgcccgcag aagcgcggcc gtctggaccg atggctgtgt    1680
agaagtactc gccgatagtg aaaccgacg ccccagcact cgtccgaggg caaaggaata     1740
gtcgagaaat tgatgatcta ttaagcaata aagacgtcca ctaaaatgga agttttttcct   1800 gtcatacttt gttaagaagg gtgagaacag agtacctaca ttttgaatgg aaggattgga    1860
gctacggggg tgggggtggg gtgggattag ataaatgcct gctctttact gaaggctctt    1920
tactattgct ttatgataat gtttcatagt tggatatcat aatttaaaca agcaaaacca    1980
aattaagggc cagctcattc ctccactcac gatctataga tccactagct tggcgtaatc    2040
atggtcatag ctgtttcctg tgtgaaattg ttatccgctc acaattccac acaacatacg    2100
agccggaagc ataaagtgta aagcctgggg tgcctaatga gtgagctaac tcacattaat    2160
tgcgttgcgc tcactgcccg ctttccagtc gggaaacctg tcgtgccagc ggatcc        2216
```

<210> SEQ ID NO 16
<211> LENGTH: 341
<212> TYPE: PRT
<213> ORGANISM: Artificial Sequence
<220> FEATURE:
<223> OTHER INFORMATION: Amino acid sequence corresponding to hygromycin resistance gen

<400> SEQUENCE: 16

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
                20                  25                  30

Glu Ser Arg Ala Phe Ser Phe Asp Val Gly Gly Arg Gly Tyr Val Leu
            35                  40                  45

Arg Val Asn Ser Cys Ala Asp Gly Phe Tyr Lys Asp Arg Tyr Val His
        50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220
```

```
Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
            245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
            325                 330                 335

Pro Arg Ala Lys Glu
            340
```

<210> SEQ ID NO 17
<211> LENGTH: 53
<212> TYPE: DNA
<213> ORGANISM: Artificial Sequence
<220> FEATURE:
<223> OTHER INFORMATION: Primer IRES5', synthetic

<400> SEQUENCE: 17
caactcgagc ggccgccccc cccccctctc cctccccccc ccctaacgtt act        53

<210> SEQ ID NO 18
<211> LENGTH: 22
<212> TYPE: DNA
<213> ORGANISM: Artificial Sequence
<220> FEATURE:
<223> OTHER INFORMATION: Primer IRES3', synthetic

<400> SEQUENCE: 18
caagaagctt ccagaggaac tg                                           22

<210> SEQ ID NO 19
<211> LENGTH: 30
<212> TYPE: DNA
<213> ORGANISM: Artificial Sequence
<220> FEATURE:
<223> OTHER INFORMATION: Primer mPGKP5', synthetic

<400> SEQUENCE: 19
gcgagatctt accgggtagg ggaggcgctt                                   30

<210> SEQ ID NO 20
<211> LENGTH: 30
<212> TYPE: DNA
<213> ORGANISM: Artificial Sequence
<220> FEATURE:
<223> OTHER INFORMATION: Primer mPGKP3', synthetic

<400> SEQUENCE: 20
gaggaattcg atgatcggtc gaaaggcccg                                   30

<210> SEQ ID NO 21
<211> LENGTH: 532
<212> TYPE: DNA
<213> ORGANISM: Artificial Sequence
<220> FEATURE:

-continued

<223> OTHER INFORMATION: mPGKp, synthetic

<400> SEQUENCE: 21

```
gcgagatctt accgggtagg ggaggcgctt ttcccaaggc agtctggagc atgcgcttta      60
gcagccccgc tgggcacttg gcgctacaca agtggcctct ggcctcgcac acattccaca     120
tccaccggta ggcgccaacc ggctccgttc tttggtggcc ccttcgcgcc accttctact    180
cctcccctag tcaggaagtt ccccccgcc ccgcagctcg cgtcgtgcag gacgtgacaa     240
atggaagtag cacgtctcac tagtctcgtg cagatggaca gcaccgctga gcaatggaag    300
cgggtaggcc tttggggcag cggccaatag cagctttgct ccttcgcttt ctgggctcag    360
aggctgggaa ggggtgggtc cggggcggg ctcaggggcg ggctcagggg cggggcgggc     420
gcccgaaggt cctccggagg cccggcattc tgcacgcttc aaaagcgcac gtctgccgcg    480
ctgttctcct cttcctcatc tccgggcctt tcgaccgatc atcgaattcc tc            532
```

<210> SEQ ID NO 22
<211> LENGTH: 36
<212> TYPE: DNA
<213> ORGANISM: Artificial Sequence
<220> FEATURE:
<223> OTHER INFORMATION: Primer GS5', synthetic

<400> SEQUENCE: 22

```
aatatggcca caaccatggc gacctcagca agttcc                               36
```

<210> SEQ ID NO 23
<211> LENGTH: 38
<212> TYPE: DNA
<213> ORGANISM: Artificial Sequence
<220> FEATURE:
<223> OTHER INFORMATION: Primer GS3', synthetic

<400> SEQUENCE: 23

```
ggaggatccc tcgagttagt ttttgtattg gaagggct                             38
```

<210> SEQ ID NO 24
<211> LENGTH: 28
<212> TYPE: DNA
<213> ORGANISM: Artificial Sequence
<220> FEATURE:
<223> OTHER INFORMATION: Primer puro5', synthetic

<400> SEQUENCE: 24

```
gcttaagatg accgagtaca agcccacg                                        28
```

<210> SEQ ID NO 25
<211> LENGTH: 30
<212> TYPE: DNA
<213> ORGANISM: Artificial Sequence
<220> FEATURE:
<223> OTHER INFORMATION: Primer puro3', synthetic

<400> SEQUENCE: 25

```
cccatcgtga tggtcaggca ccgggcttgc                                      30
```

<210> SEQ ID NO 26
<211> LENGTH: 620
<212> TYPE: DNA
<213> ORGANISM: Artificial Sequence
<220> FEATURE:
<223> OTHER INFORMATION: Sequence containing puromycin resistance gene,
      synthetic

<400> SEQUENCE: 26

```
gcttaagatg accgagtaca agcccacggt gcgcctcgcc acccgcgacg acgtccccag    60
ggccgtacgc accctcgccg ccgcgttcgc cgactacccc gccacgcgcc acaccgtcga   120
tccggaccgc cacatcgagc gggtcaccga gctgcaagaa ctcttcctca cgcgcgtcgg   180
gctcgacatc ggcaaggtgt gggtcgcgga cgacggcgcc gcggtggcgg tctggaccac   240
gccggagagc gtcgaagcgg gggcggtgtt cgccgagatc ggcccgcgca tggccgagtt   300
gagcggttcc cggctggccg cgcagcaaca gatggaaggc ctcctggcgc cgcaccggcc   360
caaggagccc gcgtggttcc tggccaccgt cggcgtctcg cccgaccacc agggcaaggg   420
tctgggcagc gccgtcgtgc tccccggagt ggaggcggcc gagcgcgccg gggtgcccgc   480
cttcctggag acctccgcgc cccgcaacct ccccttctac gagcggctcg gcttcaccgt   540
caccgccgac gtcgaggtgc ccgaaggacc gcgcacctgg tgcatgaccc gcaagcccgg   600
tgcctgacca tcacgatggg                                               620
```

<210> SEQ ID NO 27
<211> LENGTH: 199
<212> TYPE: PRT
<213> ORGANISM: Artificial Sequence
<220> FEATURE:
<223> OTHER INFORMATION: Amino acid sequence corresponding to puromycin resistance gene

<400> SEQUENCE: 27

```
Met Thr Glu Tyr Lys Pro Thr Val Arg Leu Ala Thr Arg Asp Asp Val
1               5                   10                  15
Pro Arg Ala Val Arg Thr Leu Ala Ala Ala Phe Ala Asp Tyr Pro Ala
            20                  25                  30
Thr Arg His Thr Val Asp Pro Asp Arg His Ile Glu Arg Val Thr Glu
        35                  40                  45
Leu Gln Glu Leu Phe Leu Thr Arg Val Gly Leu Asp Ile Gly Lys Val
    50                  55                  60
Trp Val Ala Asp Asp Gly Ala Ala Val Ala Val Trp Thr Thr Pro Glu
65                  70                  75                  80
Ser Val Glu Ala Gly Ala Val Phe Ala Glu Ile Gly Pro Arg Met Ala
                85                  90                  95
Glu Leu Ser Gly Ser Arg Leu Ala Ala Gln Gln Gln Met Glu Gly Leu
            100                 105                 110
Leu Ala Pro His Arg Pro Lys Glu Pro Ala Trp Phe Leu Ala Thr Val
        115                 120                 125
Gly Val Ser Pro Asp His Gln Gly Lys Gly Leu Gly Ser Ala Val Val
    130                 135                 140
Leu Pro Gly Val Glu Ala Ala Glu Arg Ala Gly Val Pro Ala Phe Leu
145                 150                 155                 160
Glu Thr Ser Ala Pro Arg Asn Leu Pro Phe Tyr Glu Arg Leu Gly Phe
                165                 170                 175
Thr Val Thr Ala Asp Val Glu Val Pro Glu Gly Pro Arg Thr Trp Cys
            180                 185                 190
Met Thr Arg Lys Pro Gly Ala
        195
```

<210> SEQ ID NO 28
<211> LENGTH: 44
<212> TYPE: DNA
<213> ORGANISM: Artificial Sequence
<220> FEATURE:
<223> OTHER INFORMATION: Primer SV40polyA5', synthetic

<400> SEQUENCE: 28
caacaagcgg ccgccctcga gttccctta gtgagggtta atgc       44

<210> SEQ ID NO 29
<211> LENGTH: 24
<212> TYPE: DNA
<213> ORGANISM: Artificial Sequence
<220> FEATURE:
<223> OTHER INFORMATION: Primer SV40polyA3', synthetic

<400> SEQUENCE: 29
cccctgaacc tgaaacataa aatg                            24

<210> SEQ ID NO 30
<211> LENGTH: 25
<212> TYPE: DNA
<213> ORGANISM: Artificial Sequence
<220> FEATURE:
<223> OTHER INFORMATION: Primer mIRES-GS5', synthetic

<400> SEQUENCE: 30
acacgatgat aagcttgcca caacc                           25

<210> SEQ ID NO 31
<211> LENGTH: 21
<212> TYPE: DNA
<213> ORGANISM: Artificial Sequence
<220> FEATURE:
<223> OTHER INFORMATION: Primer mIRES-GS3', synthetic

<400> SEQUENCE: 31
ctccacgata tccctgccat a                               21

<210> SEQ ID NO 32
<211> LENGTH: 776
<212> TYPE: PRT
<213> ORGANISM: Artificial Sequence
<220> FEATURE:
<223> OTHER INFORMATION: HSA-22KhGH, mature

<400> SEQUENCE: 32

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

```
Arg His Pro Tyr Phe Tyr Ala Pro Glu Leu Leu Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560
```

| | | | | | | | | | | | |
|---|---|---|---|---|---|---|---|---|---|---|---|
|Ala|Asp|Asp|Lys|Glu<br>565|Thr|Cys|Phe|Ala|Glu<br>570|Gly|Lys|Lys|Leu|Val<br>575|

Ala Asp Asp Lys Glu Thr Cys Phe Ala Glu Gly Lys Lys Leu Val
              565                 570                 575

Ala Ala Ser Gln Ala Ala Leu Gly Leu Phe Pro Thr Ile Pro Leu Ser
            580                 585                 590

Arg Leu Phe Asp Asn Ala Met Leu Arg Ala His Arg Leu His Gln Leu
        595                 600                 605

Ala Phe Asp Thr Tyr Gln Glu Phe Glu Glu Ala Tyr Ile Pro Lys Glu
    610                 615                 620

Gln Lys Tyr Ser Phe Leu Gln Asn Pro Gln Thr Ser Leu Cys Phe Ser
625                 630                 635                 640

Glu Ser Ile Pro Thr Pro Ser Asn Arg Glu Glu Thr Gln Gln Lys Ser
            645                 650                 655

Asn Leu Glu Leu Leu Arg Ile Ser Leu Leu Leu Ile Gln Ser Trp Leu
            660                 665                 670

Glu Pro Val Gln Phe Leu Arg Ser Val Phe Ala Asn Ser Leu Val Tyr
        675                 680                 685

Gly Ala Ser Asp Ser Asn Val Tyr Asp Leu Leu Lys Asp Leu Glu Glu
    690                 695                 700

Gly Ile Gln Thr Leu Met Gly Arg Leu Glu Asp Gly Ser Pro Arg Thr
705                 710                 715                 720

Gly Gln Ile Phe Lys Gln Thr Tyr Ser Lys Phe Asp Thr Asn Ser His
            725                 730                 735

Asn Asp Asp Ala Leu Leu Lys Asn Tyr Gly Leu Leu Tyr Cys Phe Arg
            740                 745                 750

Lys Asp Met Asp Lys Val Glu Thr Phe Leu Arg Ile Val Gln Cys Arg
        755                 760                 765

Ser Val Glu Gly Ser Cys Gly Phe
    770                 775

<210> SEQ ID NO 33
<211> LENGTH: 2421
<212> TYPE: DNA
<213> ORGANISM: Artificial Sequence
<220> FEATURE:
<223> OTHER INFORMATION: Sequence containing HSA-22KhGH gene, synthetic
<400> SEQUENCE: 33

```
acgcgtcacc atgaagtggg taacctttat ttcccttctt tttctcttta gctcggctta      60
ttccaggggt gtgtttcgtc gagatgcaca caagagtgag gttgctcatc ggtttaaaga     120
tttgggagaa gaaatttcaa agccttggt gttgattgcc tttgctcagt atcttcagca     180
gtgtccattt gaagatcatg taaaattagt gaatgaagta actgaatttg caaaaacatg     240
tgttgctgat gagtcagctg aaaattgtga caaatcactt catacccttt ttggagacaa     300
attatgcaca gttgcaactc ttcgtgaaac ctatggtgaa atggctgact gctgtgcaaa     360
acaagaacct gagagaaatg aatgcttctt gcaacacaaa gatgacaacc caaacctccc     420
ccgattggtg agaccagagg ttgatgtgat gtgcactgct tttcatgaca atgaagagac     480 attttttgaaa aaatacttat atgaaattgc cagaagacat ccttactttt atgccccgga     540
actccttttc tttgctaaaa ggtataaagc tgcttttaca gaatgttgcc aagctgctga     600
taaagctgcc tgcctgttgc caaagctcga tgaacttcgg gatgaaggga aggcttcgtc     660
tgccaaacag agactcaagt gtgccagtct ccaaaaattt ggagaaagag ctttcaaagc     720
atgggcagta gctcgcctga ccagagatt tcccaaagct gagtttgcag aagtttccaa     780
gttagtgaca gatcttacca agtccacac ggaatgctgc catggagatc tgcttgaatg     840
```

```
tgctgatgac agggcggacc ttgccaagta tatctgtgaa atcaagatt cgatctccag      900 taaactgaag gaatgctgtg aaaaacctct gttggaaaaa tcccactgca ttgccgaagt      960
ggaaaatgat gagatgcctg ctgacttgcc ttcattagct gctgattttg ttgaaagtaa     1020
ggatgtttgc aaaaactatg ctgaggcaaa ggatgtcttc ctgggcatgt ttttgtatga     1080
atatgcaaga aggcatcctg attactctgt cgtgctgctg ctgagacttg ccaagacata     1140 tgaaccact ctagagaagt gctgtgccgc tgcagatcct catgaatgct atgccaaagt     1200
gttcgatgaa tttaaacctc ttgtggaaga gcctcagaat ttaatcaaac aaaattgtga     1260 gcttttttgag cagcttggag agtacaaatt ccagaatgcg ctattagttc gttacaccaa     1320
gaaagtaccc caagtgtcaa ctccaactct tgtagaggtc tcaagaaacc taggaaaagt     1380
gggcagcaaa tgttgtaaac atcctgaagc aaaaagaatg ccctgtgcag aagactatct     1440
atccgtggtc ctgaaccagt tatgtgtgtt gcatgagaaa acgccagtaa gtgacagagt     1500
caccaaatgc tgcacagaat ccttggtgaa caggcgacca tgcttttcag ctctggaagt     1560
cgatgaaaca tacgttccca agagtttaa tgctgaaaca ttcaccttcc atgcagatat     1620
atgcacactt tctgagaagg agagacaaat caagaaacaa actgcacttg ttgagctcgt     1680
gaaacacaag cccaaggcaa caaagagca actgaaagct gttatggatg atttcgcagc     1740
ttttgtagag aagtgctgca aggctgacga taaggagacc tgctttgccg aggagggtaa     1800
aaaacttgtt gctgcaagtc aagctgcctt aggcttattc ccaaccattc ccttatccag     1860 gcttttttgac aacgctatgc tccgcgccca tcgtctgcac cagctggcct ttgacaccta     1920
ccaggagttt gaagaagcct atatcccaaa ggaacagaag tattcattcc tgcagaaccc     1980
ccagacctcc ctctgtttct cagagtctat tccgacaccc tccaacaggg aggaaacaca     2040
acagaaatcc aacctagagc tgctccgcat ctccctgctg ctcatccagt cgtggctgga     2100
gcccgtgcag ttcctcagga gtgtcttcgc caacagcctg gtgtacgcgc cctctgacag     2160
caacgtctat gacctcctaa aggacctaga ggaaggcatc caaacgctga tggggaggct     2220
ggaagatggc agccccccga ctgggcagat cttcaagcag acctacagca agttcgacac     2280
aaactcacac aacgatgacg cactactcaa gaactacggg ctgctctact gcttcaggaa     2340
ggacatggac aaggtcgaga cattcctgcg catcgtgcag tgccgctctg tggagggcag     2400
ctgtggcttc taagcggccg c                                              2421
```

<210> SEQ ID NO 34
<211> LENGTH: 776
<212> TYPE: PRT
<213> ORGANISM: Artificial Sequence
<220> FEATURE:
<223> OTHER INFORMATION: mHSA-22KhGH

<400> SEQUENCE: 34

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

```
Arg Glu Thr Tyr Gly Glu Met Ala Asp Cys Cys Ala Lys Gln Glu Pro
            85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Thr
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495
```

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu Phe Pro Thr Ile Pro Leu Ser
            580                 585                 590

Arg Leu Phe Asp Asn Ala Met Leu Arg Ala His Arg Leu His Gln Leu
            595                 600                 605

Ala Phe Asp Thr Tyr Gln Glu Phe Glu Glu Ala Tyr Ile Pro Lys Glu
            610                 615                 620

Gln Lys Tyr Ser Phe Leu Gln Asn Pro Gln Thr Ser Leu Cys Phe Ser
625                 630                 635                 640

Glu Ser Ile Pro Thr Pro Ser Asn Arg Glu Glu Thr Gln Gln Lys Ser
                645                 650                 655

Asn Leu Glu Leu Leu Arg Ile Ser Leu Leu Ile Gln Ser Trp Leu
            660                 665                 670

Glu Pro Val Gln Phe Leu Arg Ser Val Phe Ala Asn Ser Leu Val Tyr
            675                 680                 685

Gly Ala Ser Asp Ser Asn Val Tyr Asp Leu Leu Lys Asp Leu Glu Glu
690                 695                 700

Gly Ile Gln Thr Leu Met Gly Arg Leu Glu Asp Gly Ser Pro Arg Thr
705                 710                 715                 720

Gly Gln Ile Phe Lys Gln Thr Tyr Ser Lys Phe Asp Thr Asn Ser His
                725                 730                 735

Asn Asp Asp Ala Leu Leu Lys Asn Tyr Gly Leu Leu Tyr Cys Phe Arg
                740                 745                 750

Lys Asp Met Asp Lys Val Glu Thr Phe Leu Arg Ile Val Gln Cys Arg
            755                 760                 765

Ser Val Glu Gly Ser Cys Gly Phe
            770                 775

<210> SEQ ID NO 35
<211> LENGTH: 27
<212> TYPE: DNA
<213> ORGANISM: Artificial Sequence
<220> FEATURE:
<223> OTHER INFORMATION: Primer YA082, synthetic

<400> SEQUENCE: 35
aactatactg aggcaaagga tgtcttc                                        27

<210> SEQ ID NO 36
<211> LENGTH: 27
<212> TYPE: DNA
<213> ORGANISM: Artificial Sequence
<220> FEATURE:
<223> OTHER INFORMATION: Primer YA083, synthetic

<400> SEQUENCE: 36
tgcctcagta tagtttttgc aaacatc                                        27

```
<210> SEQ ID NO 37
<211> LENGTH: 776
<212> TYPE: PRT
<213> ORGANISM: Artificial Sequence
<220> FEATURE:
<223> OTHER INFORMATION: 22KhGH-HSA, mature

<400> SEQUENCE: 37

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Asp
            180                 185                 190

Ala His Lys Ser Glu Val Ala His Arg Phe Lys Asp Leu Gly Glu Glu
        195                 200                 205

Asn Phe Lys Ala Leu Val Leu Ile Ala Phe Ala Gln Tyr Leu Gln Gln
    210                 215                 220

Cys Pro Phe Glu Asp His Val Lys Leu Val Asn Glu Val Thr Glu Phe
225                 230                 235                 240

Ala Lys Thr Cys Val Ala Asp Glu Ser Ala Glu Asn Cys Asp Lys Ser
                245                 250                 255

Leu His Thr Leu Phe Gly Asp Lys Leu Cys Thr Val Ala Thr Leu Arg
            260                 265                 270

Glu Thr Tyr Gly Glu Met Ala Asp Cys Cys Ala Lys Gln Glu Pro Glu
        275                 280                 285

Arg Asn Glu Cys Phe Leu Gln His Lys Asp Asp Asn Pro Asn Leu Pro
    290                 295                 300

Arg Leu Val Arg Pro Glu Val Asp Val Met Cys Thr Ala Phe His Asp
305                 310                 315                 320

Asn Glu Glu Thr Phe Leu Lys Lys Tyr Leu Tyr Glu Ile Ala Arg Arg
                325                 330                 335

His Pro Tyr Phe Tyr Ala Pro Glu Leu Leu Phe Phe Ala Lys Arg Tyr
            340                 345                 350

Lys Ala Ala Phe Thr Glu Cys Cys Gln Ala Ala Asp Lys Ala Ala Cys
        355                 360                 365

Leu Leu Pro Lys Leu Asp Glu Leu Arg Asp Glu Gly Lys Ala Ser Ser
```

```
              370                 375                 380
Ala Lys Gln Arg Leu Lys Cys Ala Ser Leu Gln Lys Phe Gly Glu Arg
385                 390                 395                 400

Ala Phe Lys Ala Trp Ala Val Ala Arg Leu Ser Gln Arg Phe Pro Lys
                    405                 410                 415

Ala Glu Phe Ala Glu Val Ser Lys Leu Val Thr Asp Leu Thr Lys Val
                420                 425                 430

His Thr Glu Cys Cys His Gly Asp Leu Leu Glu Cys Ala Asp Asp Arg
            435                 440                 445

Ala Asp Leu Ala Lys Tyr Ile Cys Glu Asn Gln Asp Ser Ile Ser Ser
        450                 455                 460

Lys Leu Lys Glu Cys Cys Glu Lys Pro Leu Leu Glu Lys Ser His Cys
465                 470                 475                 480

Ile Ala Glu Val Glu Asn Asp Glu Met Pro Ala Asp Leu Pro Ser Leu
                    485                 490                 495

Ala Ala Asp Phe Val Glu Ser Lys Asp Val Cys Lys Asn Tyr Ala Glu
                500                 505                 510

Ala Lys Asp Val Phe Leu Gly Met Phe Leu Tyr Glu Tyr Ala Arg Arg
            515                 520                 525

His Pro Asp Tyr Ser Val Val Leu Leu Leu Arg Leu Ala Lys Thr Tyr
        530                 535                 540

Glu Thr Thr Leu Glu Lys Cys Cys Ala Ala Asp Pro His Glu Cys
545                 550                 555                 560

Tyr Ala Lys Val Phe Asp Glu Phe Lys Pro Leu Val Glu Glu Pro Gln
                    565                 570                 575

Asn Leu Ile Lys Gln Asn Cys Glu Leu Phe Glu Gln Leu Gly Glu Tyr
                580                 585                 590

Lys Phe Gln Asn Ala Leu Leu Val Arg Tyr Thr Lys Lys Val Pro Gln
            595                 600                 605

Val Ser Thr Pro Thr Leu Val Glu Val Ser Arg Asn Leu Gly Lys Val
        610                 615                 620

Gly Ser Lys Cys Cys Lys His Pro Glu Ala Lys Arg Met Pro Cys Ala
625                 630                 635                 640

Glu Asp Tyr Leu Ser Val Val Leu Asn Gln Leu Cys Val Leu His Glu
                    645                 650                 655

Lys Thr Pro Val Ser Asp Arg Val Thr Lys Cys Cys Thr Glu Ser Leu
                660                 665                 670

Val Asn Arg Arg Pro Cys Phe Ser Ala Leu Glu Val Asp Glu Thr Tyr
            675                 680                 685

Val Pro Lys Glu Phe Asn Ala Glu Thr Phe Thr Phe His Ala Asp Ile
        690                 695                 700

Cys Thr Leu Ser Glu Lys Glu Arg Gln Ile Lys Lys Gln Thr Ala Leu
705                 710                 715                 720

Val Glu Leu Val Lys His Lys Pro Lys Ala Thr Lys Glu Gln Leu Lys
                    725                 730                 735

Ala Val Met Asp Asp Phe Ala Ala Phe Val Glu Lys Cys Cys Lys Ala
                740                 745                 750

Asp Asp Lys Glu Thr Cys Phe Ala Glu Glu Gly Lys Lys Leu Val Ala
            755                 760                 765

Ala Ser Gln Ala Ala Leu Gly Leu
        770                 775

<210> SEQ ID NO 38
```

<211> LENGTH: 2427
<212> TYPE: DNA
<213> ORGANISM: Artificial Sequence
<220> FEATURE:
<223> OTHER INFORMATION: Sequence containing 22KhGH-HSA gene, synthetic

<400> SEQUENCE: 38

| | | | | | |
|---|---|---|---|---|---|
| acgcgtcacc | atggctacag | gctcccggac | gtccctgctc | ctggcttttg | gcctgctctg | 60 |
| cctgccctgg | cttcaagagg | gcagtgcctt | cccaaccatt | cccttatcca | ggcttttgta | 120 |
| caacgctatg | ctccgcgccc | atcgtctgca | ccagctggcc | tttgacacct | accaggagtt | 180 |
| tgaagaagcc | tatatcccaa | aggaacagaa | gtattcattc | ctgcagaacc | cccagacctc | 240 |
| cctctgtttc | tcagagtcta | ttccgacacc | ctccaacagg | gaggaaacac | aacagaaatc | 300 |
| caacctagag | ctgctccgca | tctccctgct | gctcatccag | tcgtggctgg | agcccgtgca | 360 |
| gttcctcagg | agtgtcttcg | ccaacagcct | ggtgtacggc | gcctctgaca | gcaacgtcta | 420 |
| tgacctccta | aaggacctag | aggaaggcat | ccaaacgctg | atggggaggc | tggaagatgg | 480 |
| cagccccgg | actgggcaga | tcttcaagca | gacctacagc | aagttcgaca | caaactcaca | 540 |
| caacgatgac | gcactactca | gaactacgg | gctgctctac | tgcttcagga | aggacatgga | 600 |
| caaggtcgag | acattcctgc | gcatcgtgca | gtgccgctct | gtggagggca | gctgtggctt | 660 |
| cgatgcacac | aagagtgagg | ttgctcatcg | gtttaaagat | tgggagaag | aaaatttcaa | 720 |
| agccttggtg | ttgattgcct | ttgctcagta | tcttcagcag | tgtccatttg | aagatcatgt | 780 |
| aaaattagtg | aatgaagtaa | ctgaatttgc | aaaaacatgt | gttgctgatg | agtcagctga | 840 |
| aaattgtgac | aaatcacttc | ataccctttt | tggagacaaa | ttatgcacag | ttgcaactct | 900 |
| tcgtgaaacc | tatggtgaaa | tggctgactg | ctgtgcaaaa | caagaacctg | agagaaatga | 960 |
| atgcttcttg | caacacaaag | atgacaaccc | aaacctcccc | cgattggtga | gaccagaggt | 1020 |
| tgatgtgatg | tgcactgctt | ttcatgacaa | tgaagagaca | ttttttgaaaa | aatacttata | 1080 |
| tgaaattgcc | agaagacatc | cttactttta | tgccccggaa | ctccttttct | ttgctaaaag | 1140 |
| gtataaagct | gcttttacag | aatgttgcca | agctgctgat | aaagctgcct | gcctgttgcc | 1200 |
| aaagctcgat | gaacttcggg | atgaagggaa | ggcttcgtct | gccaaacaga | gactcaagtg | 1260 |
| tgccagtctc | caaaaatttg | gagaaagagc | tttcaaagca | tgggcagtag | ctcgcctgag | 1320 |
| ccagagattt | cccaaagctg | agtttgcaga | agtttccaag | ttagtgacag | atcttaccaa | 1380 |
| agtccacacg | gaatgctgcc | atggagatct | gcttgaatgt | gctgatgaca | gggcggacct | 1440 |
| tgccaagtat | atctgtgaaa | atcaagattc | gatctccagt | aaactgaagg | aatgctgtga | 1500 |
| aaaacctctg | ttggaaaaat | cccactgcat | tgccgaagtg | gaaaatgatg | agatgcctgc | 1560 |
| tgacttgcct | tcattagctg | ctgatttgt | tgaaagtaag | gatgtttgca | aaaactatgc | 1620 |
| tgaggcaaag | gatgtcttcc | tgggcatgtt | tttgtatgaa | tatgcaagaa | ggcatcctga | 1680 |
| ttactctgtc | gtgctgctgc | tgagacttgc | caagacatat | gaaaccactc | tagagaagtg | 1740 |
| ctgtgccgct | gcagatcctc | atgaatgcta | tgccaaagtg | ttcgatgaat | ttaaacctct | 1800 |
| tgtggaagag | cctcagaatt | taatcaaaca | aaattgtgag | cttttgagc | agcttggaga | 1860 |
| gtacaaattc | cagaatgcgc | tattagttcg | ttacaccaag | aaagtacccc | aagtgtcaac | 1920 |
| tccaactctt | gtagaggtct | caagaaacct | aggaaaagtg | ggcagcaaat | gttgtaaaca | 1980 |
| tcctgaagca | aaaagaatgc | cctgtgcaga | agactatcta | tccgtggtcc | tgaaccagtt | 2040 |
| atgtgtgttg | catgagaaaa | cgccagtaag | tgacagagtc | accaaatgct | gcacagaatc | 2100 |
| cttggtgaac | aggcgaccat | gcttttcagc | tctggaagtc | gatgaaacat | acgttcccaa | 2160 |

```
agagtttaat gctgaaacat tcaccttcca tgcagatata tgcacactt  ctgagaagga    2220 gagacaaatc aagaaacaaa ctgcacttgt tgagctcgtg aaacacaagc ccaaggcaac    2280
aaaagagcaa ctgaaagctg ttatggatga tttcgcagct tttgtagaga agtgctgcaa    2340
ggctgacgat aaggagacct gctttgccga ggagggtaaa aaacttgttg ctgcaagtca    2400
agctgcctta ggcttataag cggccgc                                        2427
```

```
<210> SEQ ID NO 39
<211> LENGTH: 776
<212> TYPE: PRT
<213> ORGANISM: Artificial Sequence
<220> FEATURE:
<223> OTHER INFORMATION: 22KhGH-mHSA, mature

<400> SEQUENCE: 39
```

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Asp
            180                 185                 190

Ala His Lys Ser Glu Val Ala His Arg Phe Lys Asp Leu Gly Glu Glu
        195                 200                 205

Asn Phe Lys Ala Leu Val Leu Ile Ala Phe Ala Gln Tyr Leu Gln Gln
    210                 215                 220

Cys Pro Phe Glu Asp His Val Lys Leu Val Asn Glu Val Thr Glu Phe
225                 230                 235                 240

Ala Lys Thr Cys Val Ala Asp Glu Ser Ala Glu Asn Cys Asp Lys Ser
                245                 250                 255

Leu His Thr Leu Phe Gly Asp Lys Leu Cys Thr Val Ala Thr Leu Arg
            260                 265                 270

Glu Thr Tyr Gly Glu Met Ala Asp Cys Cys Ala Lys Gln Glu Pro Glu
        275                 280                 285

Arg Asn Glu Cys Phe Leu Gln His Lys Asp Asp Asn Pro Asn Leu Pro
    290                 295                 300

Arg Leu Val Arg Pro Glu Val Asp Val Met Cys Thr Ala Phe His Asp

```
                305                 310                 315                 320
Asn Glu Glu Thr Phe Leu Lys Lys Tyr Leu Tyr Glu Ile Ala Arg Arg
                    325                 330                 335
His Pro Tyr Phe Tyr Ala Pro Glu Leu Leu Phe Phe Ala Lys Arg Tyr
                340                 345                 350
Lys Ala Ala Phe Thr Glu Cys Cys Gln Ala Ala Asp Lys Ala Ala Cys
                    355                 360                 365
Leu Leu Pro Lys Leu Asp Glu Leu Arg Asp Glu Gly Lys Ala Ser Ser
            370                 375                 380
Ala Lys Gln Arg Leu Lys Cys Ala Ser Leu Gln Lys Phe Gly Glu Arg
385                 390                 395                 400
Ala Phe Lys Ala Trp Ala Val Ala Arg Leu Ser Gln Arg Phe Pro Lys
                        405                 410                 415
Ala Glu Phe Ala Glu Val Ser Lys Leu Val Thr Asp Leu Thr Lys Val
                420                 425                 430
His Thr Glu Cys Cys His Gly Asp Leu Leu Glu Cys Ala Asp Asp Arg
                    435                 440                 445
Ala Asp Leu Ala Lys Tyr Ile Cys Glu Asn Gln Asp Ser Ile Ser Ser
            450                 455                 460
Lys Leu Lys Glu Cys Cys Glu Lys Pro Leu Leu Glu Lys Ser His Cys
465                 470                 475                 480
Ile Ala Glu Val Glu Asn Asp Glu Met Pro Ala Asp Leu Pro Ser Leu
                        485                 490                 495
Ala Ala Asp Phe Val Glu Ser Lys Asp Val Cys Lys Asn Tyr Thr Glu
                500                 505                 510
Ala Lys Asp Val Phe Leu Gly Met Phe Leu Tyr Glu Tyr Ala Arg Arg
            515                 520                 525
His Pro Asp Tyr Ser Val Val Leu Leu Leu Arg Leu Ala Lys Thr Tyr
        530                 535                 540
Glu Thr Thr Leu Glu Lys Cys Cys Ala Ala Ala Asp Pro His Glu Cys
545                 550                 555                 560
Tyr Ala Lys Val Phe Asp Glu Phe Lys Pro Leu Val Glu Glu Pro Gln
                        565                 570                 575
Asn Leu Ile Lys Gln Asn Cys Glu Leu Phe Glu Gln Leu Gly Glu Tyr
                580                 585                 590
Lys Phe Gln Asn Ala Leu Leu Val Arg Tyr Thr Lys Lys Val Pro Gln
            595                 600                 605
Val Ser Thr Pro Thr Leu Val Glu Val Ser Arg Asn Leu Gly Lys Val
        610                 615                 620
Gly Ser Lys Cys Cys Lys His Pro Glu Ala Lys Arg Met Pro Cys Ala
625                 630                 635                 640
Glu Asp Tyr Leu Ser Val Val Leu Asn Gln Leu Cys Val Leu His Glu
                        645                 650                 655
Lys Thr Pro Val Ser Asp Arg Val Thr Lys Cys Cys Thr Glu Ser Leu
                660                 665                 670
Val Asn Arg Arg Pro Cys Phe Ser Ala Leu Glu Val Asp Glu Thr Tyr
            675                 680                 685
Val Pro Lys Glu Phe Asn Ala Glu Thr Phe Thr Phe His Ala Asp Ile
        690                 695                 700
Cys Thr Leu Ser Glu Lys Glu Arg Gln Ile Lys Lys Gln Thr Ala Leu
705                 710                 715                 720
Val Glu Leu Val Lys His Lys Pro Lys Ala Thr Lys Glu Gln Leu Lys
                        725                 730                 735
```

Ala Val Met Asp Asp Phe Ala Ala Phe Val Glu Lys Cys Cys Lys Ala
                740                 745                 750

Asp Asp Lys Glu Thr Cys Phe Ala Glu Glu Gly Lys Lys Leu Val Ala
            755                 760                 765

Ala Ser Gln Ala Ala Leu Gly Leu
        770                 775

<210> SEQ ID NO 40
<211> LENGTH: 792
<212> TYPE: DNA
<213> ORGANISM: Artificial Sequence
<220> FEATURE:
<223> OTHER INFORMATION: Sequence coding synthetic hGHR ECD gene

<400> SEQUENCE: 40
atggacctgt ggcagctcct cctgaccctc gctctggctg ctcctccga tgccttctcc      60 ggctccgagg ccaccgctgc tatcctgagc agggctccct ggtccctgca gagcgtcaac    120
cctggcctga agaccaactc ctccaaagag cccaagttca caaagtgcag gtcccccgag    180
agggagacct tctcctgtca ttggaccgac gaggtgcacc acggcaccaa gaacctgggc    240
cccatccagc tcttctacac caggaggaac acccaagagt ggacacagga gtggaaggag    300
tgccccgatt acgtgtccgc cggcgagaac agctgctact tcaactcctc cttcacatcc    360
atctggattc cttattgcat caaactgacc tccaacggcg gcacagtgga tgagaagtgc    420
ttcagcgtcg acgagatcgt gcagcccgat cccccccatcg ctctgaactg gaccctgctg    480
aatgtgtccc tgaccggcat ccacgccgat attcaggtga ggtgggaggc tcccaggaac    540
gctgacatcc agaagggctg gatggtcctg gagtacgagc tgcagtacaa ggaggtcaac    600
gagaccaagt ggaaaatgat ggaccctatc ctgacaacat ccgtccctgt gtacagcctg    660
aaggtggaca agagtacga ggtgaggtg aggagcaaac agcggaatag cggcaactac    720
ggagaattct ccgaggtgct gtatgtgacc ctgccccaga tgtcccagtt cacctgtgaa    780 gaggacttttt ac                                                        792

<210> SEQ ID NO 41
<211> LENGTH: 42
<212> TYPE: DNA
<213> ORGANISM: Artificial Sequence
<220> FEATURE:
<223> OTHER INFORMATION: Primer YA034, synthetic

<400> SEQUENCE: 41
ccgacgcgtc gccaccatgg acctgtggca gctcctcctg ac                        42

<210> SEQ ID NO 42
<211> LENGTH: 67
<212> TYPE: DNA
<213> ORGANISM: Artificial Sequence
<220> FEATURE:
<223> OTHER INFORMATION: Primer YA035, synthetic

<400> SEQUENCE: 42
cactgttagc ccgaatattc cgaagatgat aattaggagc catgggaagt aaaagtcctc     60
ttcacag                                                               67

<210> SEQ ID NO 43
<211> LENGTH: 43
<212> TYPE: DNA
<213> ORGANISM: Artificial Sequence

```
<220> FEATURE:
<223> OTHER INFORMATION: Primer K708, synthetic

<400> SEQUENCE: 43
ccggtcgacc gccaccatgg atctctggca gctgctgttg acc            43

<210> SEQ ID NO 44
<211> LENGTH: 39
<212> TYPE: DNA
<213> ORGANISM: Artificial Sequence
<220> FEATURE:
<223> OTHER INFORMATION: Primer K709, synthetic

<400> SEQUENCE: 44
tttggcggcc gcctaaggca tgattttgtt cagttggtc                 39

<210> SEQ ID NO 45
<211> LENGTH: 1917
<212> TYPE: DNA
<213> ORGANISM: Artificial Sequence
<220> FEATURE:
<223> OTHER INFORMATION: Sequence coding synthetic hGHR gene

<400> SEQUENCE: 45
atggacctgt ggcagctcct cctgaccctc gctctggctg ctcctccga tgccttctcc    60 ggctccgagg ccaccgctgc tatcctgagc agggctccct ggtccctgca gagcgtcaac   120
cctggcctga gaccaactc ctccaaagag cccaagttca caaagtgcag gtccccgag    180 agggagacct ctcctgtca ttggaccgac gaggtgcacc acggcaccaa gaacctgggc   240
cccatccagc tcttctacac caggaggaac acccaagagt ggacacagga gtggaaggag   300
tgccccgatt acgtgtccgc cggcgagaac agctgctact tcaactcctc cttcacatcc   360
atctggattc cttattgcat caaactgacc tccaacggcg gcacagtgga tgagaagtgc   420
ttcagcgtcg acgagatcgt gcagcccgat cccccatcg ctctgaactg accctgctg    480 aatgtgtccc tgaccggcat ccacgccgat attcaggtga ggtgggaggc tcccaggaac   540
gctgacatcc agaagggctg gatggtcctg gagtacgagc tgcagtacaa ggaggtcaac   600
gagaccaagt ggaaaatgat ggaccctatc ctgacaacat ccgtccctgt gtacagcctg   660
aaggtggaca agagtacga ggtgagggtg aggagcaaac agcggaatag cggcaactac   720
ggagaattct ccgaggtgct gtatgtgacc ctgcccagga gtcccagtt cacctgtgaa   780 gaggactttt acttcccatg gctcctaatt atcatcttcg gaatattcgg ctaacagtg    840 atgctatttg tattcttatt ttctaaacag caaaggatta aatgctgat ctgcccccca    900 gttccagttc aaagattaa aggaatcgat ccagatctcc tcaaggaagg aaaattagag   960
gaggtgaaca caatcttagc cattcatgat agctataaac ccgaattcca cagtgatgac  1020
tcttgggttg aatttattga gctagatatt gatgagccag atgaaaagac tgaggaatca  1080
gacacagaca gacttctaag cagtgaccat gagaaatcac atagtaacct aggggtgaag  1140
gatggcgact ctggacgtac cagctgttgt gaacctgaca ttctggagac tgatttcaat  1200
gccaatgaca tacatgaggg taccctcaga ggttgctcagc cacagaggtt aaaaggggaa  1260
gcagatctct tatgccttga ccagaagaat caaaataact cacctatca tgatgcttgc   1320 cctgctactc agcagcccag tgttatccaa gcagagaaaa acaaaccaca accacttcct   1380
actgaaggag ctgagtcaac tcaccaagct gcccatattc agctaagcaa tccaagttca  1440
ctgtcaaaca tcgacttta tgcccaggtg agcgacatta caccagcagg tagtgtggtc   1500
```

```
ctttccccgg gccaaaagaa taaggcaggg atgtcccaat gtgacatgca cccggaaatg    1560
gtctcactct gccaagaaaa cttccttatg gacaatgcct acttctgtga ggcagatgcc    1620
aaaaagtgca tccctgtggc tcctcacatc aaggttgaat cacacataca gccaagctta    1680
aaccaagagg acatttacat caccacagaa agccttacca ctgctgctgg gaggcctggg    1740
acaggagaac atgttccagg ttctgagatg cctgtcccag actatacctc cattcatata    1800
gtacagtccc cacagggcct catactcaat gcgactgcct tgcccttgcc tgacaaagag    1860
tttctctcat catgtggcta tgtgagcaca gaccaactga acaaaatcat gccttag      1917
```